US012582499B1

(12) United States Patent
Garibaldi et al.

(10) Patent No.:  US 12,582,499 B1
(45) Date of Patent:       Mar. 24, 2026

(54) SYSTEM AND METHOD FOR DATA VISUALIZATION AND USER INTERFACES OF FLUORESCENTLY TAGGED TISSUE IN A SURGICAL FIELD

(71) Applicant: Integro Theranostics, LLC, Chesterfield, MO (US)

(72) Inventors: Jeff M. Garibaldi, St. Louis, MO (US); Nicholas R. Staten, Kirkwood, MO (US); Abbas Dhilawala, Houston, TX (US); Maya KeShil Waterland, Austin, TX (US)

(73) Assignee: Integro Theranostics, LLC, Chesterfield, MO (US)

( * ) Notice: Subject to any disclaimer, the term of this patent is extended or adjusted under 35 U.S.C. 154(b) by 241 days.

(21) Appl. No.: 18/383,025

(22) Filed: Oct. 23, 2023

Related U.S. Application Data

(60) Provisional application No. 63/418,964, filed on Oct. 24, 2022.

(51) Int. Cl.
A61B 90/00          (2016.01)
A61B 34/20          (2016.01)

(52) U.S. Cl.
CPC ............ *A61B 90/361* (2016.02); *A61B 34/20* (2016.02); *A61B 90/37* (2016.02); *A61B 2034/2057* (2016.02); *A61B 2090/3612* (2016.02); *A61B 2090/373* (2016.02)

(58) Field of Classification Search
CPC ....... A61B 90/361; A61B 90/37; A61B 34/20; A61B 2034/2057; A61B 2090/3612; A61B 2090/373
See application file for complete search history.

(56) References Cited

U.S. PATENT DOCUMENTS

2006/0173358 A1 *   8/2006   Xie ..................... A61B 1/0646
                                                                             600/476

* cited by examiner

*Primary Examiner* — Michael T Rozanski
(74) *Attorney, Agent, or Firm* — Harness, Dickey & Pierce, P.L.C.

(57)                    ABSTRACT

A system and method for visualizing a surgical field containing a plurality of discrete regions of fluorescing tissue is disclosed. The method includes imaging a portion of the surgical field; displaying an image of the portion of the surgical field captured by the camera; generating a signaling zone on the display at least partially surrounding the image of the portion of the surgical field, and displaying in this signaling zone an indicator of at least one adjacent discrete region of fluorescing tissue that is outside of the displayed image. Each indicator is located in that portion of the signaling zone closest to the adjacent discrete region of fluorescing tissue that the indicator represents, and the appearance of the indicator (color, size, shape) can indicate a property of the region that the indicator represents, such as size, fluorescence intensity, distance, or importance.

20 Claims, 39 Drawing Sheets

| | Fluorescing Tissue | FIG. 3A |
| --- | --- | --- |
| | IR Emitting Tissue | |

| | Fluorescing Tissue | |
| --- | --- | --- |
| | IR Emitting Tissue | FIG. 3B |

| | Fluorescing Tissue | FIG. 3C |
| --- | --- | --- |
| | IR Emitting Tissue | |

| | Fluorescing Tissue | |
| --- | --- | --- |
| | IR Emitting Tissue | FIG. 3D |

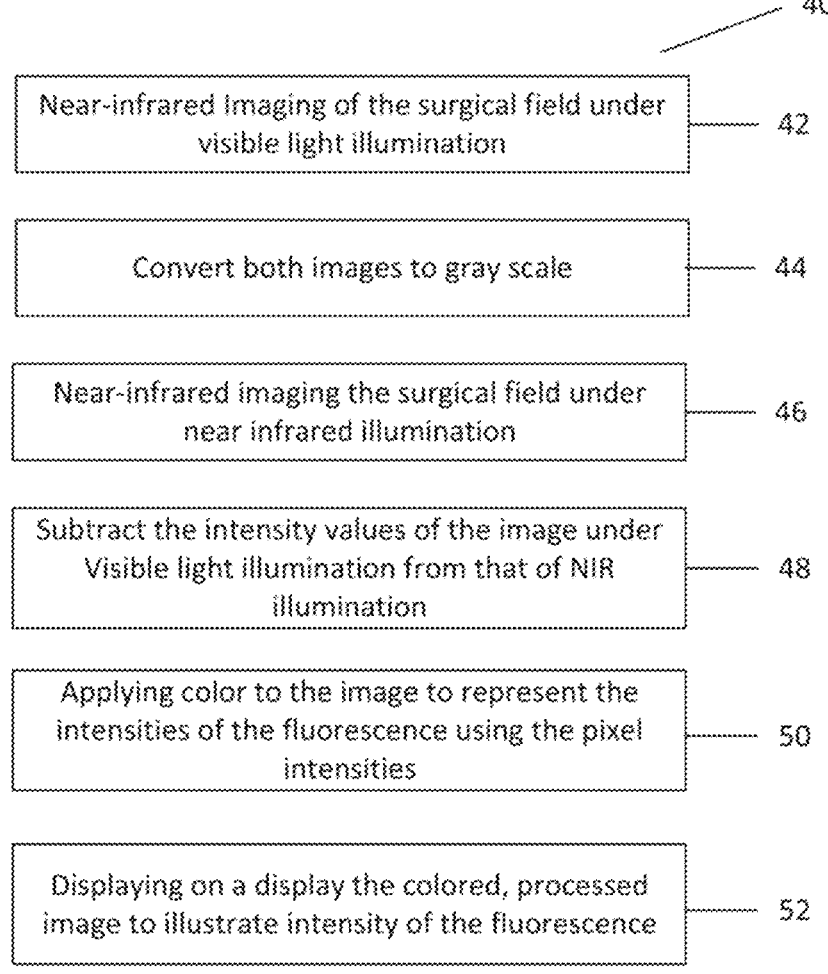

40

| Near-infrared imaging of the surgical field under visible light illumination | 42 |

| Convert both images to gray scale | 44 |

| Near-infrared imaging the surgical field under near infrared illumination | 46 |

| Subtract the intensity values of the image under Visible light illumination from that of NIR illumination | 48 |

| Applying color to the image to represent the intensities of the fluorescence using the pixel intensities | 50 |

| Displaying on a display the colored, processed image to illustrate intensity of the fluorescence | 52 |

FIG. 4

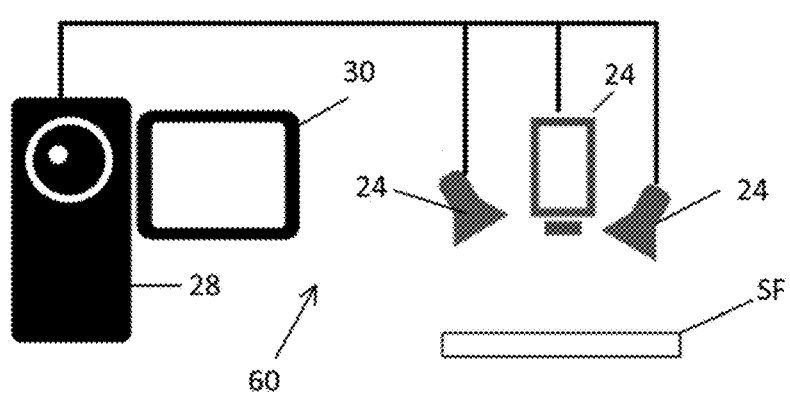
Fig. 5
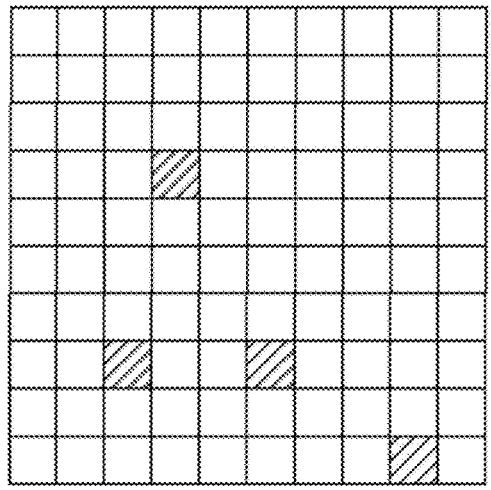
Fluorescing Tissue          FIG. 6A
Suspected
Reflecting Tissue
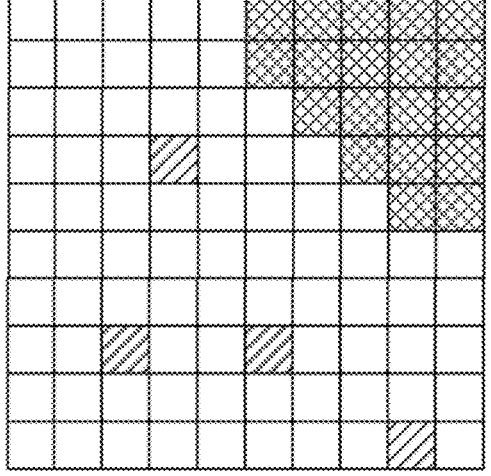
Fluorescing Tissue          FIG. 6B
Suspected
Reflecting Tissue
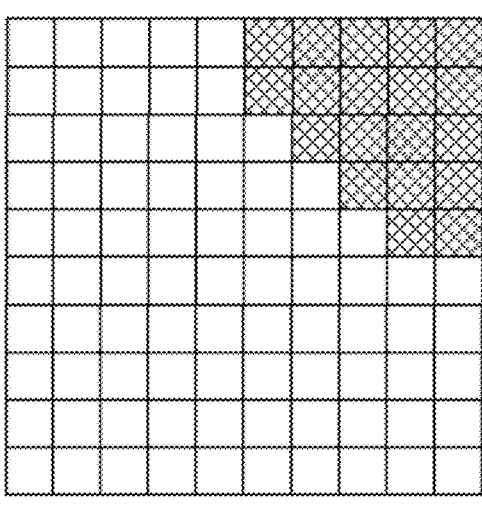
Fluorescing Tissue          FIG. 6C
IR Emitting Tissue
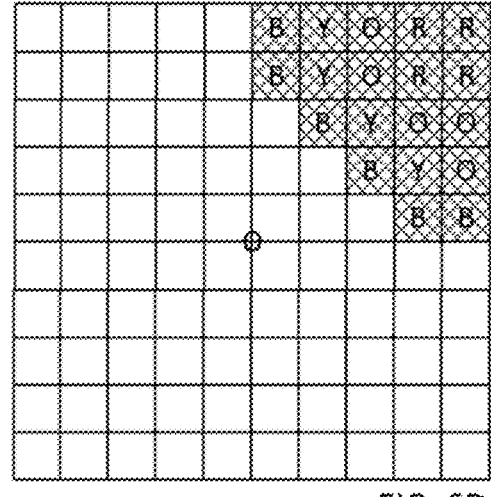
Fluorescing Tissue          FIG. 6D
IR Emitting Tissue

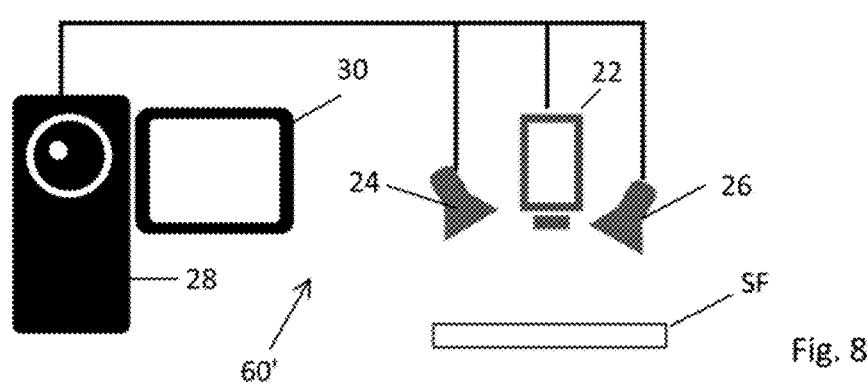
Fig. 8
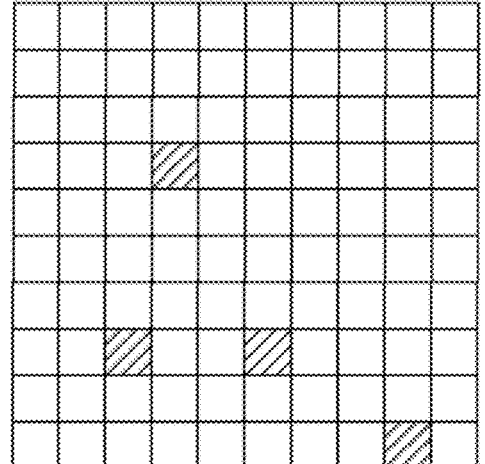
Fluorescing Tissue FIG. 9A
IR Emitting Tissue
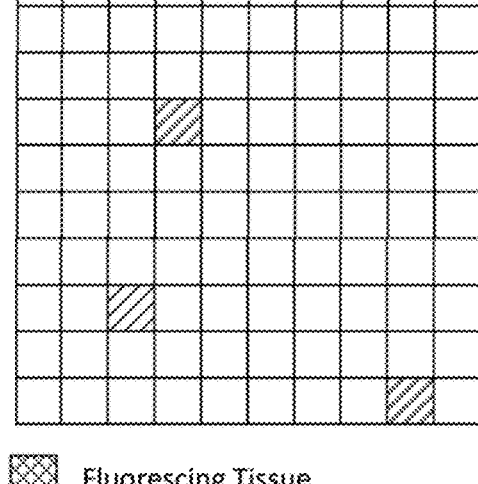
Fluorescing Tissue
IR Emitting Tissue FIG. 9B
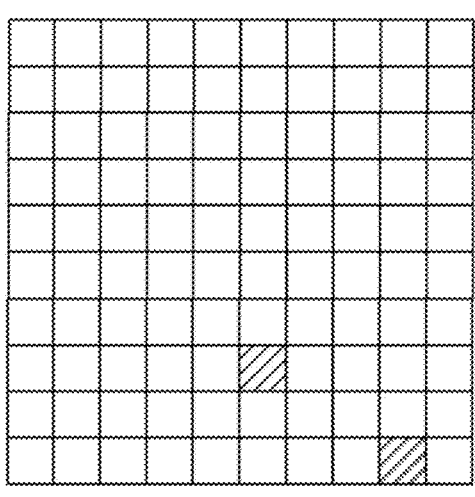
Fluorescing Tissue FIG. 9C
IR Emitting Tissue
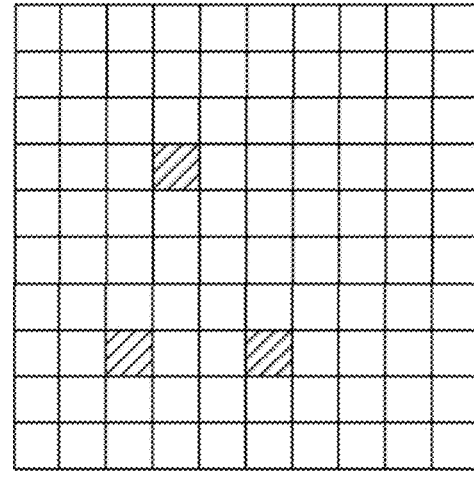
Fluorescing Tissue
IR Emitting Tissue FIG. 9D

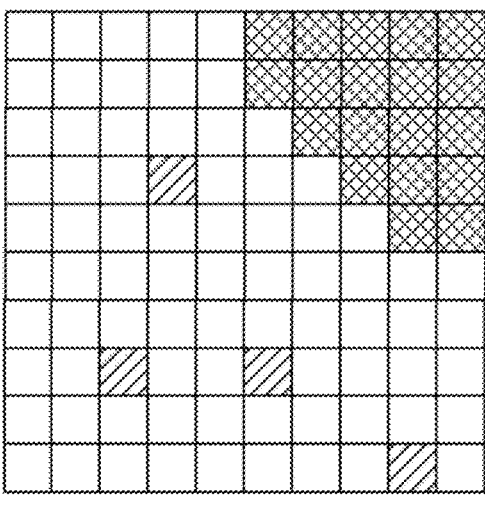
Fluorescing Tissue        FIG. 10A
Suspected
Reflecting Tissue
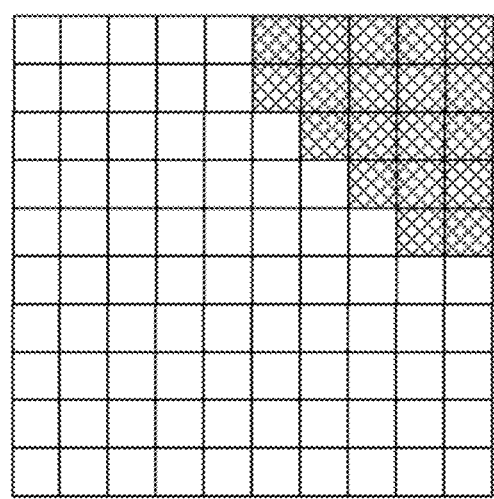
Fluorescing Tissue        FIG. 10B
IR Emitting Tissue
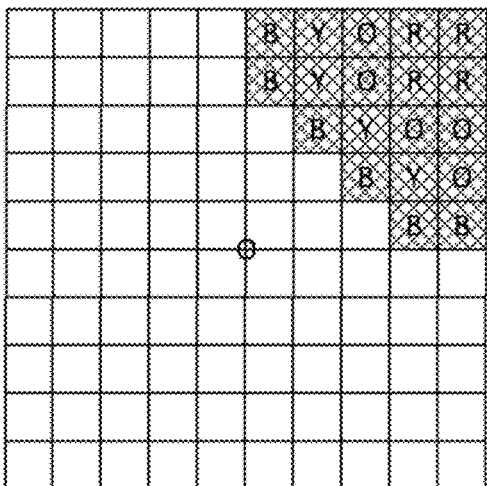
Fluorescing Tissue        FIG. 10C
IR Emitting Tissue

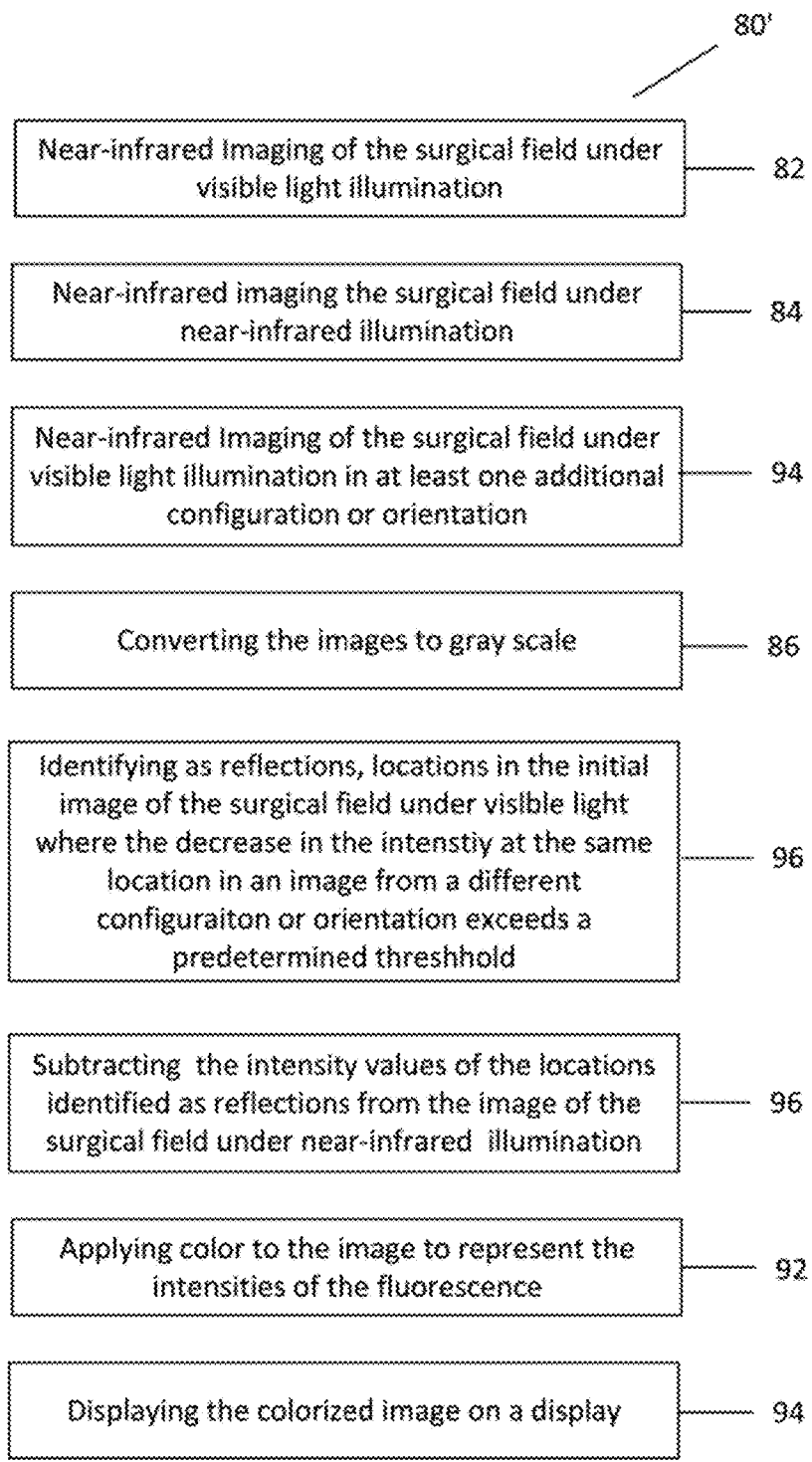

80'

Near-infrared Imaging of the surgical field under visible light illumination — 82

Near-infrared imaging the surgical field under near-infrared illumination — 84

Near-infrared Imaging of the surgical field under visible light illumination in at least one additional configuration or orientation — 94

Converting the images to gray scale — 86

Identifying as reflections, locations in the initial image of the surgical field under visible light where the decrease in the intenstiy at the same location in an image from a different configuraiton or orientation exceeds a predetermined threshhold — 96

Subtracting the intensity values of the locations identified as reflections from the image of the surgical field under near-infrared illumination — 96

Applying color to the image to represent the intensities of the fluorescence — 92

Displaying the colorized image on a display — 94

FIG. 11

| | |
|---|---|
| Imaging of the surgical field under near-infrared light illumination | 152 |
| Processing the image of tissue adjacent to the fluorescent tissue to compare it with images of abnormal tissue | 154 |
| Applying color to the image to identify the abnormal tissue | 156 |
| Displaying the processed, colored image on a dislpay | 158 |

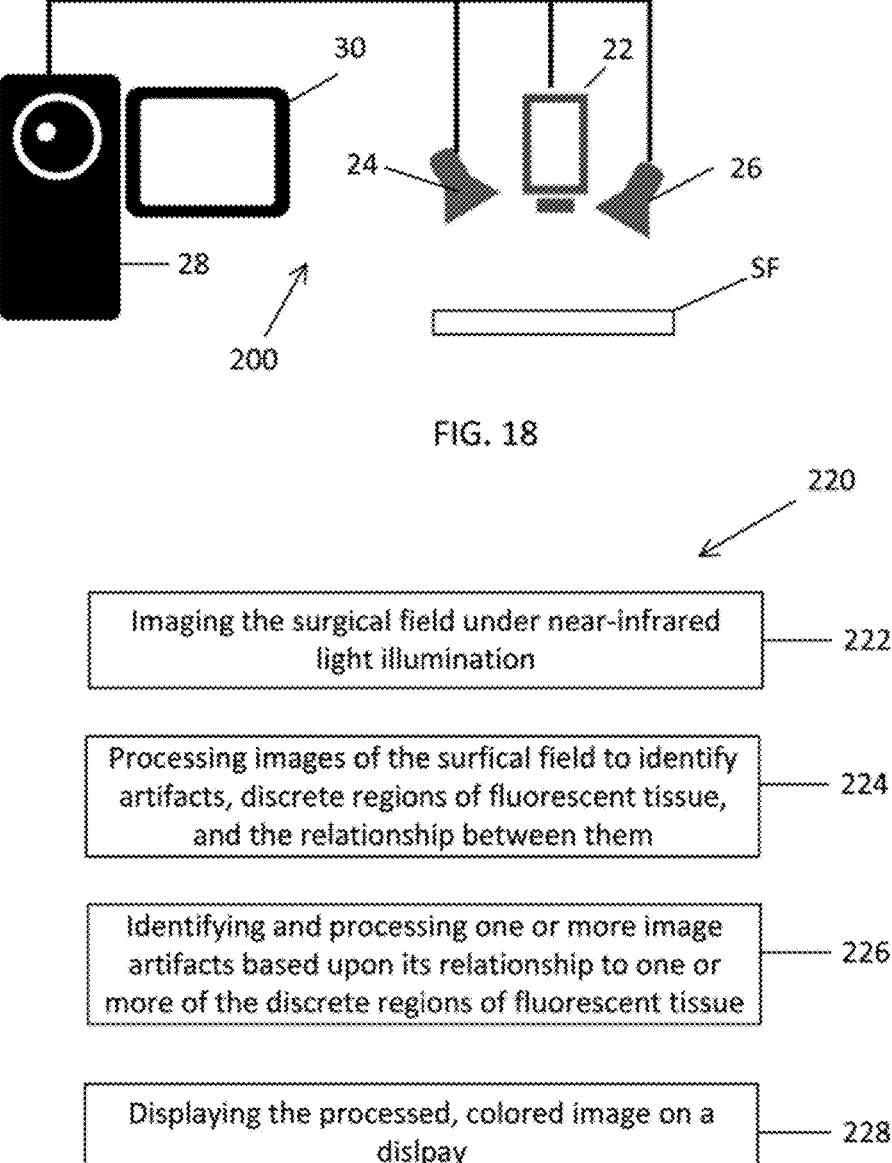

FIG. 18

| Imaging the surgical field under near-infrared light illumination | 222 |

| Processing images of the surfical field to identify artifacts, discrete regions of fluorescent tissue, and the relationship between them | 224 |

| Identifying and processing one or more image artifacts based upon its relationship to one or more of the discrete regions of fluorescent tissue | 226 |

| Displaying the processed, colored image on a dislpay | 228 |

FIG. 19

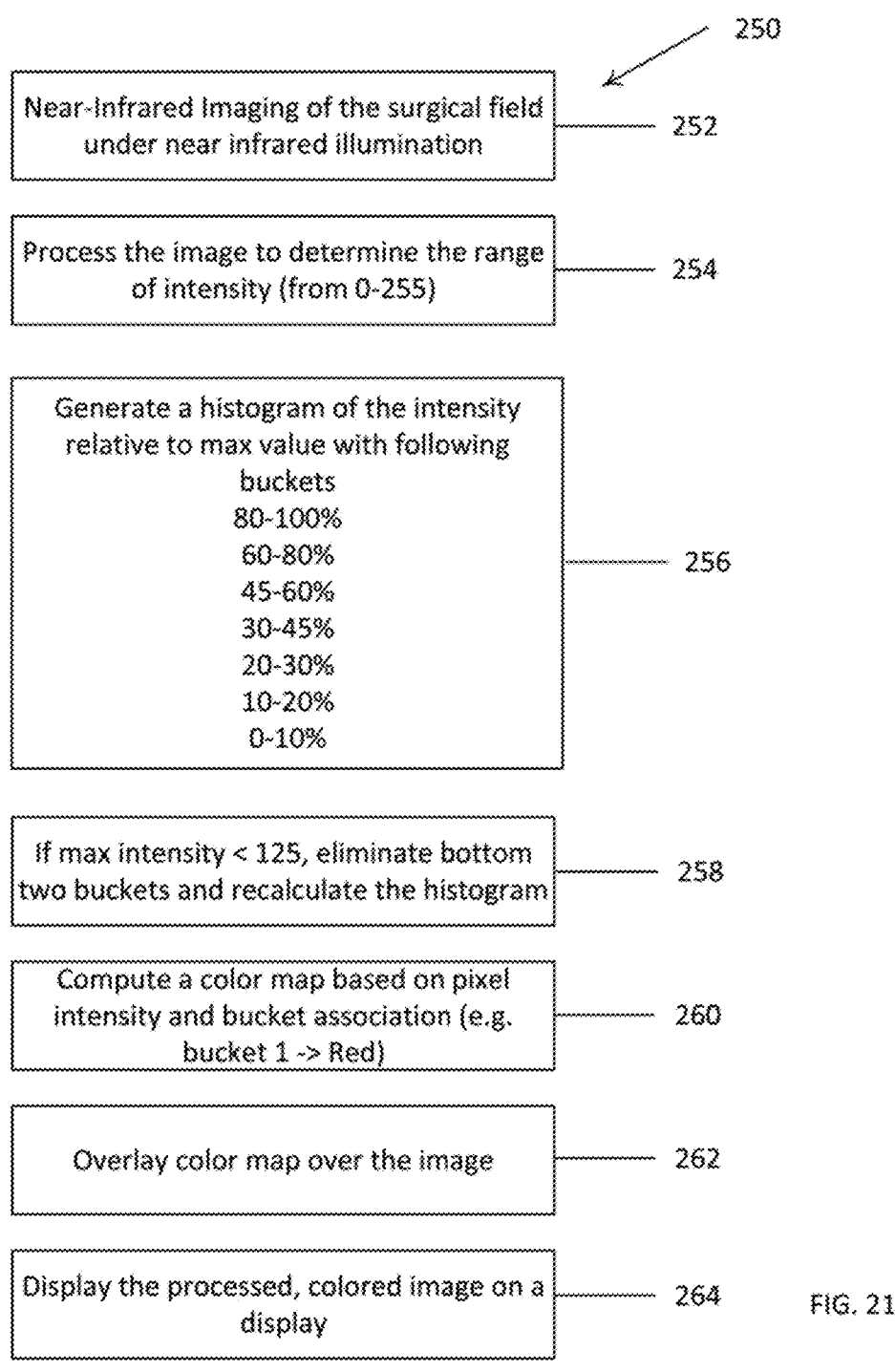

250

Near-Infrared Imaging of the surgical field under near infrared illumination —— 252

Process the image to determine the range of intensity (from 0-255) —— 254

Generate a histogram of the intensity relative to max value with following buckets
80-100%
60-80%
45-60%
30-45%
20-30%
10-20%
0-10%
—— 256

If max intensity < 125, eliminate bottom two buckets and recalculate the histogram —— 258

Compute a color map based on pixel intensity and bucket association (e.g. bucket 1 -> Red) —— 260

Overlay color map over the image —— 262

Display the processed, colored image on a display —— 264

FIG. 21

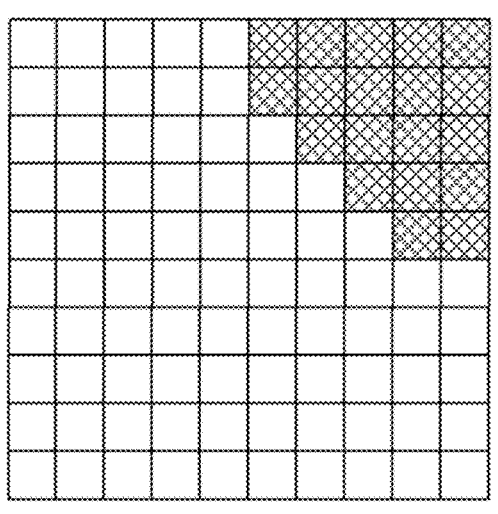
FIG. 22A
Fluorescing Tissue              FIG. 22B
Fluorescing Tissue
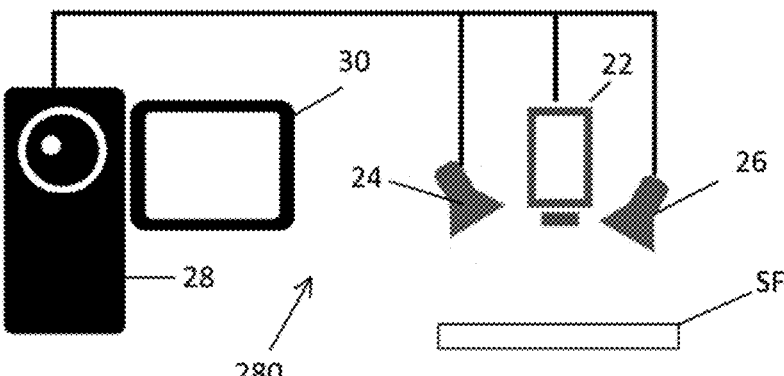
FIG. 23
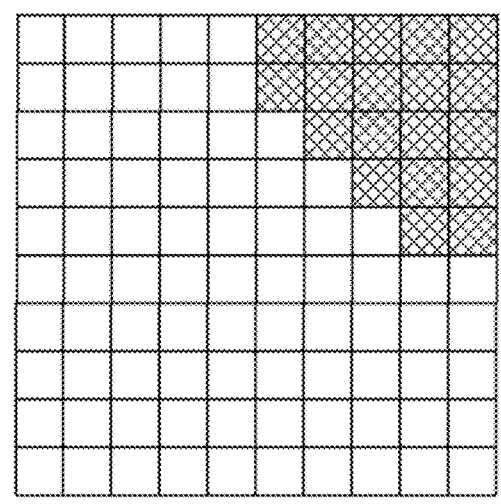
Fluorescing Tissue    FIG. 24A
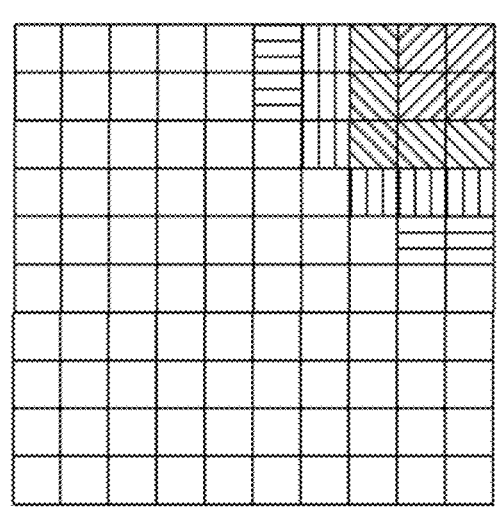
FIG. 24B

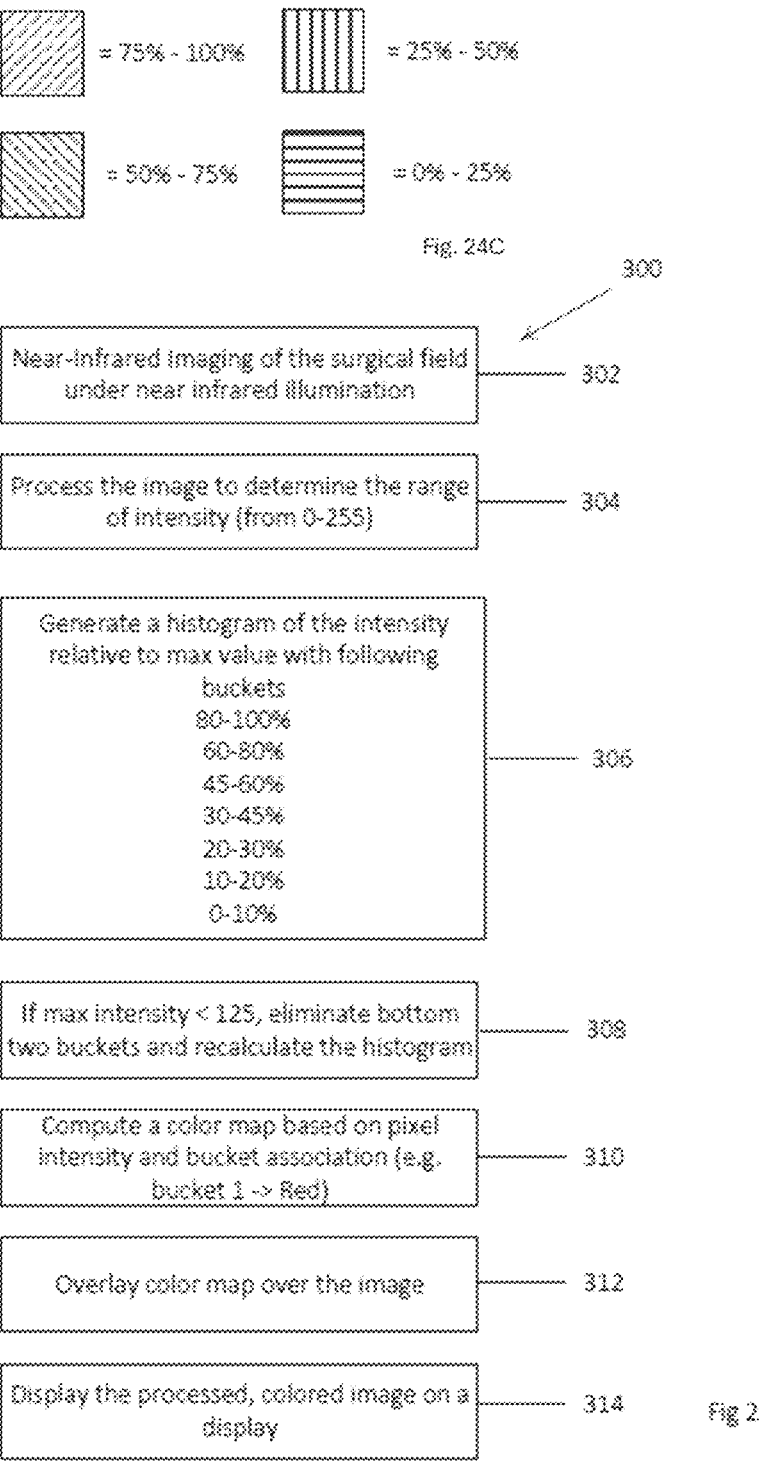

Near-infrared imaging of the surgical field under near infrared illumination — 302

Process the image to determine the range of intensity (from 0-255) — 304

Generate a histogram of the intensity relative to max value with following buckets
80-100%
60-80%
45-60%
30-45%
20-30%
10-20%
0-10%
— 306

If max intensity < 125, eliminate bottom two buckets and recalculate the histogram — 308

Compute a color map based on pixel intensity and bucket association (e.g. bucket 1 -> Red) — 310

Overlay color map over the image — 312

Display the processed, colored image on a display — 314

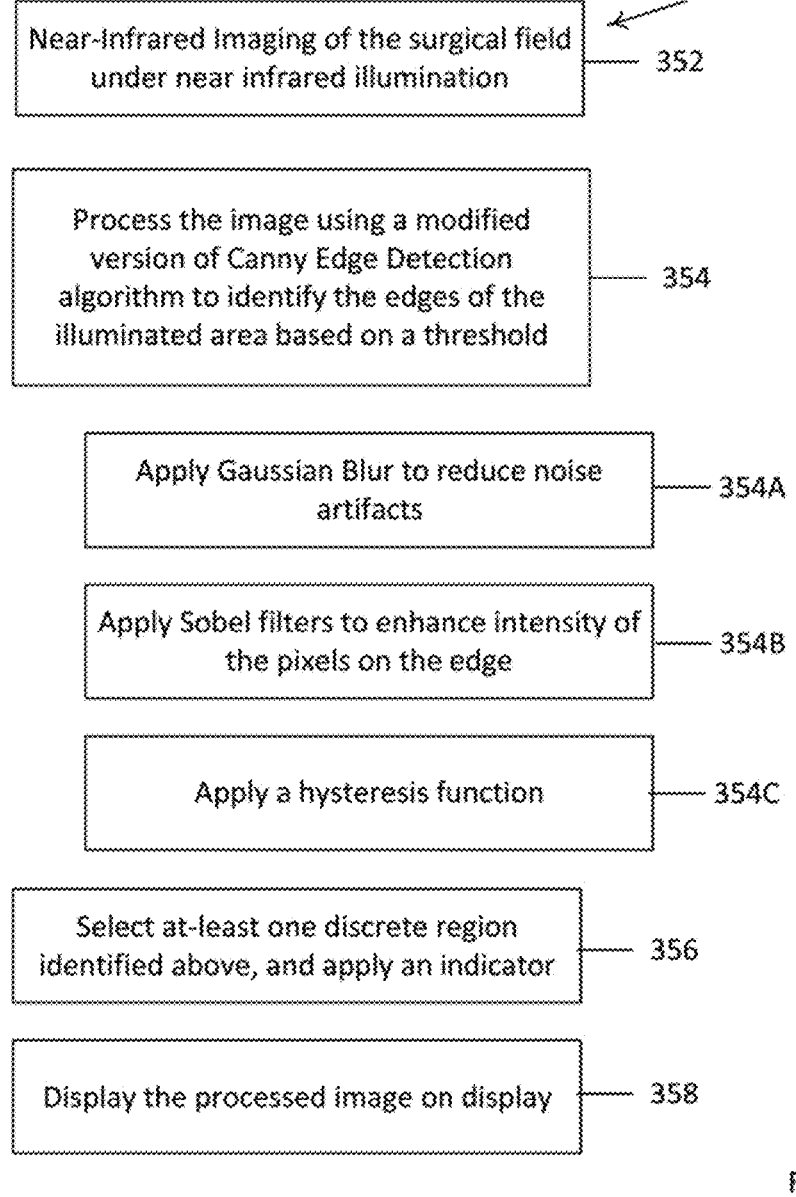

350

Near-infrared imaging of the surgical field under near infrared illumination — 352

Process the image using a modified version of Canny Edge Detection algorithm to identify the edges of the illuminated area based on a threshold — 354

Apply Gaussian Blur to reduce noise artifacts — 354A

Apply Sobel filters to enhance intensity of the pixels on the edge — 354B

Apply a hysteresis function — 354C

Select at-least one discrete region identified above, and apply an indicator — 356

Display the processed image on display — 358

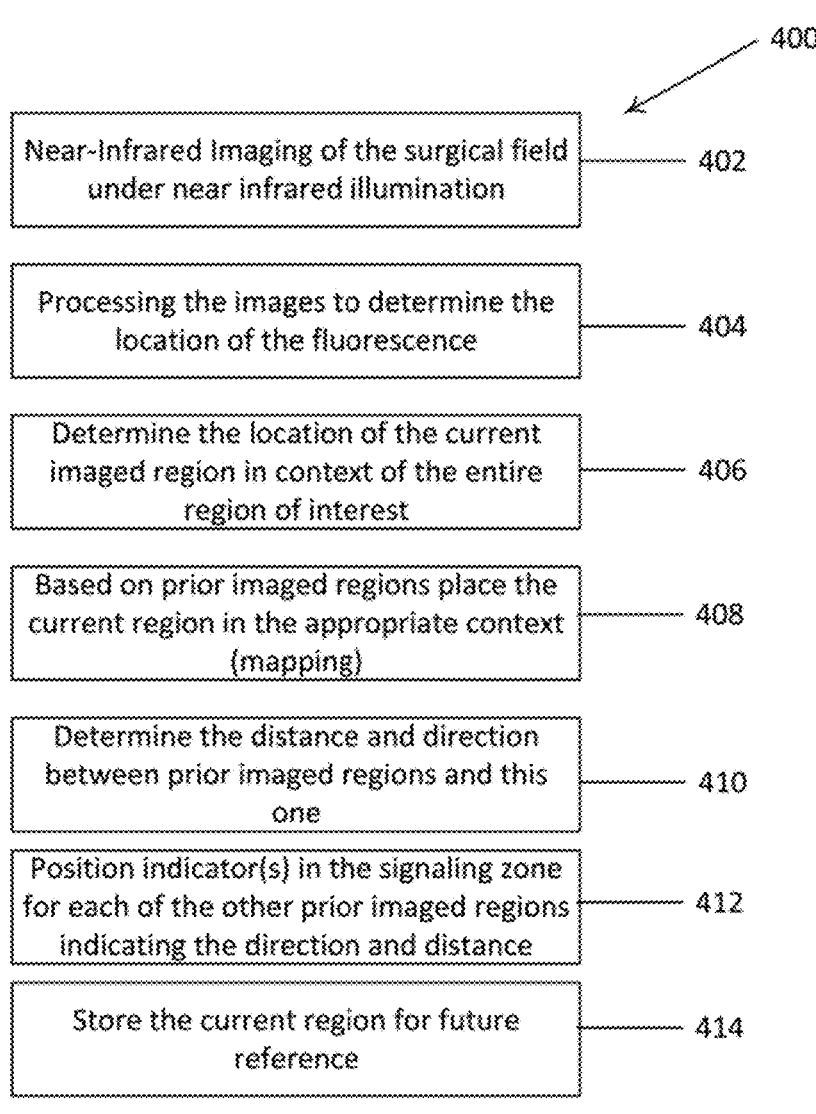

400

Near-Infrared Imaging of the surgical field under near infrared illumination — 402

Processing the images to determine the location of the fluorescence — 404

Determine the location of the current imaged region in context of the entire region of interest — 406

Based on prior imaged regions place the current region in the appropriate context (mapping) — 408

Determine the distance and direction between prior imaged regions and this one — 410

Position indicator(s) in the signaling zone for each of the other prior imaged regions indicating the direction and distance — 412

Store the current region for future reference — 414

FIG. 43

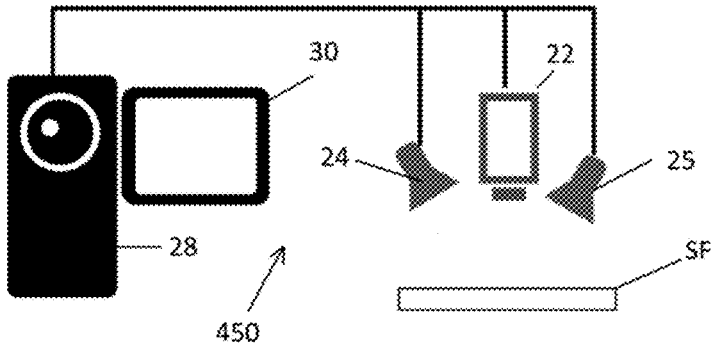
FIG. 44
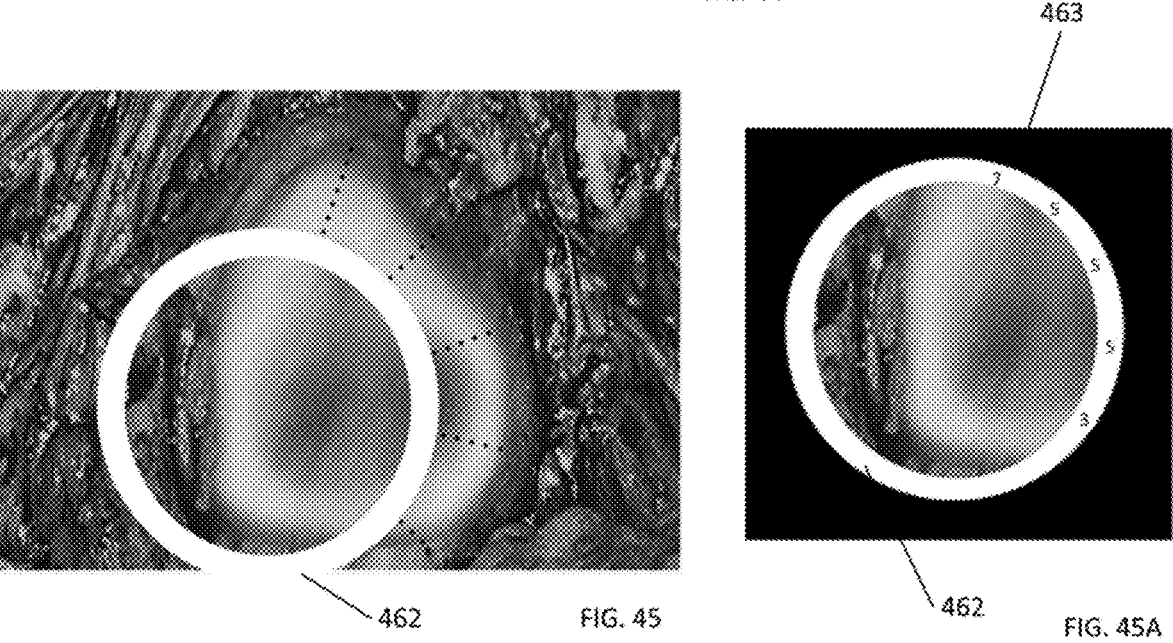
FIG. 45
FIG. 45A

464

462

465

463

512

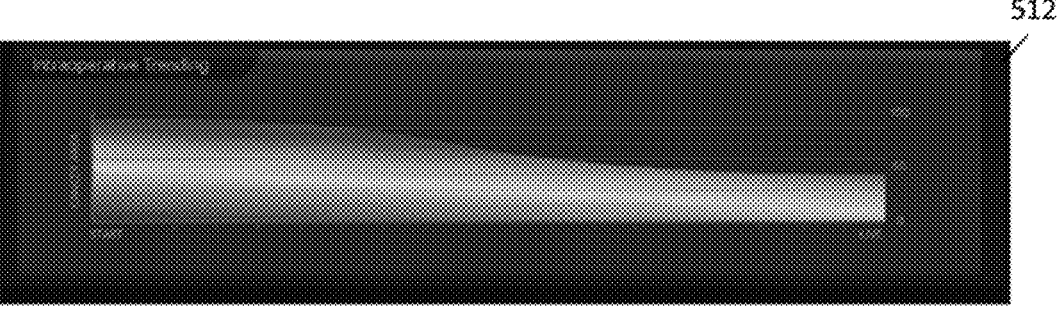

Near-infrared imaging of the surgical field under near infrared illumination

524

Processing the images and determine a fluoresic index that indicates the amount of fluorescence in surgical field

526

Determine the location of the current imaged region in context of the entire region of interest

528

If the current location was processed before, update its fluoresic index

530

Store the current region and its fluoresic index for future reference

532

At regular time intervals, calculate the overall fluoresic index based on all processed regions so far

534

Display a geometric shape whose area is proportional to the total fluoresic index on a timeline

FIG. 53

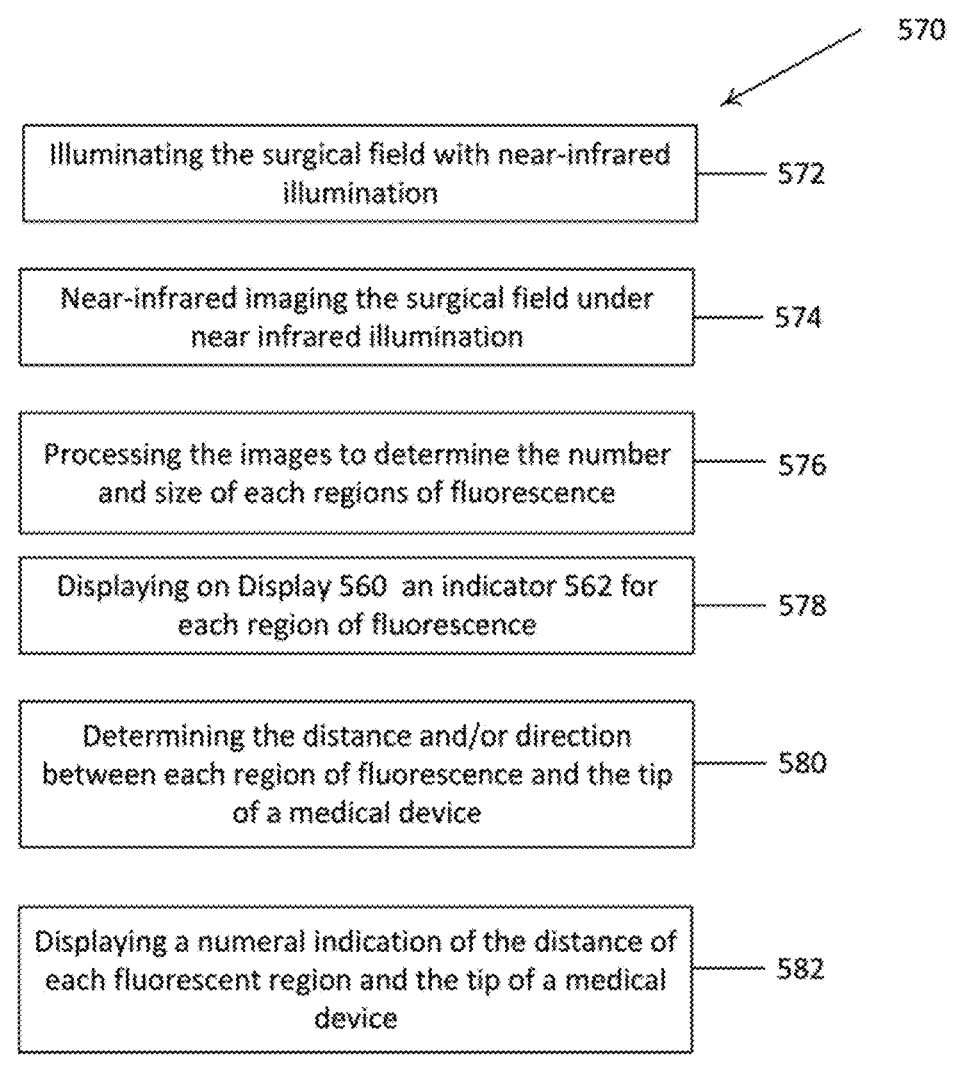

570

Illuminating the surgical field with near-infrared illumination ——— 572

Near-infrared imaging the surgical field under near infrared illumination ——— 574

Processing the images to determine the number and size of each regions of fluorescence ——— 576

Displaying on Display 560 an indicator 562 for each region of fluorescence ——— 578

Determining the distance and/or direction between each region of fluorescence and the tip of a medical device ——— 580

Displaying a numeral indication of the distance of each fluorescent region and the tip of a medical device ——— 582

FIG. 57

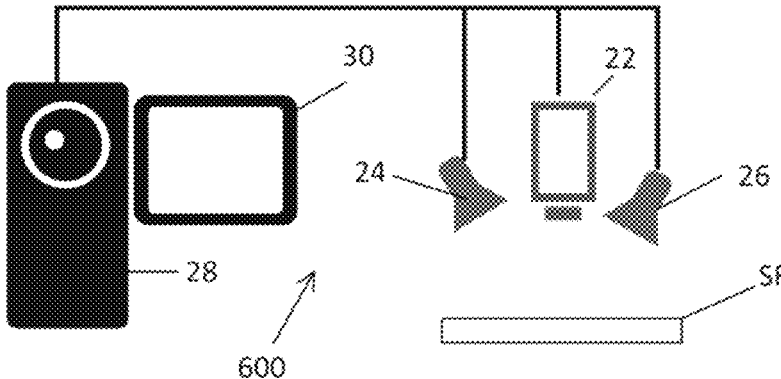
FIG. 58
630
632
Illuminating the surgical field with near-infrared illumination
634
Near-infrared imaging the surgical field under near infrared illumination
636
Updating portions of the image of the surgical field as portions of the fluorescent regions are removed
638
Superimposing on an image of the surgical field, an image of a medical device
FIG. 59
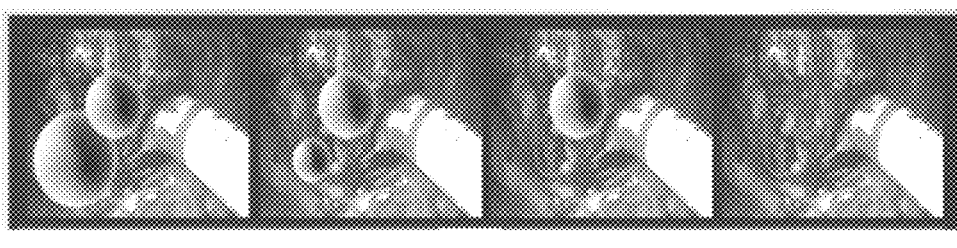
FIG. 60A          FIG. 60B          FIG. 60C          FIG. 60D

SYSTEM AND METHOD FOR DATA VISUALIZATION AND USER INTERFACES OF FLUORESCENTLY TAGGED TISSUE IN A SURGICAL FIELD

FIELD

This disclosure relates to the data visualization and user interfaces of fluorescently tagged tissue in surgical fields including but not limited to open, laparoscopic, endoscopic, and microscopic procedures, whether manual or robotic.

BACKGROUND

Despite major advances in healthcare over the decades, surgeons and interventionalists are often limited in their ability to visualize the underlying condition of tissue throughout the human anatomy. Industry has attempted to offer improvements by guiding procedures with fluorescence imaging of the blood flow using an Indocyanine Green (ICG) agent. This provides clinicians with an ability to differentiate blood vessels from tissue and observe highly vascular areas often indicative of cancer, however, it does not highlight important tissue conditions such as cancer which is critical to outcome success. Due to this limitation, the detection of cancerous tissue remains predominantly subjective and reliant on the expertise of the healthcare worker.

More recently. Achilefu, et al. patented an agent LS-301 specially designed to target cells that express integrins, such as cancer cells, via fluorescence paving the way for surgeons to literally see cancer for the first time. See U.S. Pat. No. 10,806,804, the entirety of which is incorporated herein by reference. This allows detection of the primary tumor, tumor margins and metastatic lymph nodes with a fluorescent detector in an operating room device, endoscope, laparoscope or robotic instrument. While significant progress has been made in developing this emerging imaging agent technology, major improvements are still necessary to provide an optimized data visualization resulting from the fluorescent detector to deliver an enhanced workflow user interface and the tools to support these procedures.

Fluorescence imaging is the visualization of fluorescent molecules as labels for molecular processes or structures. It enables a wide range of observations including the location and dynamics of gene expression, protein expression and molecular interactions in cells and tissues. Near-infrared (NIR) fluorescence light has been utilized in clinical imaging by providing surgeons with highly specific images of target tissue. However, NIR imaging technology has been slow to gain broad acceptance for clinical use mostly due to the lack of available agents such as LS-301, the lack of optimal systems and methods for visualization, and poor user interfaces to support the surgeon's clinical workflow.

The current state of the art in Fluorescence Image-Guided Surgery (FIGS) is based upon visualization systems and methods for user interfaces established to display the ICG agent which is designed to highlight blood instead of actual tissue. The detection of the blood vessels requires only simple software processing and display which has resulted in a very basic monochromatic view overlay often shown in a green color. More recently, with the important advances in the treatment of cancers based upon compounds such as LS-301, cancerous tissue can be tagged and identified by fluorescence requiring new systems and methods to improve the surgeon's ability to see fluorescently tagged tissue. The LS-301 agent offers a strategy to visualize cancer cells throughout tissue, while it is important to display the detailed morphology leveraging new software processing capabilities which can enable precision color mapping to carefully designate the cancer margins, full spectrum visualization highlighting the intensity of cancer cells, among many other clinically useful guidance. Functional visualization of LS-301 tagged tissue has been achieved with purpose-built goggles. See, U.S. Pat. No. 10,652,527, the entirety of which is incorporated by reference. However, improvements are needed to optimally present a systems and methods of visualization for user interfaces with the more modern fluorescence agents including LS-301. This requires that new modern embodiments of systems and methods be invented to truly empower surgeons in the most effective way offering precision 2D or even 3D data visualizations presented throughout optimized user interfaces with the tools even combining an array of other imaging modalities via co-registration techniques to guide surgeons pre-operatively, intra-operatively, and post-operatively.

This disclosure relates to systems and methods for improving the data visualizations and users interfaces of fluorescently tagged tissue including visualization of tissues that fluoresce outside the visible spectrum such as those highlighted by LS301 in cancer cells.

SUMMARY

The various embodiments of this present disclosure provide systems and methods to solve some of the technical problems and clinical limitations of surgeons seeing and treating fluorescently tagged tissue.

According to a first such embodiment for improving the precision of the color mapping, a system and method for the elimination of artifacts due to ambient light for visualizing a surgical field containing a plurality of discrete regions of fluorescing tissue responsive to near-infrared illumination is provided. Generally, a system is provided for real-time visualization of a surgical field containing a plurality of discrete regions of fluorescing tissue responsive to near-infrared illumination. The system preferably comprises a source of near-infrared illumination. At least one imaging camera is provided for imaging a portion of the surgical field. At least one processor is provided for processing image data from at least one camera to reduce artifacts in the images resulting from ambient lighting. At least one processor can differentially process images of the surgical field when the surgical field is illuminated with near-infrared illumination, and when the surgical field is not illuminated by near-infrared illumination to eliminate artifacts from the image not caused by the fluorescence of the tissue such as in the form of standard fluorescent room lighting commonly affecting these procedures. At least one processor can also apply color to the images to indicate the intensity of fluorescence of the discrete regions of fluorescing tissue. At least one process can apply color to an area based upon the measured intensity of fluorescence in that area which may be based upon a look up table, or alternatively at least one processor can use an algorithm to apply color to each area based upon the measured intensity of fluorescence in that area. Finally, the system includes a display for visualizing the processed image portion of the surgical field captured by the camera.

A method for improving the precision of the color mapping for further reducing artifacts from ambient light in images of a surgical field containing a plurality of discrete regions of fluorescing tissue responsive to near-infrared illumination can comprise imaging the surgical field under visible light illumination with an NIR-sensitive camera; imaging the surgical field under near-infrared illumination with an NIR-sensitive camera; and differentially processing the images of the surgical field when the surgical field is illuminated with near-infrared illumination; and when the surgical field is not illuminated by near-infrared illumination to eliminate artifacts from the image not caused by the fluorescence of the tissue such as in the form of standard fluorescent room lighting commonly affecting these procedures. The method can further comprise applying color to the differentially processed image to indicate the intensity of fluorescence of the discrete regions of fluorescing tissue; and displaying the colored processed image of the portion of the surgical field captured by the camera.

According to a second such embodiment for improving the precision of the color mapping, a system and method for eliminating artifacts from reflections for visualizing a surgical field containing a plurality of discrete regions of fluorescing tissue responsive to near infrared illumination, is provided.

The system preferably comprises a source of near-infrared illumination and an imaging camera for imaging a portion of the surgical field. At least one processor processes the data from the camera to reduce artifacts in the images resulting from reflections by identifying areas of suspected reflection in images of the surgical field under white light images; and filtering near infrared light from the identified areas of suspected reflection in images of the surgical field under near-infrared radiation to eliminate possible reflected near-infrared fluorescence from the image of the surgical field. The one or more processors can also apply color to the images to indicate the intensity of fluorescence of the discrete regions of fluorescing tissue. At least one processor can apply color to areas based upon the measured intensity of fluorescence which may be based upon a look up table, or alternatively, at least one processor can use an algorithm to apply color to areas based upon the measured intensity of fluorescence. The system preferably also includes a display for visualizing the processed image of the portion of the surgical field captured by the camera.

A method for improving the precision of the color mapping by reducing artifacts from reflections in images of a surgical field containing a plurality of discrete regions of fluorescing tissue responsive to near-infrared illumination comprises the steps of imaging the surgical field under white light; identifying areas of suspected reflection in images of the surgical field under white light images; and imaging the surgical field under near-infrared illumination. Then, filtering the near-infrared light from the identified areas of suspected reflection in images of the surgical field under near-infrared radiation to eliminate possible reflected near infrared fluorescence from the image of the surgical field. Finally, color can preferably be applied to the filtered images to indicate the intensity of fluorescence of the discrete regions of fluorescing tissue. Lastly, the colored processed image of the portion of the surgical field captured by the camera can be displayed. The color can be applied by referencing a look-up table up table to apply color to an area based upon the measured intensity of fluorescence in that area, or alternatively, by using an algorithm to apply color to the image comprising each area based upon the measured intensity of fluorescence in that area.

In a first alternate construction of the second embodiment, the system can comprise a source of near-infrared illumination and an imaging camera for imaging a portion of the surgical field. One or more processors for processing image data from the camera to reduce artifacts in the images resulting from reflections, tracking the locations of potential reflections over multiple images, and filtering from the images the potential reflections that do not appear in all images. There are preferably also one or more processors for applying color to the filtered images to indicate the intensity of fluorescence of the discrete regions of fluorescing tissue. At least one processor can use a look-up table to apply color to areas based upon the measured intensity of fluorescence, or alternatively, at least one processor can use an algorithm to apply color to areas based upon the measured intensity of fluorescence. There is preferably a display for visualizing the processed image of the portion of the surgical field captured by the camera.

In a second alternate construction of the second embodiment, the system can comprise a source of near-infrared illumination and an imaging camera for imaging a portion of the surgical field. The system further includes one or more processors for processing image data from the camera to reduce artifacts in the images resulting from reflections, by identifying areas of suspected reflection in images of the surgical field under white light images; and filtering near infrared light from the identified areas of suspected reflection in images of the surgical field under near-infrared radiation to eliminate possible reflected near infrared fluorescence from the image of the surgical field. The one or more processors can also apply color to the images to indicate the intensity of fluorescence of the discrete regions of fluorescing tissue. At least one processor can use a look-up table to apply color to areas based upon the measured intensity of fluorescence, or alternatively, at least one processor can use an algorithm to apply color to areas based upon the measured intensity of fluorescence. The system preferably also includes a display for visualizing the processed image of the portion of the surgical field captured by the camera.

In a third alternate construction of the second embodiment, the system can contain a source of near-infrared illumination and an imaging camera for imaging a portion of the surgical field. The system further includes one or more processors for processing image data from the camera to reduce artifacts in the images resulting from reflections, the tracking the locations of potential reflections over multiple images, and filtering from the images the potential reflections that do not appear in all images. The one or more processors can also apply color to the images to indicate the intensity of fluorescence of the discrete regions of fluorescing tissue. At least one processor can use a look-up table to apply color to areas based upon the measured intensity of fluorescence, or alternatively, at least one processor can use an algorithm to apply color to areas based upon the measured intensity of fluorescence. The system preferably also includes a display for visualizing the processed image of the portion of the surgical field captured by the camera.

A method for or improving the precision of the color mapping by reducing artifacts from reflections in images of a surgical field containing a plurality of discrete regions of fluorescing tissue responsive to near infrared illumination comprises imaging the surgical field under near-infrared illumination to obtain a plurality of different images, and processing the image data from the plurality of images to track the locations of potential reflections over the multiple images, and filtering from images the potential reflections that do not appear in all images. The method further comprises applying color to the filtered images to indicate the intensity of fluorescence of the discrete regions of fluorescing tissue; and preferably displaying the processed image of the portion of the surgical field captured by the camera. The color can be applied by referencing a look-up table up table to apply color to an area based upon the measured intensity of fluorescence in that area, or alternatively, by using an algorithm to apply color to the image comprising each area based upon the measured intensity of fluorescence in that area.

According to a third embodiment, a system and method for improving image resolution from a surgical field containing a plurality of discrete regions of fluorescing tissue responsive to near infrared illumination is provided.

The system preferably comprises a source of near-infrared illumination and an imaging camera for imaging a portion of the surgical field. The system preferably also includes one or more processors for processing image data from multiple images of the surgical field at multiple different positions; combining the images using fluorescent features in the image such as margins to align and combine the multiple images into a higher resolution image than any of the original images. The one or more processors can also apply color to the images to indicate the intensity of fluorescence of the discrete regions of fluorescing tissue. At least one processor can use a look-up table to apply color to areas based upon the measured intensity of fluorescence, or alternatively, at least one processor can use an algorithm to apply color to areas based upon the measured intensity of fluorescence. The system preferably also includes a display for visualizing the processed image of the portion of the surgical field captured by the camera.

The method preferably comprises imaging a portion of the surgical field, and processing image data from multiple images of the surgical field at multiple different positions, combining the images using fluorescent features in the image to align and combine the multiple images into a higher resolution image than any of the original images. The images could be combined using a weighted averaging whereby the nearest images in time are weighted higher than the preceding average images which can improve the perceived latency of the real-time view for the healthcare worker. The method preferably further includes applying color to the images to indicate the intensity of fluorescence of the discrete regions of fluorescing tissue and displaying the processed image of the portion of the surgical field captured by the camera. The color can be applied by referencing a look-up table up table to apply color to an area based upon the measured intensity of fluorescence in that area, or alternatively, by using an algorithm to apply color to the image comprising each area based upon the measured intensity of fluorescence in that area.

According to a fourth embodiment, a system and method for identifying abnormal tissue in a surgical field containing a plurality of discrete regions of fluorescing tissue responsive to near infrared illumination is provided.

The system comprises a source of near-infrared illumination and an imaging camera for imaging a portion of the surgical field. The system further comprises one or more processors for processing the images from the camera to detect very small spots of cancerous tissue which may be considered abnormal tissue by comparing portions of the surgical field with a library of images from abnormal tissues. The one or more processors can also apply color to the images to indicate the detected abnormal tissue. The system preferably has a user interface including a display for displaying the processed image of the portion of the surgical field captured by the camera. The one or more processors can use a look-up table to apply color to areas based upon the abnormal tissue identified, or they can use an algorithm to apply color to areas based upon the abnormal tissue identified.

The method preferably comprises the steps of imaging a portion of the surgical field under near-infrared illumination and processing the images to detect small spots of cancerous tissue or abnormal tissue adjacent areas of fluorescence by comparing portions of the image of the surgical field with a library of images from abnormal tissues. The method can further comprise the step of applying color to the images to indicate the detected abnormal tissue; and displaying the colored processed image of the portion of the surgical field captured by the camera. The step of applying color to the images can be done by referencing a look-up table up table to apply color to an area or using an algorithm to apply color to the image comprising each area.

According to a fifth embodiment, a system and method for identifying fluids in a surgical field containing a plurality of discrete regions of fluorescing tissue responsive to near infrared illumination is provided.

The system preferably comprises one or more sources of light of at least two discrete wavelengths, and an imaging camera for imaging a portion of the surgical field under each of at least two wavelengths. The system preferably also includes one or more processors for processing images of the surgical field under light from at least two discrete wavelengths to detect fluids. The one or more processors may also apply color to the images to indicate the location of fluid. The processors can use a look-up table to apply color to areas based upon the probability of having liquid, or the processors can use an algorithm to apply color to areas based upon the probability of having liquid.

The method preferably includes the step of imaging a portion of the surgical field under illumination from at least two wavelengths. The method preferably further processes images of the surgical field under light from at least two discrete wavelengths to detect fluids. Finally, the method can include the step of applying color to the images to indicate the location of fluid. The color can be applied using a look-up table to apply color to areas based upon the probability of having liquid or using an algorithm to apply color to areas based upon the probability of having liquid.

According to a sixth embodiment, a system and method for tracking artifacts using fluorescent landmarks in a surgical field containing a plurality of discrete regions of fluorescing tissue responsive to near infrared illumination is provided.

The system comprises a source of near-infrared illumination and an imaging camera for imaging a portion of the surgical field, and a processor for processing image data from the camera to identify artifacts in the image in relation to the discrete regions of fluorescing tissue. The processor preferably further removes the artifacts from the images, or otherwise prevents these artifacts from being displayed as fluorescing tissue. The system preferably further comprises a display for visualizing the processed image of the portion of the surgical field captured by the camera.

The method comprises imaging a portion of the surgical field and processing image data from the camera to identify artifacts in the image in relation to the discrete regions of fluorescing tissue. The method preferably further comprises identifying artifacts in subsequent images by their relationship to the discrete regions of fluorescing tissue, and removing the artifacts from the image, or otherwise preventing the artifacts from being displayed as fluorescing tissue. The processed image is then displayed on a user interface, including a display. The artifacts may be replaced by averaging or placing the data from preceding images in place of the portions containing detected artifacts within the current image among other techniques.

According to a seventh embodiment, a system and method for identifying fluorescent tissue in a surgical field containing a plurality of discrete regions of fluorescing tissue responsive to near infrared illumination is provided.

The system comprises a source of near-infrared illumination and an imaging camera for imaging a portion of the surgical field. The system preferably comprises at least one for processing image data of the surgical field and for applying color to the images to indicate the intensity of fluorescence of the discrete regions of fluorescing tissue. At least one processor can use a look-up table to apply color to areas based upon the measured intensity of fluorescence, or alternatively, at least one processor can use an algorithm to apply color to areas based upon the measured intensity of fluorescence. At least one processor scales the measured intensities of fluorescence based upon the maximum measured fluorescence intensity in the image in a predetermined minimum area of the image. The system preferably also includes a display for visualizing the processed image of the portion of the surgical field captured by the camera.

In a first alternate of the seventh embodiment, at least one processor dynamically rescales the measured intensities of fluorescence and the maximum measured fluorescence intensity changes. In a second alternative of the seventh embodiment, at least one processor rescales the measured intensities of fluorescence upon a predetermined change in the maximum measured fluorescence. In a third alternative of the seventh embodiment, at least one processor rescales the measured intensities of fluorescence upon a predetermined change in the average measured intensity of the fluorescence of the surgical field.

The method comprises illuminating the surgical field with near-infrared light, and imaging at least a portion of the surgical field. The image data from the surgical field is processed to apply color to the images to indicate the intensity of fluorescence of the discrete regions of fluorescing tissue. The colored, processed image of the portion of the surgical field captured by the camera is then displayed on a display.

In a first alternate of the seventh embodiment, the measured intensities of fluorescence are dynamically rescaled as the maximum measured fluorescence intensity changes. In a second alternative of the seventh embodiment, the measured intensities of fluorescence are rescaled upon a predetermined change in the maximum measured fluorescence. In a third alternative of the seventh embodiment, the measured intensities of fluorescence are rescaled upon a predetermined change in the average measured intensity of the fluorescence of the surgical field.

According to an eighth embodiment, a system and method of using patterned overlays for identifying fluorescent tissue in a surgical field containing a plurality of discrete regions of fluorescing tissue responsive to near infrared illumination is provided.

The system can comprise a source of near-infrared illumination and an imaging camera for imaging a portion of the surgical field, and at least one processor for processing image data of the surgical field and for applying patterned overlays to the images to indicate the intensity of fluorescence of the discrete regions of fluorescing tissue. The system preferably further comprises a display for visualizing the processed image of the portion of the surgical field captured by the camera.

In a first alternate of the eighth embodiment, the system includes at least one processor that scales the maximum measured fluorescence intensity in the image in a predetermined minimum area of the image and is assigned patterned overlays based on a look-up table of the scaled values of intensities or is based upon an algorithm. In a second alternate of the eighth embodiment, the system includes at least one processor that dynamically rescales the measured intensities of fluorescence as the maximum measured fluorescence intensity changes. In a third alternate of the eighth embodiment, the system includes at least one processor that rescales the measured intensities of fluorescence upon a predetermined change in the maximum measured fluorescence. In a fourth alternate of the eighth Embodiment, the system includes at least one processor that rescales the measured intensities of fluorescence which are rescaled upon a predetermined change in the average measured intensity of the fluorescence of the surgical field.

The method can comprise the steps of imaging a portion of the surgical field, and processing image data of the surgical field and applying patterned overlays to the images to indicate the intensity of fluorescence of the discrete regions of fluorescing tissue. The method preferably also includes displaying the processed image of the portion of the surgical field captured by the camera.

In a first alternate of the eighth embodiment, the method includes scaling the maximum measured fluorescence intensity in the image in a predetermined minimum area of the image, and assigning patterned overlays based on a look-up table of the scaled values of intensities or based upon an algorithm. In a second alternate of the eighth embodiment, the method includes dynamically rescaling the measured intensities of fluorescence as the maximum measured fluorescence intensity changes. In a third alternate of the eighth embodiment, the method includes rescaling the measured intensities of fluorescence upon a predetermined change in the maximum measured fluorescence. In a fourth alternate of the eighth embodiment, the method includes rescaling the measured intensities of fluorescence are rescaled upon a predetermined change in the average measured intensity of the fluorescence of the surgical field.

According to a ninth embodiment, a system and method of superimposing graphic indicators for applying markings on fluorescent tissue images of a surgical field containing a plurality of discrete regions of fluorescing tissue responsive to near infrared illumination is provided.

The system comprises a source of near-infrared illumination and an imaging camera for imaging a portion of the surgical field and a display for visualizing an image of the portion of the surgical field captured by the camera. The system further comprises at least one processor for identifying at least one of the discrete regions of fluorescing tissue in the image and superimposing one or more graphic indicators on the displayed image to identify at least one of the discrete regions of fluorescing tissue. The graphic indicator may appear as an overlay with full opacity on a surgical image, as an overlay with transparency on a surgical image, or alone without a surgical image. The graphic indicator maintains its position relative to the tissue even in real-time using a detected anatomical position identified from the fluorescence of the tissue such as through the appearance of margins.

In a first alternative of the ninth embodiment, the indicator is an arrow, pointing to the discrete regions of fluorescing tissue and/or non-cancerous anatomy to be avoided. In a second alternative of the ninth embodiment, the indicator is a circle surrounding a discrete region of fluorescing tissue or non-cancerous anatomy to be avoided. At least one processor can size the circle to include multiple discrete regions of fluorescing tissue that are within a predetermined distance from each other. In a third alternative of the ninth embodiment, the indicator is a boundary line closely conforming to the edges of the discrete region of fluorescing tissue and/or non-cancerous anatomy to be avoided, preferably with a predetermined minimum radius of curvature. In this third alternative, the system can include a control for adjusting the predetermined minimum radius of curvature. At least one processor can size the boundary line to include within its boundary multiple discrete regions of fluorescing tissue that are within a predetermined distance from each other (so as to guide a surgical resection a standard distance (e.g., in physical distance-such as inches or mm or image distance-such as pixels, etc.) from the detected cancer margins.

In a fourth alternative of the ninth embodiment, the processor not only displays a boundary line on the image of the surgical field, but further displays a peripheral line spaced outside of the boundary line a predetermined distance which does not block the cancerous margins and offers a resection line to guide surgeons. The distance(s) can be determined by the area of the discrete region of fluorescing tissue, by the intensity of the discrete region of fluorescing tissue, by the average intensity of the discrete region of fluorescing tissue, by the maximum intensity of the discrete region of fluorescing tissue, by the density of fluorescent areas, or some other criteria. The boundary line(s) correspond to the edges of cancerous tissue, and the peripheral lines can serve as a guide to a surgeon.

In a fifth alternative of the ninth embodiment, the indicator is a polygon surrounding a discrete region of fluorescing tissue and/or non-cancerous anatomy to be avoided. At least one processor can size the polygon to include just one or multiple discrete regions of fluorescing tissue that are within a predetermined distance from each other. At least one processor can change the appearance of the polygon over time by, for example, making it flash, fade in and out, rotate, increase in size, or decrease in size. The changing appearance of the polygon can serve as a better attentional guide to the surgeon.

The method comprises near-infrared imaging a portion of the surgical field and displaying an image of the portion of the surgical field captured by the camera. The method can further comprise processing the image of the surgical field to identify at least one of the discrete regions of fluorescing tissue in the image and superimposing one or more indicators on the displayed image to identify at least one of the discrete regions of fluorescing tissue.

In a first alternative of the ninth embodiment, the indicator is an arrow, pointing to the discrete regions of fluorescing tissue. In a second alternative of the ninth embodiment, the indicator is a circle surrounding a discrete region of fluorescing tissue. At least one processor can size the circle to include multiple discrete regions of fluorescing tissue that are within a predetermined distance from each other. In a third alternative of the ninth embodiment, the indicator is a boundary line closely conforming to the edges of the discrete region of fluorescing tissue, preferably with a predetermined minimum radius of curvature. In this third alternative, the system can include a control for adjusting the predetermined minimum radius of curvature. At least one processor can size the boundary line to include multiple discrete regions of fluorescing tissue that are within a predetermined distance from each other.

In a fourth alternative of the ninth embodiment, the processor not only displays one or more boundary lines on the image of the surgical field, but further displays a peripheral line spaced outside of the boundary line a predetermined distance. This predetermined distance can be determined by the area of the discrete region of fluorescing tissue, by the intensity of the discrete region of fluorescing tissue, by the average intensity of the discrete region of fluorescing tissue, by the maximum intensity of the discrete region of fluorescing tissue, by the density of fluorescent areas, or some other criteria. The boundary line(s) could correspond to the edges of cancerous tissue as a guide to a surgeon.

In a fifth alternative of the ninth embodiment, the indicator is a polygon surrounding a discrete region of fluorescing tissue and/or non-cancerous anatomy to be avoided. At least one processor can size the polygon to include just one or multiple discrete regions of fluorescing tissue that are within a predetermined distance from each other. At least one processor can change the appearance of the polygon over time by, for example, making it flash, fade in and out, rotate, increase in size, or decrease in size. The changing appearance of the polygon can serve as a better attentional guide to the surgeon.

According to a tenth embodiment, a system and method of superimposing a signaling zone on or around an image of a surgical field containing a plurality of discrete regions of fluorescing tissue responsive to near infrared illumination is provided.

The signaling zone is a border area at least partially surrounding an image of a portion of a surgical field, providing a space for the display of information about the area outside the displayed image. The display of the signaling zone on or around an image of a surgical field can be turned on or off. When on, the signaling zone can contain indicators that can be graphic, numeric, or text-based that can aid a healthcare worker's understanding of the presence or characteristics of surrounding regions of fluorescence that are not displayed in the portion of a surgical field being currently visualized.

The system can comprise a source of near-infrared (NIR) illumination, a NIR detection camera for imaging a portion of the surgical field, and a display for visualizing an image of the portion of the surgical field captured by the camera. The display can optionally include other information or visualizations in addition to the image of the portion of the surgical field captured by the camera. The system can additionally include a processor for generating a signaling zone on the display at least partially surrounding the image of the portion of the surgical field, and further displaying in this signaling zone an indicator of at least one adjacent discrete region of fluorescing tissue that is outside of the centrally displayed image. Each indicator is preferably located in that portion of the signaling zone closest to the adjacent discrete region of fluorescing tissue that the indicator represents.

In a first alternative to the tenth embodiment, each indicator can be coded to represent the distance between the edge of the image and its respective discrete region. Each indicator can represent distance with the color or color properties (hue, saturation, brightness), shape, size, or width of the indicator, with indicia, with numbers, or with text (ex. letters, abbreviations, words). The indicator can also utilize a combination of the aforementioned features. For instance, the indicator can be an arrow with numbers overlaid, where the arrow is located in the portion of the signaling zone closest to the adjacent discrete region of fluorescing tissue and the number reflects the distance in a unit of measurement between the edge of the image and the fluorescing region.

In a second alternative to the tenth embodiment, each indicator can be coded to represent the intensity of the fluorescence of the tissue in its respective region. Each indicator can represent intensity with the color or color properties (hue, saturation, brightness), shape, size, or width of the indicator, with indicia, with numbers, or with text (ex. letters, abbreviations, words). The indicator can be coded to represent the intensity relatively or via descriptive statistics including but not limited to the average, minimum, maximum, median, or mode of the fluorescence pixel intensities in that fluorescing region. The intensity can be coded to represent the intensity at the center point of each respective region or at the point in each respective region closest to the image.

In a third alternative to the tenth embodiment, each indicator can be coded to represent the size of its respective fluorescing region. Each indicator can represent size with the color or color properties (hue, saturation, brightness), shape, size, or width of the indicator, with indicia, with numbers, or with text (ex. letters, abbreviations, words).

In a fourth alternative to the tenth embodiment, each indicator can be coded to represent the rank order of importance of the tissue in its respective region. The rank order of importance can be based on a combination of the distance, size, or intensity of the adjacent discrete region of fluorescing tissue that is outside of the displayed image. An algorithm can combine the distance, size, and/or intensity data from each adjacent region of fluorescing tissue, assign each region an importance score, and then rank the importance of each region. Each indicator can represent the rank order of importance with the color or color properties (hue, saturation, brightness), shape, size, or width of the indicator, with indicia, with numbers, or with text (ex. letters, abbreviations, words).

The method can comprise imaging a portion of the surgical field with a camera and displaying an image of the portion of the surgical field captured by the camera on a display. The method can further comprise generating a signaling zone on the display at least partially surrounding the image of the portion of the surgical field and displaying in this signaling zone an indicator of at least one adjacent discrete region of fluorescing tissue that is outside of the displayed image. Each indicator is preferably located in that portion of the signaling zone closest to the adjacent discrete region of fluorescing tissue that the indicator represents.

In a first alternative to the tenth embodiment, each indicator can be coded to represent the distance between the edge of the image and its respective discrete region. Each indicator can represent distance with the color or color properties (hue, saturation, brightness), shape, size, or width of the indicator, with indicia, with numbers, or with text (ex. letters, abbreviations, words). The indicator can also utilize a combination of the aforementioned features. For instance, the indicator can be an arrow with numbers overlaid, where the arrow is located in the portion of the signaling zone closest to the adjacent discrete region of fluorescing tissue and the number reflects the distance in a unit of measurement between the edge of the image and the fluorescing region.

In a second alternative to the tenth embodiment, each indicator can be coded to represent the intensity of the fluorescence of the tissue in its respective region. Each indicator can represent intensity with the color or color properties (hue, saturation, brightness), shape, size, or width of the indicator, with indicia, with numbers, or with text (ex. letters, abbreviations, words). The indicator can be coded to represent the intensity relatively or via descriptive statistics including but not limited to the average, minimum, maximum, median, or mode of the fluorescence pixel intensities in that fluorescing region. The intensity can be coded to represent the intensity at the center point of each respective region or at the point in each respective region closest to the image.

In a third alternative to the tenth embodiment, each indicator can be coded to represent the size of its respective fluorescing region. Each indicator can represent size with the color or color properties (hue, saturation, brightness), shape, size, or width of the indicator, with indicia, with numbers, or with text (ex. letters, abbreviations, words).

In a fourth alternative to the tenth embodiment, each indicator can be coded to represent the rank order of importance of the tissue in its respective region. The rank order of importance can be based on a combination of the distance, size, or intensity of the adjacent discrete region of fluorescing tissue that is outside of the displayed image. An algorithm can combine the distance, size, and/or intensity data from each adjacent region of fluorescing tissue, assign each region an importance score, and then rank the importance of each region. Each indicator can represent the rank order of importance with the color or color properties (hue, saturation, brightness), shape, size, or width of the indicator, with indicia, with numbers, or with text (ex. letters, abbreviations, words).

According to an eleventh embodiment, a system and method of superimposing a signaling zone on or around an image of a surgical field containing a plurality of discrete regions of fluorescing tissue responsive to near infrared illumination is provided.

The system can comprise a source of near-infrared illumination and a NIR detection camera for imaging a portion of the surgical field; and a user interface, including a display, for visualizing an image of the portion of the surgical field captured by the camera. The display can optionally include other information or visualizations in addition to the image of the portion of the surgical field captured by the camera. The system can also include at least one processor for generating a signaling zone on the display surrounding the image of the portion of the surgical field, and further displaying in this signaling zone an indicator of at least one adjacent discrete region of fluorescing tissue that is outside of the displayed image. Each indicator can be located in that portion of the signaling zone closest to the adjacent discrete region of fluorescing tissue that the indicator represents. The indicator is preferably color coded to represent the intensity of fluorescence of its respective discrete region.

The image of the surgical field is preferably generally circular, and the signaling zone is a circular ring surrounding the circular image of the surgical field. However, the image of the surgical field is generally rectangular, and the signaling zone could be a rectangular ring surrounding the rectangular image of the surgical field.

The method can comprise imaging a portion of the surgical field with a camera and displaying an image of the portion of the surgical field captured by the camera. The method can further comprise generating a signaling zone on the display surrounding the image of the portion of the surgical field and displaying within this signaling zone an indicator of at least one adjacent discrete region of fluorescing tissue that is outside of the displayed image. Each indicator is preferably located in that portion of the signaling zone closest to the adjacent discrete region of fluorescing tissue that the indicator represents with the indicator being color coded to represent the intensity of fluorescence of its respective discrete region.

The image of the surgical field is preferably generally circular, and the signaling zone is a circular ring surrounding the circular image of the surgical field. However, the image of the surgical field is generally rectangular, and the signaling zone could be a rectangular ring surrounding the rectangular image of the surgical field.

According to a twelfth embodiment, a system and method of indicating the location of off-display boundaries of discrete regions of fluorescing tissue responsive to near infrared illumination is provided.

The system can comprise a source of near-infrared illumination and a NIR detection camera for imaging a portion of the surgical field and a display for visualizing an image of the portion of the surgical field captured by the camera. The display can optionally include other information or visualizations in addition to the image of the portion of the surgical field captured by the camera. The system can further comprise at least one processor for generating a signaling zone on the display at least partially surrounding the image of the portion of the surgical field, and further displaying in this signaling zone an indicator coded to indicate the distance from the edge of the image to the to the edge of the nearest edge of visible fluorescing tissue in the image or nearest edge of a nearby discrete region of fluorescing tissue previously detected in a displayed image extending the surgeons' perspective of cancer even outside their current field of view.

In a first alternative to the twelfth embodiment, the indicator can be colored representing the distance between the edge of the image and the edge of the discrete region. In a second alternative to the twelfth embodiment, the indicator is the width of the signaling zone representing the distance between the edge of the image and the edge of the discrete region. In a third alternative to the twelfth embodiment, the indicator can be a pattern in the signaling zone representing the distance between the edge of the image and the edge of the discrete region. In a fourth alternative to the twelfth embodiment, the indicator can be a numeral in the signaling zone representing the distance between the edge of the image and the edge of the discrete region.

The method can comprise imaging a portion of the surgical field and displaying an image of the portion of the surgical field captured by the camera. The method can further comprise generating a signaling zone on the display at least partially surrounding the image of the portion of the surgical field and displaying in this signaling zone an indicator coded to indicate the distance from the edge of the image to the to the edge of the discrete region of fluorescing tissue that is shown in the displayed image.

In a first alternative to the twelfth embodiment, the indicator can be color representing the distance between the edge of the image and the edge of the discrete region. In a second alternative to the twelfth embodiment, the indicator is the width of the signaling zone representing the distance between the edge of the image and the edge of the discrete region. In a third alternative to the twelfth embodiment, the indicator can be a pattern in the signaling zone representing the distance between the edge of the image and the edge of the discrete region. In a fourth alternative to the twelfth embodiment, the indicator can be a numeral in the signaling zone representing the distance between the edge of the image and the edge of the discrete region.

According to a thirteenth embodiment of a system, a method of indicating the progress of a surgical procedure taking place in a surgical field containing a plurality of discrete regions of fluorescing tissue responsive to near-infrared illumination, is provided.

The system can comprise a processor for determining the total area of fluorescing tissue in the surgical field from an image of the surgical field, and a progress indicator displayed on a display of an image of a portion of the surgical field. The progress indicator preferably comprises a series of similar geometric shapes each of whose area is proportional to the shape and total area of the regions of fluorescing tissue remaining to be removed at a predetermined time interval. The geometric shapes are preferably displayed in an oblique edge view. The geometric shape in the display may be simplified to appear as a circle, square, rectangle, or other regular polygon, while preferably it will appear with the same shape as each fluorescing tissue map morphology.

The method can comprise determining the total area of fluorescing tissue in the surgical field from an image of the surgical field and displaying on a display a progress indicator comprising a series of similar geometric shapes each of whose area is proportional to the total area of the regions of fluorescing tissue remaining to be removed at a predetermined time interval. The geometric shapes are preferably displayed in an oblique edge view. The geometric shape in the display may be simplified to appear as a circle, square, rectangle, or other regular polygon, while preferably it will appear with the same shape as each fluorescing tissue map morphology.

According to a fourteenth embodiment of a system, a method of indicating the progress of a surgical procedure taking place in a surgical field containing a plurality of discrete regions of fluorescing tissue responsive to near-infrared illumination, is provided.

The system comprises a processor for processing images of the surgical field to determine the area of each discrete region of fluorescing tissue in the surgical field and for displaying a progress indicator comprising a plurality of geometric shapes, one representing each discrete region of fluorescing tissue, each of which has an area proportional to the area of one of the discrete regions of fluorescing tissue for indicating the number and size of discrete regions of fluorescing tissue to be removed. The geometric shapes are preferably all circles, but could be some other shape, such as a rectangle or a regular polygon. In some alternative, the shapes are the shapes of the fluorescent areas they represent. The shapes are preferably color coded to indicate the intensity fluorescence of its corresponding discrete regions of fluorescing tissue.

At least one processor can also determine the distance and/or direction of the tip of a medical device in the surgical field to the nearest edge of visible fluorescing tissue or nearest edge of nearby fluorescing tissue discrete regions in each radial direction displaying the distance and/or direction on the display based upon previously detected images guiding the surgeons' perspective of cancer even outside their current field of view.

The processor can also display a numerical value corresponding to the area of each region and or distance of the tip from each region, and/or intensity of fluorescence.

The method comprises processing images of the surgical field to determine the area of each discrete region of fluorescing tissue in the surgical field, and displaying a progress indicator comprising a plurality of geometric shapes, one representing each discrete region of fluorescing tissue, each of which has an area proportional to the area of one of the discrete regions of fluorescing tissue for indicating number and size of discrete regions of fluorescing tissue to be removed. The geometric shapes may be all circles, but could be some other shape, such as a rectangle or a regular polygon. In some alternatives, the shapes are the shapes of the fluorescent area morphology they represent. The shapes are preferably color-coded to indicate the intensity fluorescence of its corresponding discrete regions of fluorescing tissue.

The method can also include the steps of determining the distance and/or direction of the tip of a medical device in the surgical field from each of the discrete regions of fluorescing tissue and displaying the distance and/or direction on the display. The method can also include displaying a numerical value corresponding to the area of each region, and or distance of the tip from each region, and/or intensity of fluorescence.

According to a fifteenth embodiment of a system, a method of updating an image of a surgical field containing a plurality of discrete regions of fluorescing tissue responsive to near infrared illumination, is provided.

The system can comprise one or more processors for processing an image of the entire surgical field showing the plurality of discrete regions of fluorescing tissue in false color. These one or more processors can be part of one or more computers, and/or they can be part of other apparatus, for example being incorporated into cameras, image processors, or other equipment. The system can further comprise one or more processors for real-time updating portions of the image as tissue removed from the discrete regions of fluorescing tissues changes the fluorescence of those portions. At least one processor can also superimpose an image of a medical device on the image in a location determined by registering an image currently generated from the medical device with the prior image of the surgical field.

The method can comprise processing an image of the entire surgical field showing the plurality of discrete regions of fluorescing tissue in false color; real-time updating portions of the preoperative image as tissue removed from the discrete regions of fluorescing tissues changes the fluorescence of those portions. The method can further comprise superimposing an image of a medical device on the preoperative image in a location determined by registering a current image generated from the medical device with the prior image of the field.

According to a sixteenth embodiment, a system and method of creating an image of a surgical field containing a plurality of discrete regions of fluorescing tissue responsive to near infrared illumination is provided.

The system can comprise a source of near-infrared illumination and an imaging camera adapted to be moved over the body of the subject to create a scan image of the surface including fluorescence such as from fluorescently tagged cancer cells. The system further comprises a processor for stitching together multiple scans using anatomical features in the images and fluorescent features in the images to make a composite map such as highlighting the locations of cancer relative to the surface.

The method comprises stitching together multiple surface scans using anatomical features in the images and fluorescent features in the images to make a composite map.

In an alternative to the sixteenth embodiment, the system can comprise a source of near-infrared illumination and an imaging camera having a position sensor that is adapted to be moved over the body to detect fluorescence, and a processor for making a three-dimensional map using scanner position data and detected fluorescence such as highlighting the locations of cancer relative to the surface.

The method comprises making a three-dimensional map using imaging system position data and detected fluorescence.

BRIEF DESCRIPTION OF THE DRAWINGS

FIG. 3A is a diagram showing the pixels in an image of a surgical field showing near-infrared fluorescence and near infrared emitting tissues in the surgical field;

FIG. 3B is a diagram showing the pixels in an image of the surgical field showing near-infrared emitting tissue;

FIG. 3C is a diagram showing the pixels in an image of the surgical field showing only near-infrared fluorescing tissue with near-infrared emitting tissue is removed;

FIG. 3D is a diagram showing the pixels in an image of the surgical field, showing the areas of near-infrared fluorescence colorized according to the intensity of the near-infrared fluorescence;

FIG. 4 is a flow chart of the method of the first embodiment;

FIG. 5 is a schematic diagram of a second embodiment of a system for real time visualizing a surgical field containing a plurality of discrete regions of fluorescing tissue responsive to near-infrared illumination;

FIG. 6A is a diagram showing the pixels in an image of a surgical field showing areas of optical reflection;

FIG. 6B is a diagram showing the pixels in an image of the surgical field showing near-infrared fluorescing tissue and reflections of near-infrared fluorescing tissue;

FIG. 6C is a diagram showing the pixels in an image of the surgical field showing near-infrared fluorescing tissue and areas of possible reflection removed;

FIG. 6D is a diagram showing the pixels in an image of the surgical field, showing the areas of near-infrared fluorescence colorized according to the intensity of the near-infrared fluorescence;

FIG. 8 is a schematic diagram of a first alternative to the second embodiment of a system for real time visualizing a surgical field containing a plurality of discrete regions of fluorescing tissue responsive to near-infrared illumination;

FIG. 9A is a diagram showing the pixels in an image of the surgical field, with the cameras and illumination source at a first position relative to the surgical field;

FIG. 9B is a diagram showing the pixels in an image of the surgical field, with the cameras and illumination source at a second position relative to the surgical field;

FIG. 9C is a diagram showing the pixels in an image of the surgical field, with the cameras and illumination source at a third position relative to the surgical field;

FIG. 9D is a diagram showing the pixels in an image of the surgical field, with the cameras and illumination source at a fourth position relative to the surgical field;

FIG. 10A is a diagram showing the pixels in a raw image of the surgical field;

FIG. 10B is a diagram showing the pixels in an image of the surgical field after processing to remove areas of suspected reflection according to the first alternative to the second embodiment;

FIG. 10C is a diagram showing the pixels in an image of the surgical field showing only near-infrared fluorescing tissue with reflections removed according to the first alternative to the second embodiment, with the fluorescing tissue colorized according to the intensity of the near-infrared fluorescence;

FIG. 11 is a flow chart of the method of the first alternative to the second embodiment;

FIG. 18 is a schematic diagram of a sixth preferred embodiment of a system for real time visualizing a surgical field containing a plurality of discrete regions of fluorescing tissue responsive to near-infrared illumination;

FIG. 19 is a flow chart of the method of the sixth preferred embodiment;

FIG. 21 is a flow chart of the method of the seventh preferred embodiment;

FIG. 22A is a diagram showing the pixels in an image of a surgical field showing near-infrared fluorescence detected by the camera;

FIG. 22B is a diagram showing the pixels in an image of the surgical field, showing the areas of near-infrared fluorescence colorized according to the intensity of the near-infrared fluorescence;

FIG. 23 is a schematic diagram of an eighth preferred embodiment of a system for real time visualizing a surgical field containing a plurality of discrete regions of fluorescing tissue responsive to near-infrared illumination;

FIG. 24A is a diagram showing the pixels in an image of a surgical field showing near-infrared fluorescence detected by the camera;

FIG. 24B is a diagram showing the pixels in an image of the surgical field, showing patterns applied to the areas of near-infrared fluorescence according to the intensity of the near-infrared fluorescence;

FIG. 24C is the key for FIGS. 24A and 24B;

FIG. 25 is a flow chart of the method of the seventh preferred embodiment;

FIG. 31 is a flow chart of the method of the nineth embodiment;

FIG. 43 is a flow chart of the method of the tenth embodiment;

FIG. 44 is a schematic diagram of an eleventh preferred embodiment of a system for real time visualizing a surgical field containing a plurality of discrete regions of fluorescing tissue responsive to near-infrared illumination;

FIG. 45 is an image showing the entire surgical region showing the field of view, in the eleventh embodiment;

FIG. 45A is an image showing the field of view in the eleventh embodiment;

FIG. 52 is an image of the display of a system according to the system and method of the twelfth embodiment;

FIG. 53 is a flow chart of the method of the twelfth embodiment;

FIG. 57 is a flow chart of the method of the thirteenth embodiment;

FIG. 58 is a schematic diagram of a thirteenth preferred embodiment of a system for real time visualizing a surgical field containing a plurality of discrete regions of fluorescing tissue responsive to near-infrared illumination;

FIG. 59 is a flow chart of the method of the thirteenth embodiment;

FIG. 60A is an image of an operating region showing fluorescing tissue;

FIG. 60B is an image of the operating region shown in FIG. 60A, showing the reduction of fluorescing tissue;

FIG. 60C is an image of the operating region shown in FIG. 60B, showing a further reduction of fluorescing tissue;

FIG. 60D is an image of the operating region shown in FIG. 60C, showing a further reduction of fluorescing tissue;

DETAILED DESCRIPTION

Various embodiments of systems and methods for visualizing a surgical field containing a plurality of discrete regions of fluorescing tissue are described herein. These systems and methods are particularly applicable to facilitating procedures where tissue has been tagged with agents such as LS-301 which target cells that express integrins, associated with cancer and other diseases, and fluoresces in the near-infrared band. However, this disclosure is not limited to the use of LS-301, and the disclosed systems and methods also improve the visualization of other fluorescent agents including but not limited to ICG and other cancer-affiliated agents. These systems and methods are adapted for use in surgical fields, including but not limited to open, laparoscopic, endoscopic and microscopic procedures, whether manual or robotic, all of which can be applied to surgeries throughout the human anatomy including but not limited to breast surgery, lymph node surgery, lung surgery, liver surgery, kidney surgery, among many other areas.

Some of the systems and methods of this disclosure improve visualization of abnormal tissue, improving identification of diseased tissue over prior techniques which relied upon pre-operative images, touch, and visual cues. When the abnormal tissues are more accurately identified, tissue excision can be more precise and limited, and delays from intra-procedure histopathology reduced or eliminated, and the need for revision surgeries reduced.

Figure 1A:
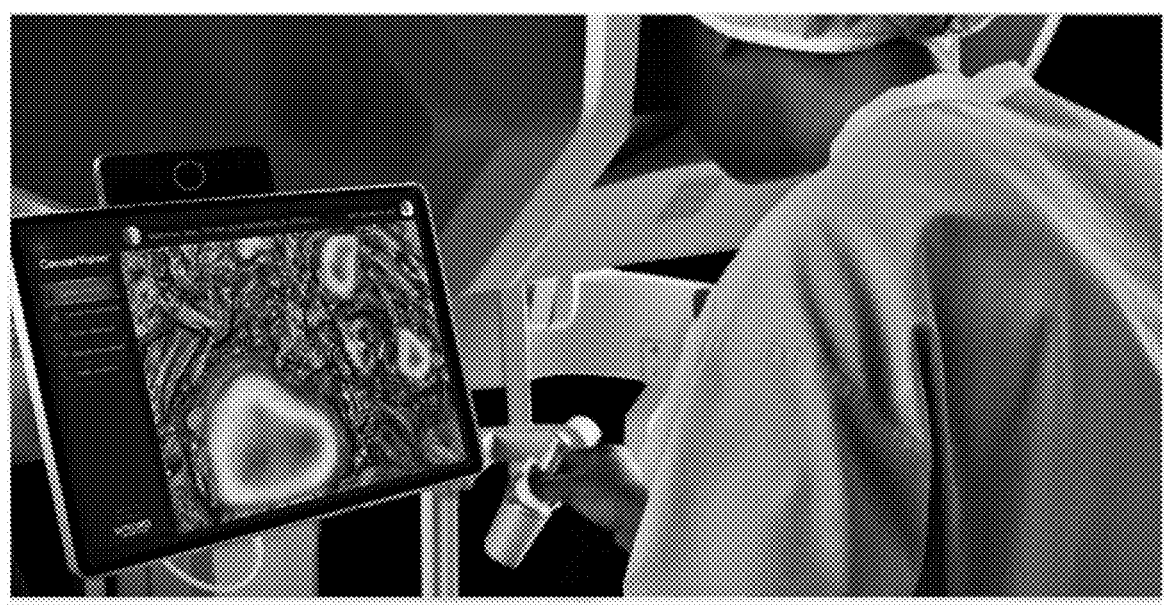
FIG. 1A is an image of a display according to embodiments of the system and method of this disclosure, showing discrete regions of fluorescing tissue colorized for ready identification by a healthcare working.

As shown in FIG. 1A, the systems and methods of this disclosure provide a clear display of the fluorescently tagged tissue, including fluorescence that is otherwise out of the visible spectrum. Color can be applied to indicate varying intensity of the fluorescence, and the color can be dynamically scaled to clearly indicate diseased tissue, even after most of it has been removed. The disclosed systems and methods can reduce or eliminate surgical lighting noise, as well as other artifacts and reflections. Look up tables and algorithms allow high resolution with minimal latency while optimally highlighting tissue of interest in images of the surgical field. Overall, the images of the procedures site are enhanced, and confidence in the procedure increased. The color map can be display as an overlay with full opacity on surgical images, as an overlay with transparency on surgical images or on its own without an underlying surgical image.

Figure 1B:
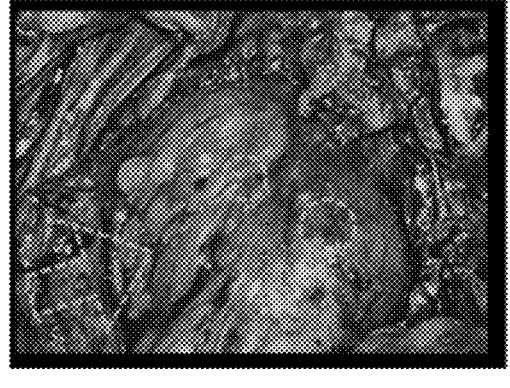
FIG. 1B is an image of a display according to embodiments of the system and method of this disclosure, showing an arrow indicating fluorescing tissue, and a circle indicating fluorescing tissue.
Figure 1C:
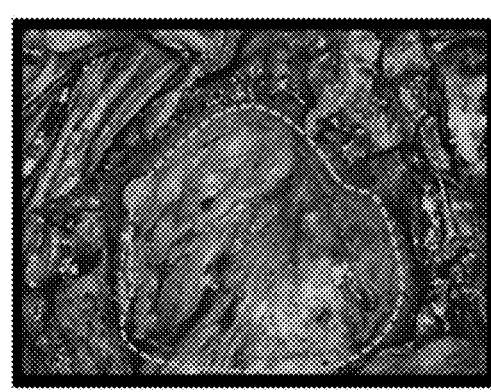
FIG. 1C is an image of a display according to embodiments of the system and method of this disclosure, showing a closely conforming indicator indicating fluorescing tissue.
Figure 1D:
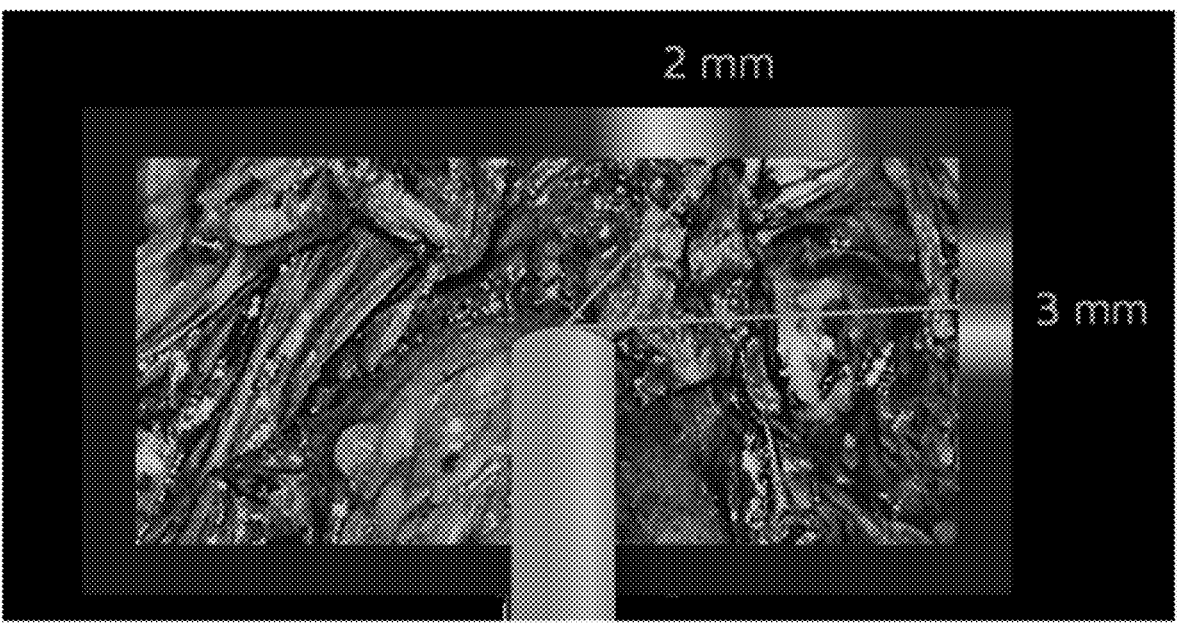
FIG. 1D is an image of a display according to embodiments of the system and method of this disclosure, showing navigational aids for locating areas of fluorescing tissue.
Figure 1E:
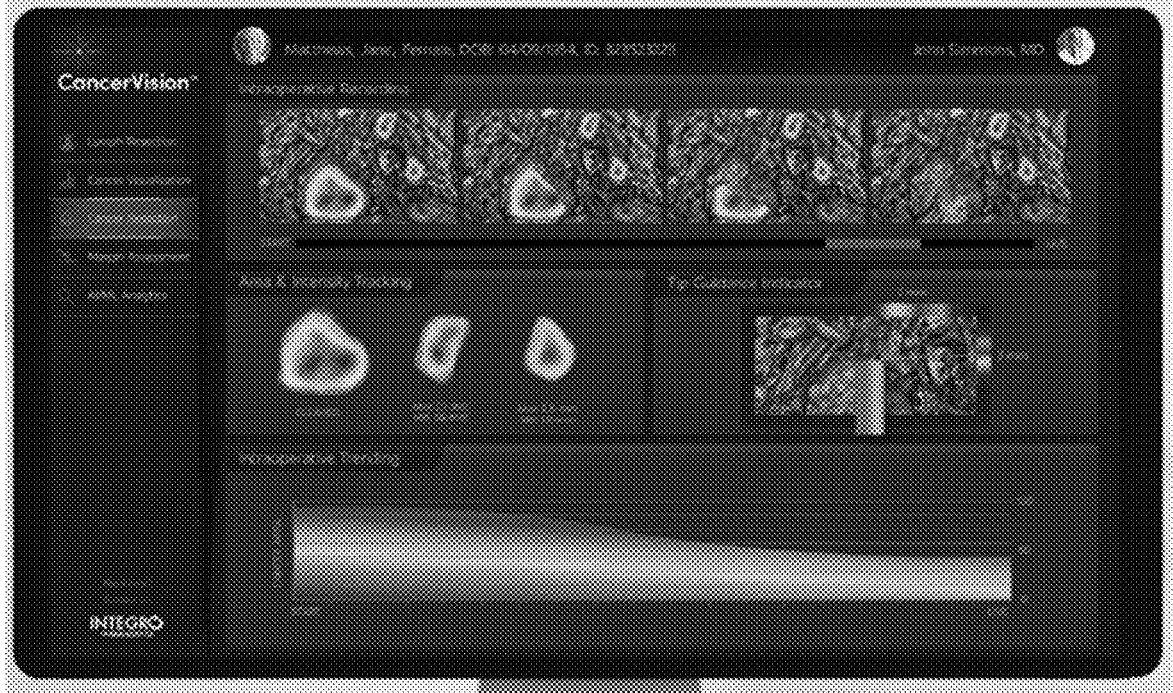
FIG. 1E is an image of a display showing progress indicators.
Figure 1F:
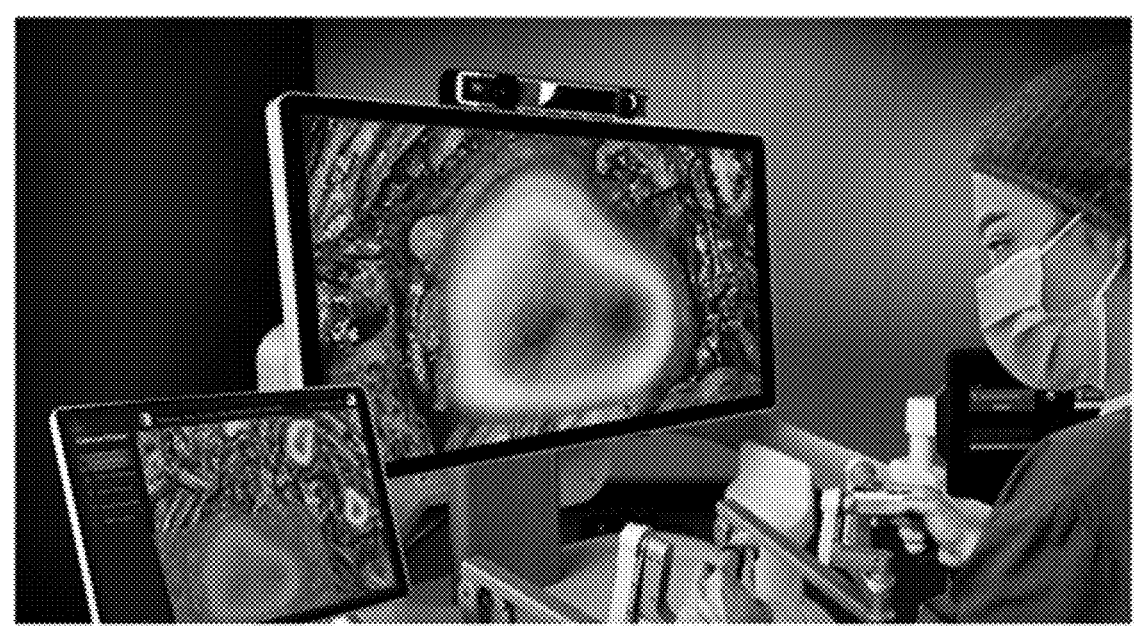
FIG. 1F is a view of a system showing a surgical field display, with an auxiliary display for showing a portion of interest of the surgical field shown in the surgical field display.
Figure 1G:
FIG. 1G is a view of the surgical field display being used to navigate a medical device with the surgical field.

As shown in FIGS. 1B and 1C, the systems and methods of this disclosure can enhance the images, indicating the location of fluorescent tissue with graphic arrows or circles (FIG. 1B), or surrounding the fluorescent tissue with a confirming shape (1C). The graphic indicators may be manually or automatically drawn and may be displayed without or without a surgical image. As shown in FIGS. 1D-1G, the systems and methods can also facilitate navigation through the surgical field, displaying the distance and intensity of fluorescent tissue outside the current field of view. Finally, as shown in FIG. 1E, the systems and methods can provide displays that keep the surgeons aware of the status of the procedure with a modular user interface, displaying the quantity and intensity of fluorescent tissue remaining in the surgical field, either as discrete areas, or collectively, among an array of other elements to better inform surgeons.

Removing Imaging Artifacts

According to a first such embodiment, a system and method for the elimination of artifacts due to ambient light from procedure site images (whether still or moving) is provided to improve visualizing a surgical field containing a plurality of discrete regions of fluorescing tissue. This fluorescence, for this first embodiment and for all of the embodiments described in this disclosure, can be in the near-infrared (NIR) range of the infrared spectrum (generally from about 0.75 µm to about 1.4 µm), for example from LS-301 under stimulated illumination in the near-infrared range of the infrared spectrum. Of course, other agents could be used which fluoresce in the same or different ranges of the electromagnetic spectrum, under stimulating illumination of the same or different ranges of the electromagnetic spectrum, for example the short-wavelength infrared range (SWIR) of the infrared spectrum (generally from about 1.4 µm to about 3 µm).

Figure 2:
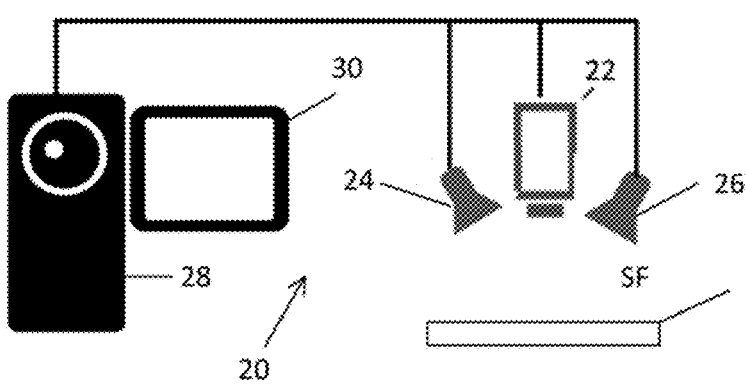
FIG. 2 is a schematic diagram of a first embodiment of a system for real time visualizing a surgical field containing a plurality of discrete regions of fluorescing tissue responsive to near-infrared illumination.

An exemplary system of this first embodiment for real-time visualizing a surgical field containing a plurality of discrete regions of fluorescing tissue is indicated generally as 20 in FIG. 2. The system 20 preferably comprises a source 24 for stimulating illumination. For this first embodiment, and for all of the embodiments described in this disclosure, the source can be an infrared lamp or LED or group of LEDs, which may or may not be filtered. The source may be tuned to the wavelength of maximum absorption for the agent being used, or to a range of wavelengths to elicit the desired fluorescence, for example in the near-infrared range or the short-wavelength infrared range. The system 20 preferably also includes a source 26 of visible light illumination, for illuminating the surgical field for visual observation by treating heath care professionals.

At least one imaging camera 22 capable of imaging in visible light and in the wavelength range of the fluorescence of interest. For example, in the case of LS-301, the one or more cameras 22 preferably image in the near-infrared range of wave lengths (typically 0.75 μm-1.4 μm. With other agents, the camera 22 can be adapted to detect different wavelengths ranges of fluorescence. Of course, filters can be used with the cameras 22 to achieve imaging in the wave lengths of interest. Furthermore, the camera 22 can be integrated with other equipment, such as endoscopes and laparoscopes.

At least one processor can be provided for processing image data from the at least one camera 22 to reduce artifacts in the images resulting from ambient lighting. The at least one processor can be conveniently provided in at least one computer 28, which can run an image processing program stored in memory associated with or connected to the at least one computer 28 and for example in the case of LS-301 can differentially process images of the surgical field when the surgical field is illuminated with near-infrared illumination (e.g., FIG. 3A), and when the surgical field is not illuminated by near-infrared illumination (e.g., FIG. 3B), removing near-infrared image components in the images obtained without near-infrared illumination from the images made with near-infrared illumination, to remove artifacts from the near-infrared illuminated images that were not caused by the fluorescence of the tissue in the surgical field (e.g., FIG. 3C). Of course, for agents other than LS-301, the fluorescence would be measured in the appropriate wavelength range for that agent, and the image data processed to remove artifacts not attributable to fluorescing tissue.

Of course, the removed artifacts can be replaced with blank pixels, but are preferably replaced with substitute pixels based upon pixels surrounding the removed pixel, so that the removed artifact does not distract the surgeon or interfere with his or her interpretation of the surgical field.

The at least one processor could be integrated into some other piece of equipment than computer 28, for example into the at least one camera 22, or into a separate image processing unit.

The at least one processor in the at least one computer 28 can also run an image processing program stored in memory associated with or connected to the at least one computer 28 to apply color to the images to indicate the intensity of fluorescence of the discrete regions of fluorescing tissue. The at least one processer can use a look-up table to apply color to an area of the image based upon the measured intensity of fluorescence in that area, or alternatively the at least one processor can use an algorithm to apply color to each area based upon the measured intensity of fluorescence in that area, as shown in FIG. 3D where R=red; O=orange; Y=yellow; and B=blue. Specific colors can be assigned to specific intensities or ranges of intensities of fluorescence so that intensity is displayed uniformly, e.g., ted which could represent an intensity of the highest concentration of cancer cells in the case of LS-301. For example, the intensities might be measured on a 0-255 scale. Alternatively, the measured intensities of fluorescence can be scaled, and color applied based upon the scaling, for example, so that the most intense fluorescence is always displayed in the same color, e.g., red, regardless of the level of intensity, or to only display a selected range of the measured intensities. Further, in certain circumstances, it might be desirable to limit the colorization to lower intensities, to make it easier to visualize the tissue that fluoresce at a lower intensity, without being overwhelmed by the tissue that fluoresces at higher intensity. Thus, there could be a mode of operation that does not colorize intensities above 100 in a 0-255 scale (or some other fixed or adjustable threshold).

Finally, the system 20 can include a display 30 for displaying the processed, colored image of the portion of the surgical field SF captured by the at least one camera 22.

A first embodiment of a method for reducing artifacts from ambient light in images of a surgical field containing a plurality of discrete regions of fluorescing tissue responsive to near-infrared illumination is indicated generally as 40 in FIG. 4. As shown in FIG. 4, the method can comprise at 42 imaging the surgical field under visible light illumination with an NIR-sensitive camera to obtain an image of at least a portion of the surgical field (e.g. FIG. 3B); at 44 imaging the surgical field under near-infrared illumination with an NIR-sensitive camera to obtain an image the same portion of the surgical field as in 42; at 46 converting both images to 8-bit grayscale; and at 48 subtracting the intensity values of the image under visible light illumination from the same pixel location under NIR illumination to eliminate artifacts from the image not caused by the fluorescence of the tissue, using standard image processing libraries such as OpenCV and obtain an image of the portion of the surgical field showing only the fluorescence of tagged tissue (e.g., FIG. 3C). The method can further comprise at 50 applying color to the differentially processed image to indicate the intensity of fluorescence of the discrete regions of fluorescing tissue, as described above with respect to the system 20. Lastly, at 52 displaying on a display 30 the colored, processed image of the portion of the surgical field captured by the camera (FIG. 3D).

Removing Reflection Artifacts

According to a second such embodiment, a system and method for eliminating artifacts due to reflections is provided to improve visualizing a surgical field containing a plurality of discrete regions of fluorescing tissue. An exemplary system of this second embodiment for real-time visualizing a surgical field containing a plurality of discrete regions of fluorescing tissue responsive to near-infrared illumination is indicated generally as 60 in FIG. 5. The system 60 preferably comprises a source 24 of near-infrared illumination as described above with respect to the first embodiment, and preferably also includes a source 26 of visible light illumination. At least one imaging camera 22, as described above with respect to the first embodiment, capable of visible and near-infrared imaging is provided for imaging a portion of the surgical field SF. Alternatively, there may be at least two cameras 262, including at least one camera capable of visible light imaging, and at least one camera capable of near-infrared imaging.

The system 60 preferably includes at least one processor for processing image data from the at least one camera 22 to reduce artifacts in the images resulting from reflections. The at least one processor can be part of at least one computer 28, as described above with respect to the first embodiment. The at least one computer 268 can run an image processing program stored in memory associated with or connected to at least one computer 3 0that can identify areas of suspected reflection in images of the surgical field SF under white light illumination, as shown in FIG. 6A. This can be done by processing the image of the surgical field obtained by the at least one camera 22 under illumination from visible light source 26, either by identifying bright spots in the image, or by comparing an image with and without illumination from light source 26. Once suspected reflections are identified and located, these positions can be filtered or subtracted from images under near-infrared illumination (e.g., FIG. 6B) to eliminate possible reflected near-infrared fluorescence from the image of the surgical field, resulting in an image (e.g., 6C) that only has true fluorescence, and not reflected fluorescence.

At least one processor in at least one computer 28 can also run an image processing program stored in memory associated with or connected to the at least one computer to apply color to the images to indicate the intensity of fluorescence of the discrete regions of fluorescing tissue. The at least one processer can use a look-up table to apply color to an area of the image based upon the measured intensity of fluorescence in that area, or alternatively the at least one processor can use an algorithm to apply color to each area based upon the measured intensity of fluorescence in that area, as shown in FIG. 6D where R=red; O=orange; Y=yellow; and B=blue. Specific colors can be assigned to specific intensities or ranges of intensities of fluorescence so that intensity is displayed uniformly, e.g., red which could represent an intensity of the highest concentration of cancer cells in the case of LS-301, for example, as noted above the intensities can be scaled from 0-255. Alternatively, the measured intensities of fluorescence can be scaled, and color applied based upon the scaling, so that the most intense fluorescence in the current field of view is always displayed in the same color, e.g., red, regardless of the level of intensity. The overlays with the right color mappings can be generated using standard image processing libraries such as OpenCV. Finally, the system includes a display 30 for displaying the processed, colored image of the portion of the surgical field SF captured by the at least one camera 22.

The at least one processer can use a look-up table to apply color to an area of the image based upon the measured intensity of fluorescence in that area, or alternatively at least one processor can use an algorithm to apply color to each area based upon the measured intensity of fluorescence in that area, as shown in FIG. 6D where R=red; O=orange; Y=yellow; and B=blue. Specific colors can be assigned to specific intensities or ranges of intensities of fluorescence so that intensity is displayed uniformly, e.g., red which could represent an intensity of the highest concentration of cancer cells in the case of LS-301, which as indicated above can be on a scale of 0-255. Alternatively, the measured intensities of fluorescence can be scaled, and color applied based upon the scaling, so that the most intense fluorescence in the current field of view is always displayed in the same color, e.g., red, regardless of the level of intensity. The overlays with the right color mappings can be generated using standard image processing libraries such as OpenCV. Finally, the system includes a display 30 for displaying the processed, colored image of the portion of the surgical field SF captured by the at least one camera 22.

Figure 7:
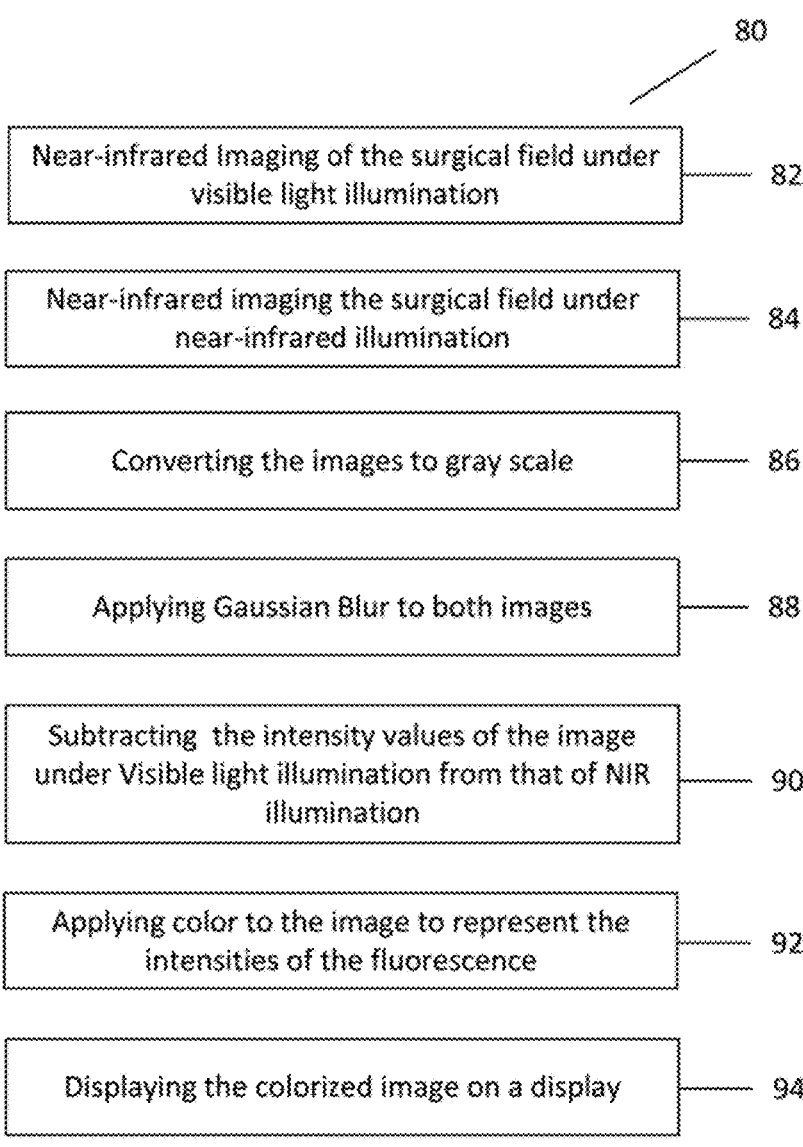
FIG. 7 is a flow chart of the method of the second embodiment.

A second embodiment of a method for reducing artifacts from reflections in images of a surgical field containing a plurality of discrete regions of fluorescing tissue responsive to near-infrared illumination is indicated generally as 80 in FIG. 7. The method 80 comprises at 82 near-infrared imaging at least a portion of the surgical field under visible light (e.g., FIG. 6A), and at 84 near-infrared imaging the same portion of the surgical field under fluorescence-stimulating (e.g., near-infrared illumination) (e.g., FIG. 6B). The method 80 further includes at 86 converting both images to 8-bit grayscale, and at 88 applying a Gaussian blur, with a standard deviation of 1.76 to both images. At 90 the intensity values of each pixel in the image under visible light illumination is subtracted from the intensity values of the corresponding pixels in the image under near-infrared illumination, using standard image processing libraries such as OpenCV to remove suspected reflections to eliminate possible reflected near-infrared fluorescence from the image of the surgical field, (e.g., FIG. 6C).

Finally, at 92 colors can preferably be applied to the filtered images to indicate the intensity of fluorescence of the discrete regions of fluorescing tissue, as described above with respect to system 60. Lastly, at 94 the colored processed image of the portion of the surgical field captured by the at least one camera can be displayed. The color can be applied by referencing a look-up table up table to apply color to an area based upon the measured intensity of fluorescence in that area, or alternatively, by using an algorithm to apply color to the image comprising each area based upon the measured intensity of fluorescence in that area.

In a first alternative of the second embodiment shown in FIG. 8, the system 60' is similar to system 60 described above and corresponding parts are identified with corresponding reference numerals. The system 60' includes one or more processors, which may be provided in at least one computer 28, that can execute programs stored in memory associated with, or connected to, the at least one computer for processing image data from the at least one camera 22 to reduce artifacts in the images resulting from reflections, by tracking the locations of potential reflections over multiple images (e.g., FIGS. 9A-9D). The at least one processor can then remove or filter the potential reflections from the raw image (e.g., FIG. 10A), i.e., the potential reflections that do not appear in all images, resulting in a filtered image (e.g., FIG. 10B) with only fluorescence from the tissue. As described above with system 60, the one or more processors can execute programs stored in memory associated with the computer 28 for applying color to the filtered images to indicate the intensity of fluorescence of the discrete regions of fluorescing tissue. The filtered, processed image of the portion of the surgical field captured by the camera (e.g., FIG. 10C) can then be displayed on display 30, showing only areas of true fluorescence, and not areas of reflected fluorescence.

The method 80' of the first alternative to the second embodiment is similar to method 80, and corresponding steps are indicated with corresponding reference numerals, as shown in FIG. 11. The method 80' comprises at 82 imaging the surgical field under visible light in multiple configurations or orientations, and at 84 imaging the surgical field under near-infrared illumination. At 94 near-infrared Imaging of the surgical field under visible light illumination in at least one additional configuration or orientation. At 96, identifying as reflections locations in the initial image of the surgical field under visible light where the decrease in the intensity at the same location in an image from a different configuration or orientation exceeds a predetermined threshold.' At 96, subtracting the intensity values of the locations identified as reflections from the image of the surgical field under near-infrared illumination to remove suspected reflections to eliminate possible reflected near-infrared fluorescence from the image of the surgical field, (e.g., FIG. 9B).

Finally, at 92 colors can preferably be applied to the filtered images to indicate the intensity of fluorescence of the discrete regions of fluorescing tissue (e.g., FIG. 9B), as described above with respect to system 60'. Lastly, at 94 the colored processed image of the portion of the surgical field captured by the camera can be displayed (e.g., FIG. 9C). The color can be applied as described above.

Improving Image Resolution

According to a third embodiment a system and method for improving image resolution is provided for a surgical field containing a plurality of discrete regions of fluorescing tissue responsive to near-infrared illumination.

Figures 12, 13:
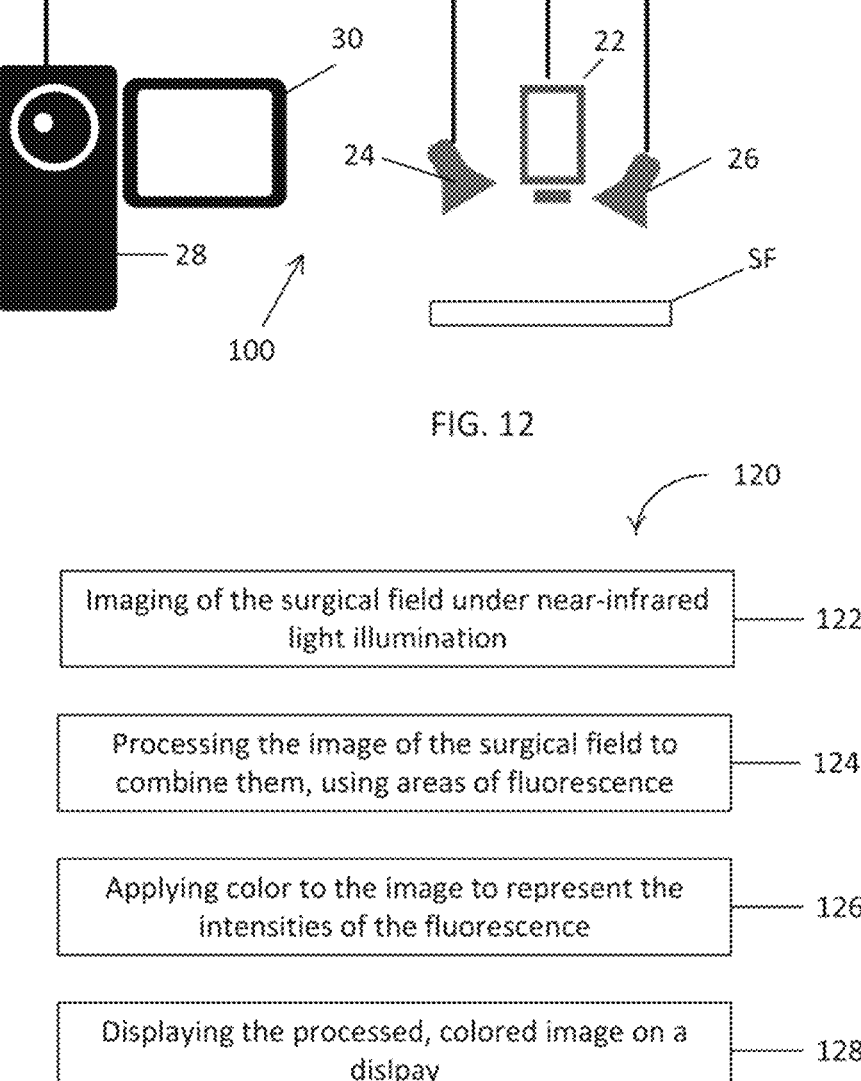
FIG. 12 is a schematic diagram of a third embodiment of a system for real time visualizing a surgical field containing a plurality of discrete regions of fluorescing tissue responsive to near-infrared illumination.
FIG. 13 is a flow chart of the method of the third preferred embodiment.

An exemplary system of this third embodiment is indicated generally as 100 in FIG. 12. The system 100 preferably comprises an imaging camera 22 for imaging a portion of the surgical field SF and can include sources of near-infrared illumination 24, and of white light illumination 26. The system 100 preferably includes at least one processor for processing image data from multiple images of the surgical field at multiple different positions. The at least one processor is preferably part of at least one computer 28. The at least one processor is configured to run an image processing program stored in memory associated with, or connected to, the computer 128. The program can be built using standard image processing libraries such as OpenCV. The program can use the detected fluorescence to align and combine multiple images. Combining the images using fluorescent features in the images to align and combine the multiple images results in a higher resolution image than any of the original images.

At least one processor preferably in at least one computer 28 can also run an image processing program stored in memory associated with, or connected to, the at least one computer to apply color to the images to indicate the intensity of fluorescence of the discrete regions of fluorescing tissue. At least one processer can use a look-up table to apply color to an area of the image based upon the measured intensity of fluorescence in that area, or alternatively at least one processor can use an algorithm to apply color to each area based upon the measured intensity of fluorescence in that area, for example as shown in FIG. 3D where R=red; O=orange; Y=yellow; and B=blue. Specific colors can be assigned to specific intensities or ranges of intensities of fluorescence so that intensity is displayed uniformly, e.g., red which could represent an intensity of the highest concentration of cancer cells in the case of LS-301, for example as noted above, the intensities can be scaled from 0-255. Alternatively, the measured intensities of fluorescence can be scaled, and color applied based upon the scaling, so that the most intense fluorescence is always displayed in the same color, e.g., red, regardless of the level of intensity. The overlays with the right color mappings can be generated using standard image processing libraries such as OpenCV. Finally, the system can include a display 30 for displaying the processed, colored image of the portion of the surgical field SF captured by the at least one camera 22.

A third embodiment of a method for improving the resolution of images of a surgical field is indicated generally as 120 in FIG. 13. The method 120 preferably comprises at 122 imaging a portion of the surgical field under near-infrared illumination, and at 124 processing image data from multiple images of the surgical field at multiple different positions, combining the images using fluorescent features in the image to align and combine the multiple images into a higher resolution image than any of the original images. The method can further comprise at 126 applying color to the differentially processed image to indicate the intensity of fluorescence of the discrete regions of fluorescing tissue, as described above with respect to the system 100. Lastly, at 128 displaying on a display 110 the colored, processed image of the portion of the surgical field captured by the camera.

Identifying Abnormal Tissue

According to a fourth embodiment a system and method for identifying abnormal tissue is provided for use in a surgical field containing a plurality of discrete regions of fluorescing tissue responsive to near-infrared illumination.

Figures 14, 15:
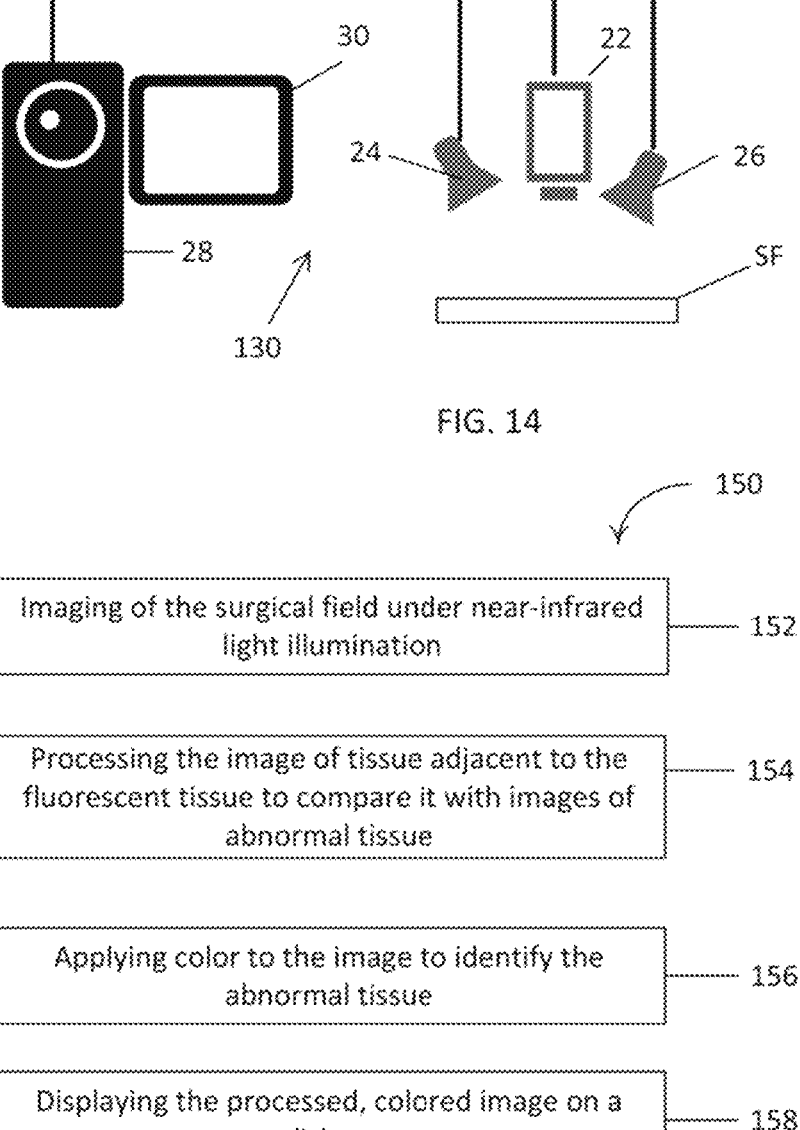
FIG. 14 is a schematic diagram of a third embodiment of a system for real time visualizing a surgical field containing a plurality of discrete regions of fluorescing tissue responsive to near-infrared illumination.
FIG. 15 is a flow chart of the method of the fourth preferred embodiment.

An exemplary system of this fourth embodiment is indicated generally as 130 in FIG. 14. The system 130 preferably comprises at least one imaging camera 22 for imaging a portion of the surgical field SF and can include sources of near-infrared illumination 24, and of white light illumination 26. The system 130 further comprises at least one processor, preferably part of at least one computer 28 for operating an image comparison computer program stored in a memory associated with at least one computer. This program can be built using standard image processing libraries such as OpenCV. The one or more processors process images from the at least one camera 22 to detect abnormal tissue by comparing images of portions of the surgical field SF adjacent to fluorescent tissue with images from a library of abnormal tissue. This library can be stored in a memory associated with at least one computer 138, or it can be a remotely stored database accessible via a network, or via the internet. The one or more processors of the one or more computers 138 can also apply color to the images to indicate the detected abnormal tissue. The one or more processors of at least one computer 28 can use a look-up table to apply color to areas based upon each individual cancer regions such that large high intensity regions would not dictate the color applied to other varying sized regions of tissued identified and instead use an algorithm to apply color to areas based upon each region identified. The system 130 can then display the colored, processed images on the display 30.

A fourth embodiment of a method for identifying abnormal tissue is provided for use in a surgical field under near-infrared illumination is indicated as 150 in FIG. 15. The method 150 comprises at 152 imaging the surgical field under near-infrared illumination. At 154 tissue adjacent the fluorescent tissue in the images is processed and compared to a library of abnormal tissue. At 156, tissue in the images that corresponds to abnormal tissue is colored. Finally at 158, the colored, processed tissue is displayed on display 140. This library can be stored in memory associated with the at least one computer, or it can be accessed via a network. The method can further comprise the step of applying color to the images to indicate the detected abnormal tissue; and displaying the colored processed image of the portion of the surgical field captured by the camera. The step of applying color to the images can be done by referencing a look-up table up table to apply color to an area or using an algorithm to apply color to the image comprising each area.

Identifying Fluids in the Surgical Field

According to a fifth embodiment, a system and method for identifying fluids is identified for use in a surgical field containing a plurality of discrete regions of fluorescing tissue responsive to near-infrared illumination.

Figure 16:
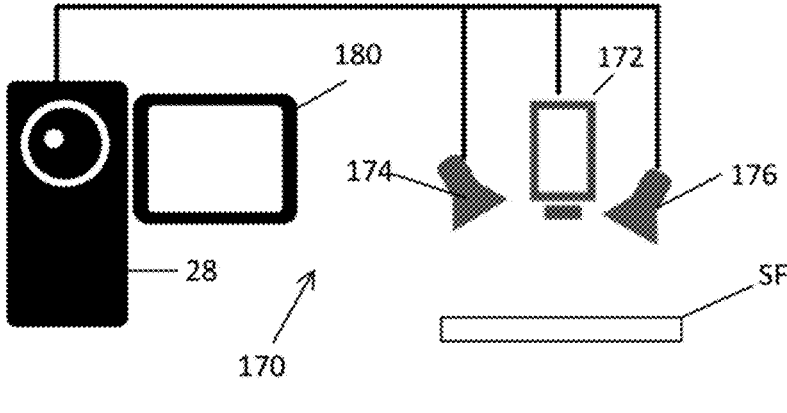
FIG. 16 is a schematic diagram of a fifth preferred embodiment of a system for real time visualizing a surgical field containing a plurality of discrete regions of fluorescing tissue responsive to near-infrared illumination.

An exemplary system of this fifth embodiment is indicated generally as 170 in FIG. 16. The system 170 preferably comprises one or more sources of light 174, 176 of at least two discrete wavelengths, and an imaging camera 22 for imaging a portion of the surgical field SF under each of at least two discrete wavelengths. The system 170 preferably also includes at least one processor for processing images of the surgical field SF from the camera 22 under light from at least two discrete wavelengths, in order to detect to detect fluids. The at least one processor is preferably provided in at least one computer 28. The one or more processors can process software stored in memory associated with the one or more computers 28 and detects differences between images of the same portion of the surgical field under the at least two wavelengths, to determine the presence of fluids in the surgical field. The one or more processors may also apply color to the images to indicate the location of fluid. The at least one processor can use a look-up table to apply color to areas based upon the probability of the presence of liquid, or the processors can use an algorithm to apply color to areas based upon the probability of the presence of liquid.

Figure 17A:
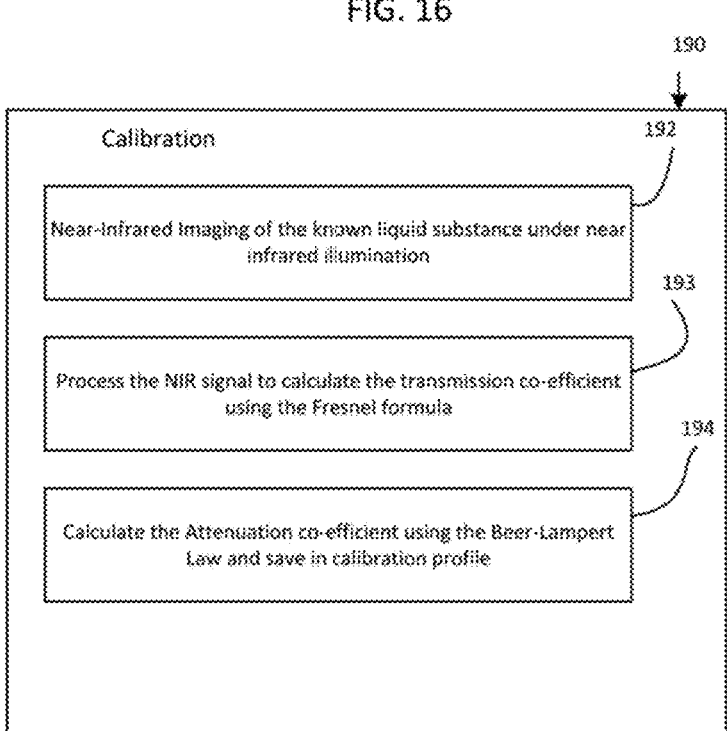
FIGS. 17A-17B are flow charts of the method of the fifth preferred embodiment.
Figure 17B:
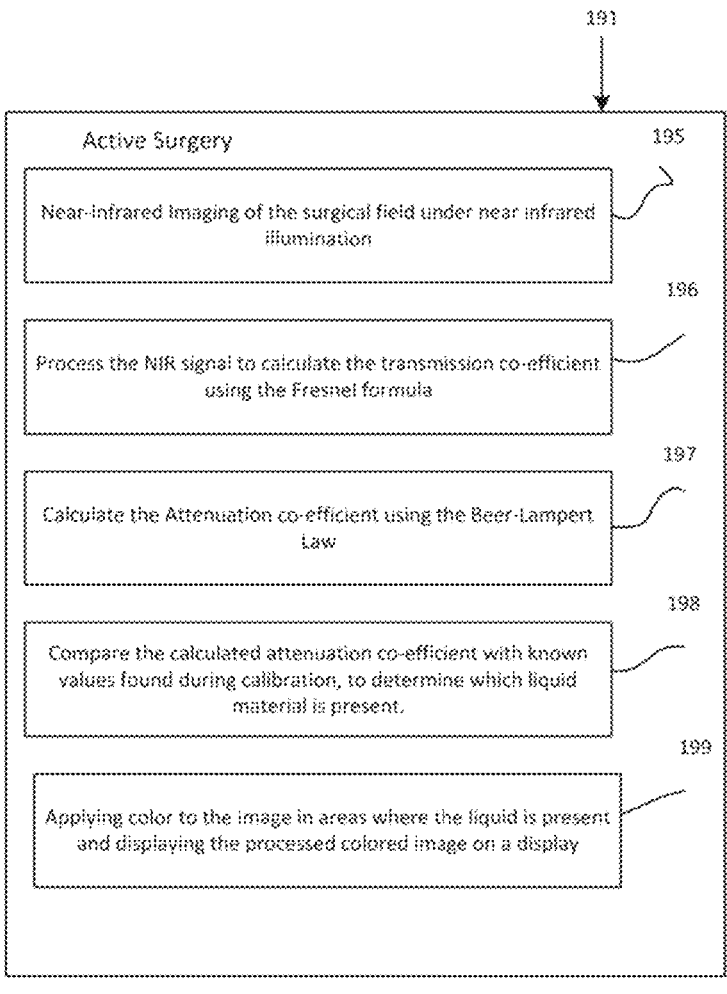

A fifth embodiment of a method for identifying liquids in a surgical field containing a plurality of discrete regions of fluorescing tissue responsive to near-infrared illumination is indicated generally as 190 and 191 in FIGS. 17A-17B. The method 190 (calibration) preferably comprises at 192 imaging the surgical field under near-infrared imaging of a known liquid substance, and at 193 the image is processed to calculate the transmission co-efficient using the Fresnel formula, and at 194 the attenuation co-efficient is calculated using the Beer-Lampert Law and the attenuation co-efficient is saved in the calibration profile. The method 190 is repeated for as many liquid forms that need to be identified in the surgical field. Then at method 191 (Active Surgery), comprises at 195 imaging of the surgical field under near-Infrared illumination, and at 196 processing the NIR signal to calculate the transmission co-efficient using Fresnel formula, and at 197 calculating the attenuation co-efficient using the Beer-Lampert law, and at 198 comparing the attenuation co-efficient with known values found during Calibration (method 190), to determine which liquid material is present.

The method can include at 199 applying color to the images to indicate the location of fluid. The color can be applied using a look-up table to apply color to areas based upon the probability of having liquid or using an algorithm to apply color to areas based upon the probability of the presence of liquid. Alternatively, the locations of liquid can be used to filter the image as the liquid is likely reflect fluorescence. The colored image can be displayed on display 30.

Image Artifact Tracking

According to a sixth embodiment a system and method for tracking artifacts using fluorescent landmarks is disclosed for use in a surgical field containing a plurality of discrete regions of fluorescing tissue responsive to near-infrared illumination.

An exemplary system of this sixth embodiment is indicated generally as 200 in FIG. 18. The system 200 comprises a source of near-infrared illumination and an imaging camera 22 for imaging a portion of the surgical field SF, sources of near-infrared illumination 24 and of white light illumination 26. The system preferably also includes at least one processor, which is preferably associated with at least one computer 28, and can run an image processing program stored in memory associated with, or connected to, the computer 28. The image processing software processes image data from the camera 22 to identify artifacts in the image, identifying discrete regions of fluorescing tissue, and identifying the relationship between the identified artifacts and the identified discrete regions of fluorescing tissue. The at least one processor allows tracking of the location of the artifacts relative to the discrete fluorescent areas and can remove all the artifacts or selected artifacts from images, or otherwise prevent these artifacts from being displayed as fluorescing tissue. The system preferably further comprises a display 30 for displaying the processed image of the portion of the surgical field captured by the camera.

A sixth embodiment of a method for tracking and removing artifacts from still or moving images of the surgical field is indicated generally as 220 in FIG. 19. The method 220 can comprise at 222 imaging a portion of the surgical field and processing image data from the at least one camera 22 to identify artifacts in the image, regions of fluorescent tissue in the image, and the spatial relationship between them. At 224 artifacts in subsequent images of the surgical field are identified and processed based upon their relationship to one or more of the discrete regions of fluorescing tissue. The method preferably further comprises at 226 identifying artifacts in subsequent still or moving images by their relationship to one or more of the discrete regions of fluorescing tissue, and removing the artifacts from the image, or otherwise preventing the artifacts from being displayed as fluorescing tissue. At 228 the processed images can be displayed on a display 30.

Making Fluorescent Tissue Visible in Displays of the Surgical Field

According to a seventh embodiment a system and method for identifying fluorescent tissue is provided for use in a surgical field containing a plurality of discrete regions of fluorescing tissue responsive to near-infrared illumination.

Figure 20:
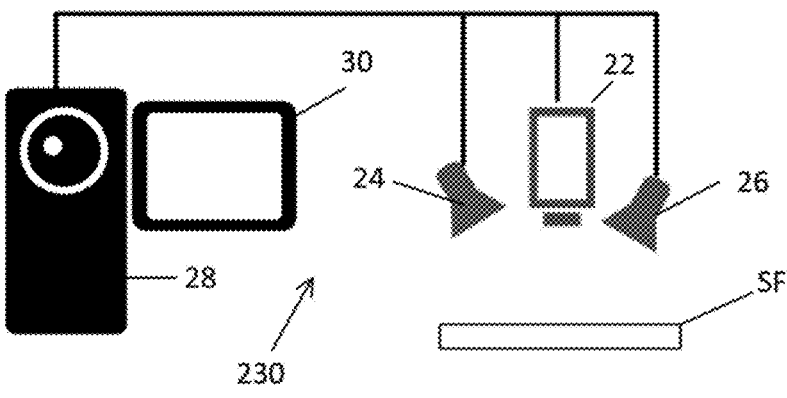
FIG. 20 is a schematic diagram of a seventh preferred embodiment of a system for real time visualizing a surgical field containing a plurality of discrete regions of fluorescing tissue responsive to near-infrared illumination.

An exemplary system of this seventh embodiment is indicated generally as 230 in FIG. 20. The system 230 can comprise a source of near-infrared illumination 24, and at least one imaging camera 22 for imaging a portion of the surgical field SF. The system 230 can also include a source of white light illumination 26.

The system 230 preferably comprises at least one processor for processing image data of the surgical field and for applying color to the images to indicate the intensity of fluorescence of the discrete regions of fluorescing tissue. The at least one processor is preferably associated with at least one computer 28. The at least one processor can use a look-up table to apply color to areas based upon the measured intensity of fluorescence, or alternatively, at least one processor can use an algorithm to apply color to areas based upon the measured intensity of fluorescence. The at least one processor can scale the measured intensities of fluorescence based upon the maximum measured fluorescence intensity in the image in a predetermined minimum area of the image. The system 230 preferably also includes a display 30 for visualizing the processed image of the portion of the surgical field SF captured by the camera.

In a first alternate of the system 230 of the seventh embodiment, the at least one processor dynamically rescales the measured intensities of fluorescence as the maximum measured fluorescence intensity changes. In a second alternative of the system 230 of the seventh embodiment, the at least one processor rescales the measured intensities of fluorescence upon a predetermined change in the maximum measured fluorescence. In a third alternative of the system of 230 of the seventh embodiment, the at least one processor rescales the measured intensities of fluorescence upon a predetermined change in the average measured intensity of the fluorescence of the surgical field.

A seventh embodiment of a method for identifying fluorescent tissue in a surgical field containing a plurality of discrete regions of fluorescing tissue responsive to near-infrared illumination is indicated generally as 250 in FIG. 21. The method comprises at 252 imaging the surgical field with near-infrared illumination (e.g., FIG. 23) and at 254 processing the image to determine the range of intensity (from 0-255). At 256, the fluorescence intensity data from the surgical field is processed to generate a histogram of intensities relative to the maximum value of intensity. At 258, if the maximum intensity is less than 125, the bottom two buckets of the histogram are eliminated, and the histogram is recalculated. identify area of fluorescence (e.g., FIG. 22A); and at 260 a color map based on pixel intensity and bucket association (e.g., bucket 1→Red) is computer. At 262 the color map is overlaid over the image. Finally at 262, the processed, colored image is displayed on display 30 (e.g., FIG. 22B).

In a first alternate of the seventh embodiment, the measured intensities of fluorescence are dynamically rescaled as the maximum measured fluorescence intensity changes, by continuously recalculating the histogram using peak (max) to trough (min) values. In a second alternative of the seventh embodiment, the measured intensities of fluorescence are rescaled upon a predetermined change in the maximum measured fluorescence, by continuously recalculating the histogram using peak (max) to trough (min) values. In a third alternative of the seventh embodiment, the measured intensities of fluorescence are rescaled upon a predetermined change in the average measured intensity of the fluorescence of the surgical field, by continuously recalculating the histogram using peak (max) to trough (min) values Making Fluorescent Tissue Visible in Displays of the Surgical Field According to an eighth embodiment a system and method of using patterned overlays is provided for identifying fluorescent tissue in a surgical field containing a plurality of discrete regions of fluorescing tissue responsive to near-infrared illumination.

An exemplary system of this eighth embodiment is indicated generally as 280 in FIG. 23. The system 280 can comprise a source of near-infrared illumination 24, and at least one imaging camera 22 for imaging a portion of the surgical field SF. The system 280 may also include a source of white light illumination 26. The system preferably includes at least one processor which is preferably part of at least one computer 28 for processing image data of the surgical field from the at least one camera 22, and for applying color to the images to indicate the intensity of fluorescence of the discrete regions of fluorescing tissue.

The at least one processer can use a look-up table to apply a pattern to areas of the image based upon the measured intensity of fluorescence in those areas, or alternatively the at least one processor can use an algorithm to apply patterns to areas of the image based upon the measured intensity of fluorescence in those areas, as shown in FIGS. 24A-24B. Specific patterns can be assigned to specific intensities or ranges of intensities of fluorescence so that intensity is displayed uniformly, as shown in FIG. 24C. Alternatively, the measured intensities of fluorescence can be scaled, and patterned overlays applied based upon the scaling, so that the most intense fluorescence is always displayed in the same pattern. The overlays with the right color mappings can be generated using standard image processing libraries such as OpenCV. This scaling of the measured intensities of fluorescence is preferably based upon the maximum measured fluorescence intensity in the image that covers at least a predetermined minimum area of the image. The system 260 preferably also includes a display 30 for displaying the processed image of the portion of the surgical field captured by the at least one camera 22.

In a first alternate of the eighth embodiment, the at least one processor dynamically rescales the measured intensities of fluorescence as the maximum measured fluorescence intensity changes. In a second alternative of the eighth embodiment, the at least one processor rescales the measured intensities of fluorescence upon a predetermined change in the maximum measured fluorescence. In a third alternative of the eighth embodiment, at least one processor rescales the measured intensities of fluorescence upon a predetermined change in the average measured intensity of the fluorescence of the surgical field.

An exemplary method of this eighth embodiment is indicated generally as 300 in FIG. 25. The method comprises at 302 imaging the surgical field with near-infrared illumination (e.g., FIG. 23), and at 304 processing the image to determine the range of intensity (from 0-255). At 306, the fluorescence intensity data from the surgical field is processed to generate a histogram of intensities relative to the maximum value of intensity. At 308, if the maximum intensity is less than 125, the bottom two buckets of the histogram are eliminated, and the histogram is recalculated. identify area of fluorescence (e.g., FIG. 24A); and at 310 a pattern map based on pixel intensity and bucket association (e.g., bucket 1→Red) is computer. At 312 the pattern map is overlaid over the image. Finally at 214, the processed, colored image is displayed on display 30 (e.g., FIG. 24B)

In a first alternate of the eighth embodiment, the measured intensities of fluorescence are dynamically rescaled as the maximum measured fluorescence intensity changes, by continuously recalculating the histogram using peak (max) to trough (min) values. In a second alternative of the seventh embodiment, the measured intensities of fluorescence are rescaled upon a predetermined change in the maximum measured fluorescence, by continuously recalculating the histogram using peak (max) to trough (min) values. In a third alternative of the seventh embodiment, the measured intensities of fluorescence are rescaled upon a predetermined change in the average measured intensity of the fluorescence of the surgical field, by continuously recalculating the histogram using peak (max) to trough (min) values.

Making Fluorescent Tissue Visible in Displays of the Surgical Field

According to a ninth embodiment a system and method of superimposing indicators for identifying fluorescent tissue is provided for use in a surgical field containing a plurality of discrete regions of fluorescing tissue responsive to near-infrared illumination.

Figure 26:
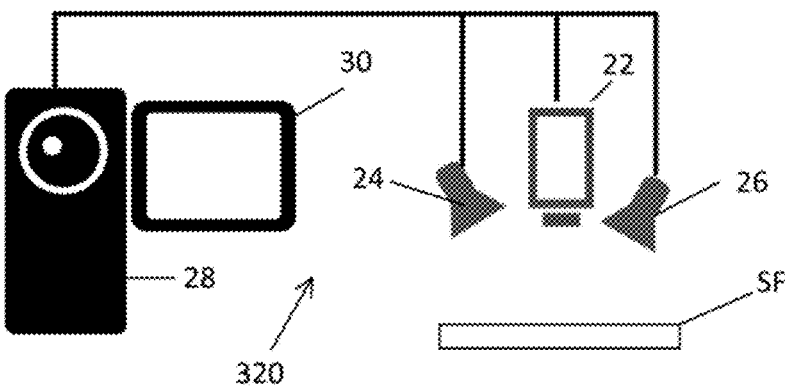
FIG. 26 is a schematic diagram of a nineth preferred embodiment of a system for real time visualizing a surgical field containing a plurality of discrete regions of fluorescing tissue responsive to near-infrared illumination.

An exemplary system of this ninth embodiment is indicated generally as 320 in FIG. 26. The system 320 can comprise a source of near-infrared illumination 24, and at least one imaging camera 22 for imaging a portion of the surgical field. The system 20 may also include a source of white light illumination 26. The system 320 further comprises a display 30. The system further comprises at least one processor for identifying at least one of the discrete regions of fluorescing tissue in the image and superimposing one or more indicators on the displayed image to identify at least one of the discrete regions of fluorescing tissue. The at least one processor can be part of at least one computer 28.

Figure 27:
FIG. 27 is an image of an operating region, with arrow indicators identifying regions of fluorescent tissue.
Figure 28:
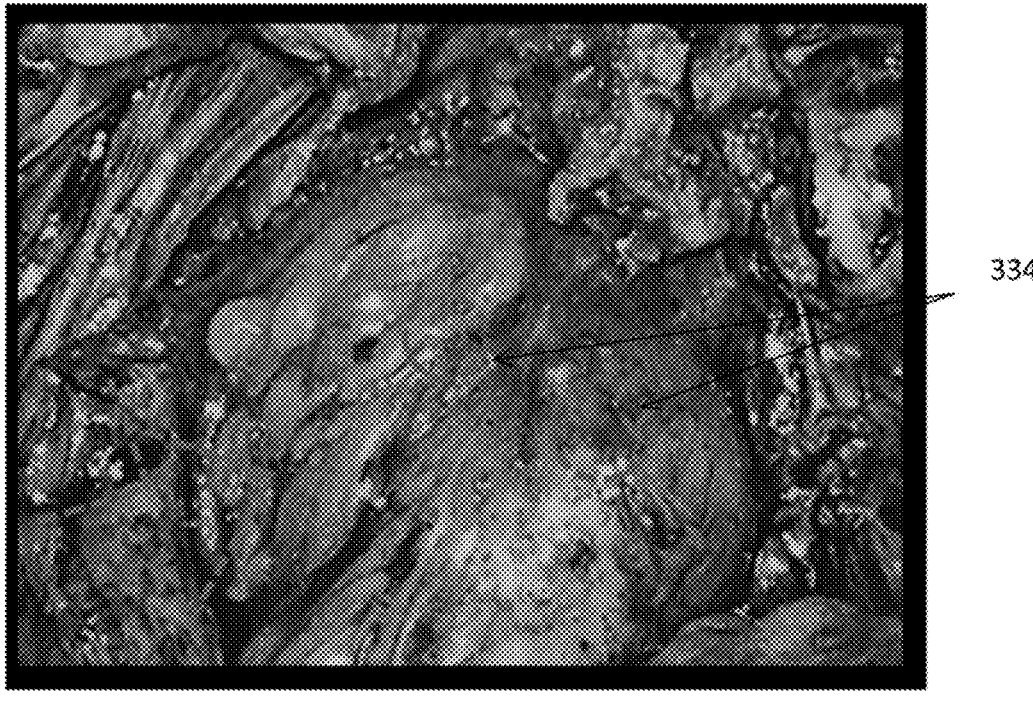
FIG. 28 is an image of an operating region, with circle indicators identifying regions of fluorescent tissue.
Figure 29:
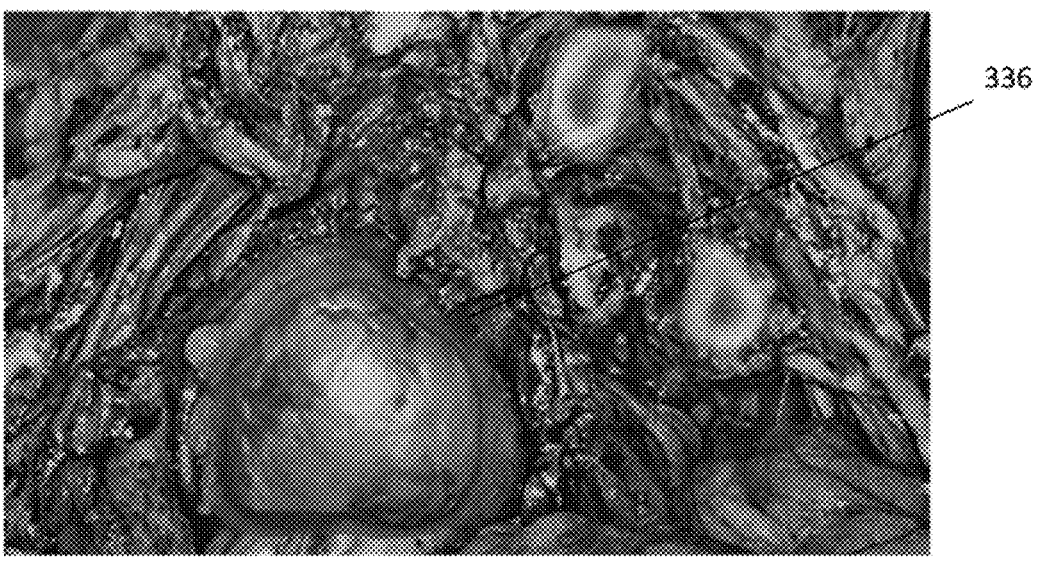
FIG. 29 is an image of an operating region with an indicator closely conforming to, and surrounding, a region of fluorescent tissue.

In a first alternative of the ninth embodiment, the indicator is an arrow 332, pointing to the discrete regions of fluorescing tissue (e.g., FIG. 27). In a second alternative of the ninth embodiment, the indicator is a circle 334 surrounding a discrete region of fluorescing tissue (e.g., FIG. 28). The at least one processor can size the circle to include multiple discrete regions of fluorescing tissue that are within a predetermined distance from each other. In a third alternative of the ninth embodiment, the indicator is a boundary line 336 closely conforming to the edges of the discrete region of fluorescing tissue, preferably with a predetermined minimum radius of curvature (e.g., FIG. 29). In this third alternative, the system can include a control, for example implemented by computer 328 for adjusting the predetermined minimum radius of curvature, for example 2 mm or 2 pixels. In circumstances it may be difficult to scale the images so that instead of a dimension, the curvature is determined by the number of pixels. The at least one processor can define (in size and shape) the boundary line 336 to include multiple discrete regions of fluorescing tissue that are within a predetermined distance from each other. This predetermined distance can be established in advance, or it can be set during the procedure, for example with a control on computer 28.

Figure 30:
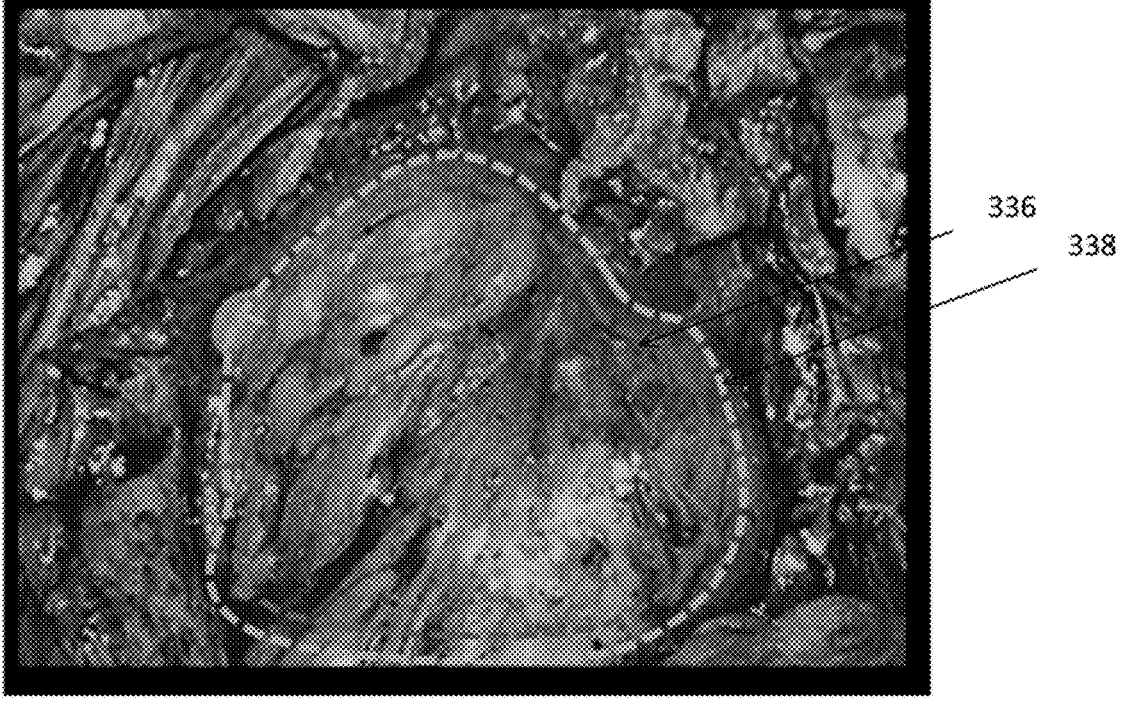
FIG. 30 is an image of an operating region with an indicator closely conforming to, and surrounding, a region of fluorescent tissue, and a boundary line closely conforming to, but spaced from, the indicator.

In a fourth alternative of the ninth embodiment, the processor not only displays a boundary line 336 on the image of the surgical field, but further displays a peripheral line 338 spaced outside of the boundary line a predetermined distance (e.g., FIG. 30). This predetermined distance can be determined by at least one processor based upon the area of the discrete region of fluorescing tissue or based on the intensity of the discrete region of fluorescing tissue, or based on the average intensity of the discrete region of fluorescing tissue, or based on the maximum intensity of the discrete region of fluorescing tissue, or based on the density of fluorescent areas, or based on some other criteria.

In a fifth alternative of the ninth embodiment, the indicator is a polygon surrounding a discrete region of fluorescing tissue and/or non-cancerous anatomy to be avoided. At least one processor can size the polygon to include just one or multiple discrete regions of fluorescing tissue that are within a predetermined distance from each other. At least one processor can change the appearance of the polygon over time by, for example, making it flash, fade in and out, rotate, increase in size, or decrease in size. The changing appearance of the polygon can serve as a better attentional guide to the surgeon.

An exemplary method of this ninth embodiment is indicated generally as 350 in FIG. 31. The method 350 can comprise at 352 near-infrared imaging of the surgical field with near-infrared illumination. At 354 the images are processed using a modified version of Canny Edge Detection algorithm to identify the edges of the illuminated area based on a threshold. This involves at 345A applying a Gaussian Blur (with standard deviation of 1.76) to reduce noise artifacts; at 345B applying Sobel filters, using a standard image processing library such as OpenCV, to enhance intensity of the pixels on the edges; and at 354C applying a hysteresis function to identify sure edges (edges with intensity>high threshold are sure edges, edges with intensity<low threshold are not edges, edges with intensity in between high and low are edges only if they are connected to sure edges). At 356 at least one discrete region is selected, and the appropriate indicator applied to it. This selection can be based on predetermined criteria, such as the largest region, the region with the highest intensity, the region with the highest average intensity, or some other criteria. At 358 the method can further comprise displaying the processed image, including the added indicators, on a display.

In a first alternative of the ninth embodiment, the indicator applied at 356 is an arrow 332, pointing to the discrete regions of fluorescing tissue (e.g., FIG. 27). In a second alternative of the ninth embodiment, the indicator applied at 356 is a circle 334 surrounding a discrete region of fluorescing tissue (e.g., FIG. 28). The at least one processor can size the circle 334 to include multiple discrete regions of fluorescing tissue that are within a predetermined distance from each other or meet some other criteria. In a third alternative of the ninth embodiment, the indicator applied at 356 is a boundary line 336 closely conforming to the edges of the discrete region of fluorescing tissue, preferably with a predetermined minimum radius of curvature (e.g., FIG. 29). In this third alternative, the system can include a control for adjusting the predetermined minimum radius of curvature. The at least one processor can size the boundary line to include multiple discrete regions of fluorescing tissue that are within a predetermined distance from each other or meet some other criteria.

In a fourth alternative of the ninth embodiment, the indicator applied at 356 is not only a boundary line 336 but also a peripheral line 338 spaced outside of the boundary line a predetermined distance. This predetermined distance can be determined based on the area of the discrete region of fluorescing tissue, based on the intensity of the discrete region of fluorescing tissue, based on the average intensity of the discrete region of fluorescing tissue, based on the maximum intensity of the discrete region of fluorescing tissue, based on the density of fluorescent areas, the nature of the tissue being imaged, or based upon some other criteria.

In a fifth alternative of the ninth embodiment, the indicator is a polygon surrounding a discrete region of fluorescing tissue and/or non-cancerous anatomy to be avoided. At least one processor can size the polygon to include just one or multiple discrete regions of fluorescing tissue that are within a predetermined distance from each other. At least one processor can change the appearance of the polygon over time by, for example, making it flash, fade in and out, rotate, increase in size, or decrease in size. The changing appearance of the polygon can serve as a better attentional guide to the surgeon.

Signaling Zone

According to a tenth embodiment a system and method of superimposing a signaling zone on or around an image of a surgical field containing a plurality of discrete regions of fluorescing tissue responsive to near-infrared illumination is provided.

Figure 32:
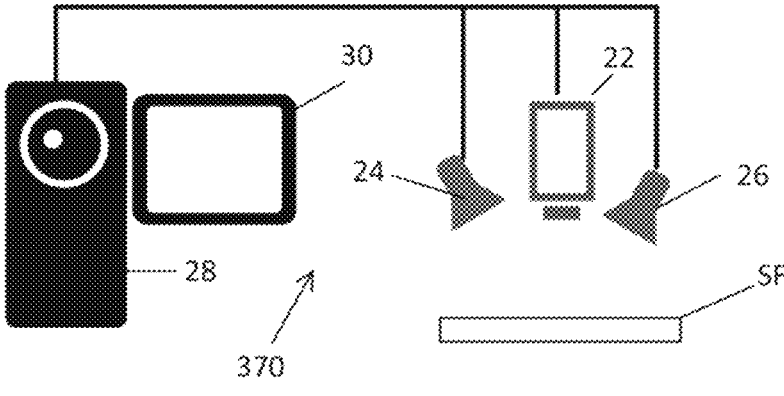
FIG. 32 is a schematic diagram of a tenth preferred embodiment of a system for real time visualizing a surgical field containing a plurality of discrete regions of fluorescing tissue responsive to near-infrared illumination.
Figure 33:
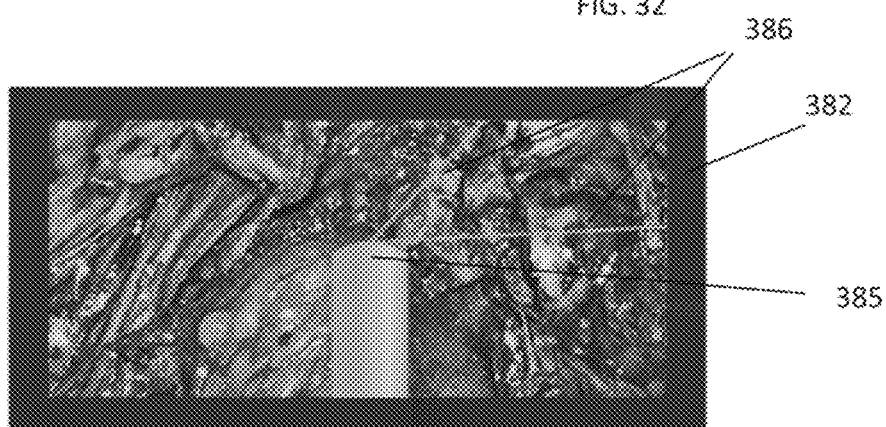
FIG. 33 is an image of an operating region, with a signal zone surrounding the image.
Figure 34:
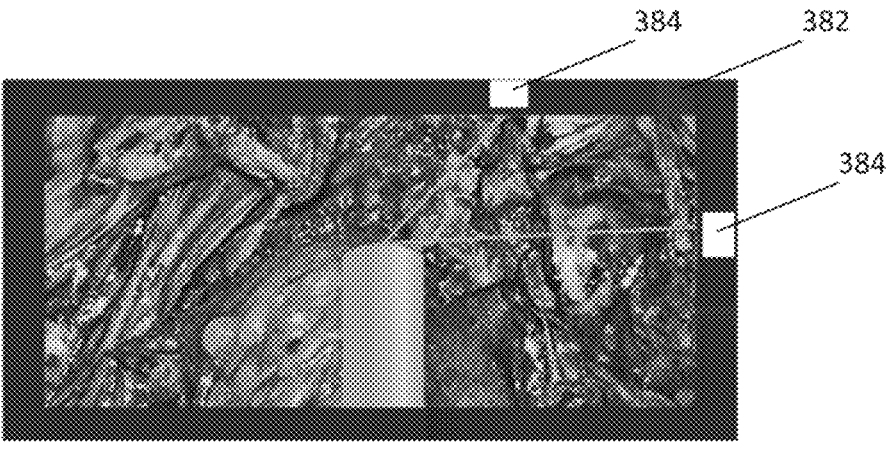
FIG. 34 is an image of an operating region, with indicators in the signal zone surrounding the image.

An exemplary system of this tenth embodiment is indicated generally as 370 in FIG. 32. The system can comprise a source of near-infrared illumination 24, and at least one imaging camera 22 for imaging a portion of the surgical field SF. The system 370 may also include a source of white light illumination 26. The system 370 further comprises a display 30. The system can additionally include at least one processor running a program for displaying the images from at least one camera 22 and for generating a signaling zone 382 on the display 30 at least partially surrounding the image of the portion of the surgical field, as shown in FIG. 33. As also shown in FIG. 33, a representation of a medical device tip 385 can be shown in the image of the surgical field. This representation 385 may be an actual image of the medical device tip. This representation may also be an artificial construction, or it could be a constructed image to facilitate visualization. If the representation of the medical device tip 385 is included, then directional indicator rays 386 can also be provided from either representation of the medical device tip or the center of the view to adjacent regions of fluorescence outside the field of view. The at least one processor is preferably part of at least one computer 28. The at least one processor can further display in the signaling zone 382 an indicator 384 of at least one adjacent discrete region of fluorescing tissue that is outside of the displayed image, as shown in FIG. 34. Each indicator 384 is preferably located in that portion of the signaling zone 382 that is closest to the adjacent discrete region of fluorescing tissue that the indicator represents, thereby indicating to a health care worker concentrating on the discrete region currently displayed on the monitor, the general locations of other discrete regions to be addressed. The display of the signaling zone on or around an image can optionally be turned on and off.

Figure 38:
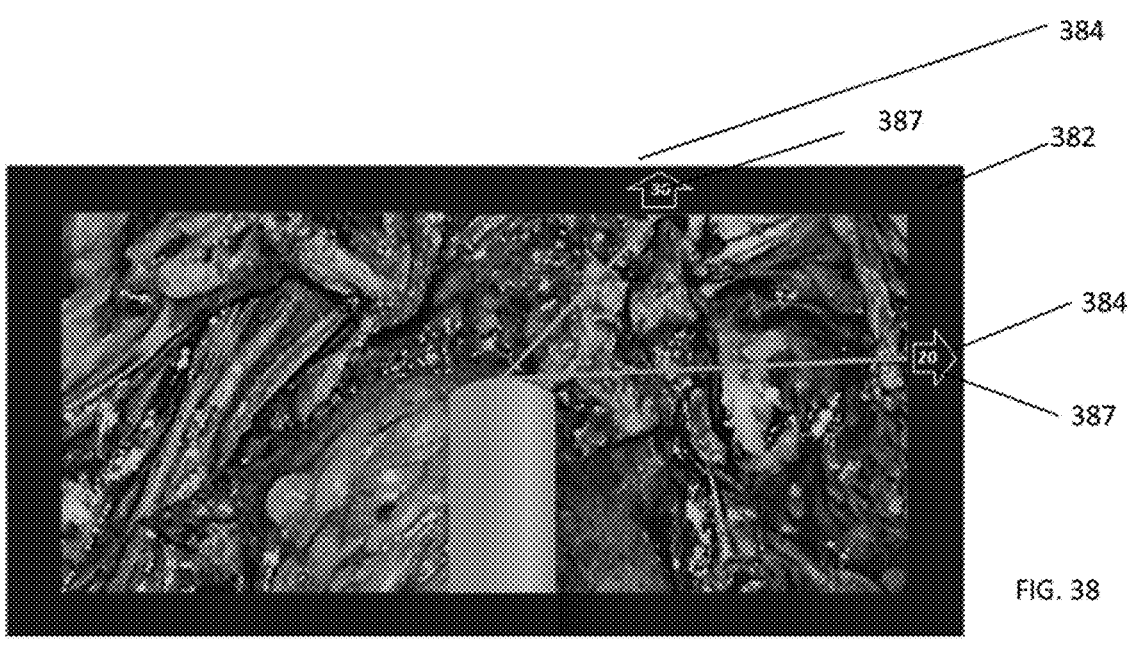
FIG. 38 is an image of an operating region, with indicators in the signal zone surrounding the image.

The image of the surgical field is preferably generally circular, and the signaling zone is a circular ring surrounding the circular image of the surgical field. However, the image of the surgical field can also be generally rectangular, as shown, and the signaling zone 382 could be a rectangular ring surrounding the rectangular image of the surgical field, like a picture frame. In a first alternative to the tenth embodiment, each indicator 384 can be coded to represent the distance between the edge of the image and its respective discrete region (e.g., FIG. 35). The distance could also be measured from the center of the discrete region being displayed, or preferably from the edge of the discrete region being displayed. Of course, the indicators could also represent the distance between the center of the current display, or the edge of the current display adjacent the indicator. Each indicator can represent distance with the color or color properties (hue, saturation, brightness) (e.g., FIG. 36), shape, size, or width of the indicator, with indicia, with numbers, or with text (ex. letters, abbreviations, words), or symbols, or combinations of numbers, letters, and/or symbols. For example, in FIG. 35 the red arrow could indicate a closer discrete region than the orange arrow indicates (or vice versa). The color coding can represent absolute distance or simply a ranking of distances. A color key can be provided to guide the healthcare worker. As an additional example, the larger arrow indicator 384 in FIG. 37 can indicate a discrete region that is further than the discrete region indicated by the smaller arrow indicator 384. Alternatively, the larger arrow could indicate a closer discrete region than the smaller arrow indicates. The distances indicated can be absolute distances or ranked distances. Indicia 387 (e.g., numerical values on the indicator) can represent absolute distance, e.g., in mm or in pixels, or scaled (relative) distance, e.g., from 1 to 10, (e.g., FIG. 38). The indicator can also utilize a combination of the aforementioned features. For instance, the indicator can be an arrow with numbers overlaid, where the arrow is located in the portion of the signaling zone closest to the adjacent discrete region of fluorescing tissue and the number reflects the distance in a unit of measurement between the edge of the image and the fluorescing region.

Figure 39:
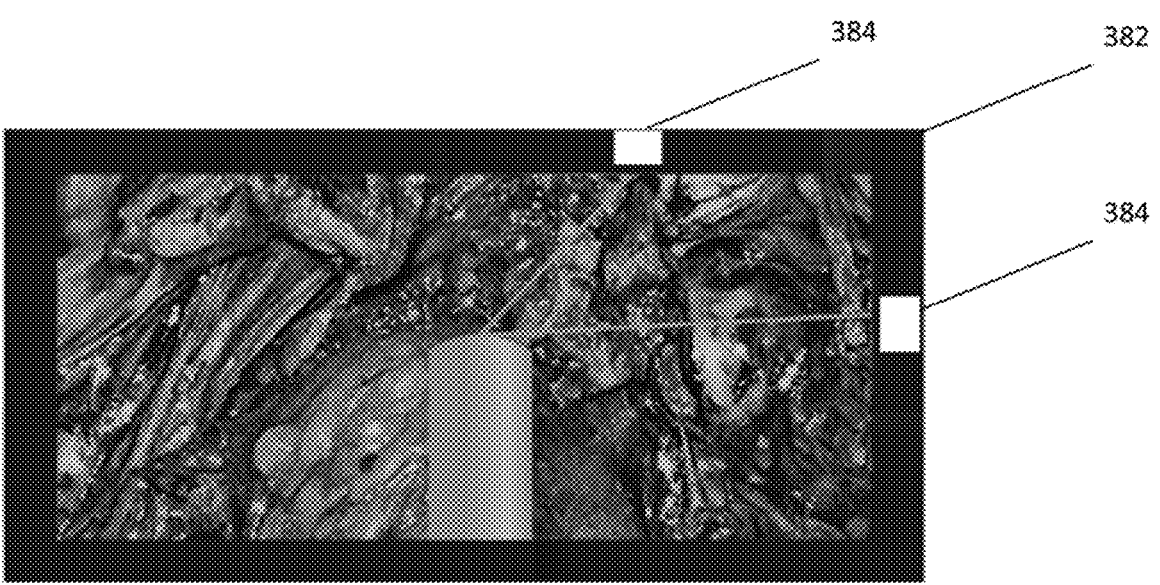
FIG. 39 is an image of an operating region, with indicators in the signal zone surrounding the image.
Figures 40, 41, 42:
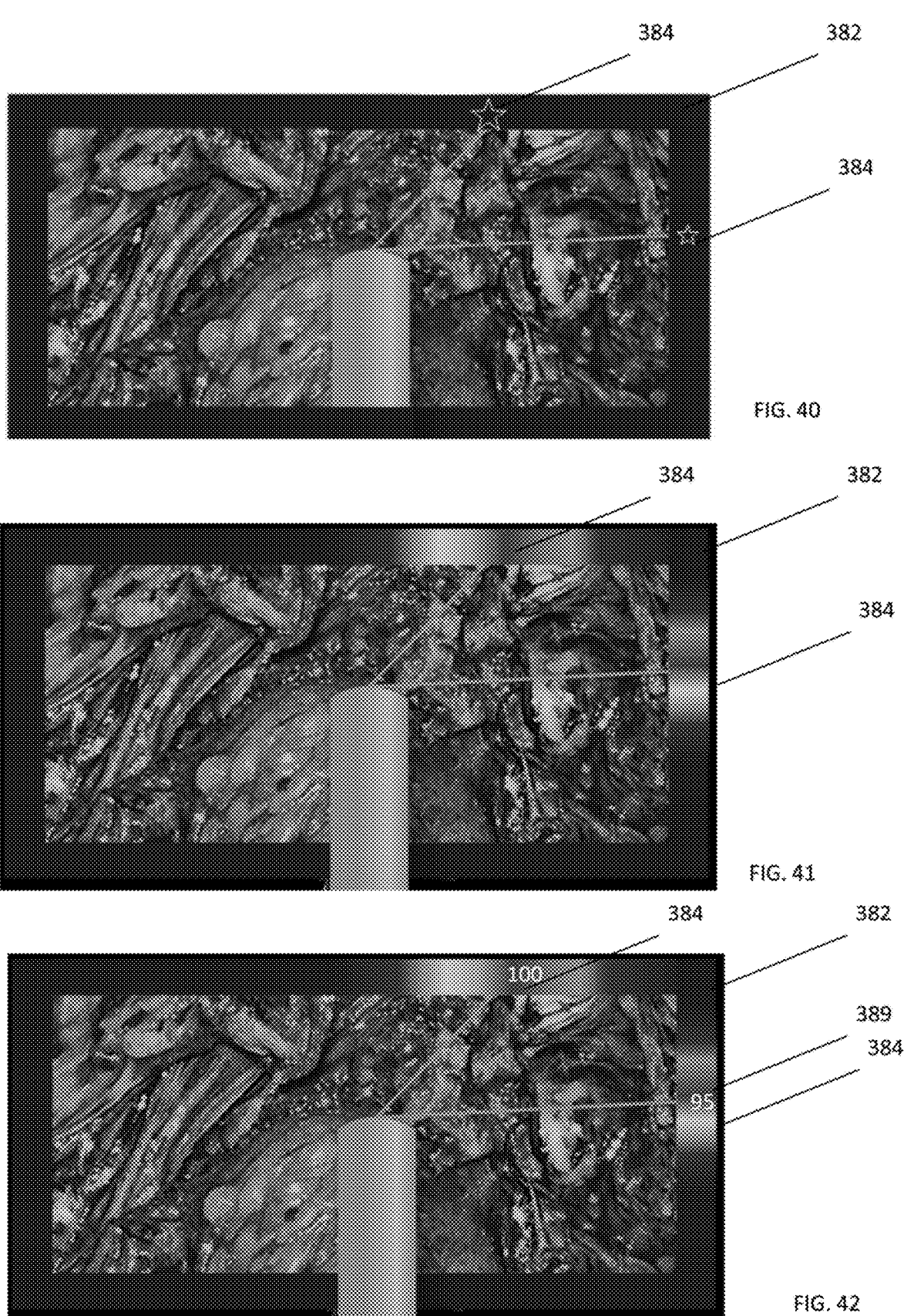
FIG. 40 is an image of an operating region, with indicators in the signal zone surrounding the image.
FIG. 41 is an image of an operating region, with indicators in the signal zone surrounding the image.
FIG. 42 is an image of an operating region, with indicators in the signal zone surrounding the image.

In a second alternative to the tenth embodiment, each indicator 384 can be coded to represent the intensity of the fluorescence of the tissue in its respective region (e.g., FIG. 39). Each indicator can represent intensity with the color or color properties (hue, saturation, brightness), shape, size, or width of the indicator, with indicia, with numbers, or with text (ex. letters, abbreviations, words). For example, for size, the relative size of the indicators 384 can indicate the relative intensity of the region indicated by each indicator. In this alternative the indicator can have one or more colors to represent intensity or intensity profile in the region being identified by the indicia. The indicator can be coded to represent the intensity relatively or via descriptive statistics including but not limited to the average (e.g., FIG. 42), minimum, maximum, median, or mode of the fluorescence pixel intensities in that fluorescing region. The intensity can be coded to represent the intensity at the center point of each respective region (e.g., FIG. 41) or at the point in each respective region closest to the image (e.g., FIG. 40). The size of the indicator 384 can indicate the intensity, with, for example the larger indicator 384 indicating the greater intensity.

In a third alternative to the tenth embodiment, each indicator 384 can be coded to represent the size of its respective fluorescing region. Each indicator can represent size with the color or color properties (hue, saturation, brightness), shape, size, or width of the indicator, with indicia, with numbers, or with text (ex. letters, abbreviations, words) (e.g., FIG. 36).

In a fourth alternative to the tenth embodiment, each indicator 384 can be coded to represent the rank order of importance of the tissue in its respective region. The rank order of importance can be based on a combination of the distance, size, or intensity of the adjacent discrete region of fluorescing tissue that is outside of the displayed image. An algorithm can combine the distance, size, and/or intensity data from each adjacent region of fluorescing tissue, assign each region an importance score, and then rank the importance of each region. Each indicator can represent the rank order of importance with the color or color properties (hue, saturation, brightness), shape, size, or width of the indicator, with indicia, with numbers, or with text (ex. letters, abbreviations, words).

An exemplary method of this tenth embodiment is indicated generally as 400 in FIG. 43. The method 400 can comprise at 402 near-Infrared Imaging of the surgical field under near infrared illumination, and at 404 processing the images to determine the location of the fluorescence (as described above). The method 400 can further comprise at 406 determining the location of the current imaged region in context of the entire region of interest. At 408, based on prior imaged regions, placing the currently imaged region in the appropriate context building a map of the surgical field. At 410 the distance and direction of discrete areas of fluorescence outside the current view from the current view are determined. At 412 indicators are positioned in the signaling zone surrounding the currently displayed image, according to whether the indicators are indicators of position, distance, size, or intensity. At 414 the currently displayed region is stored and added to the map of the surgical field.

Figures 35, 36, 37:
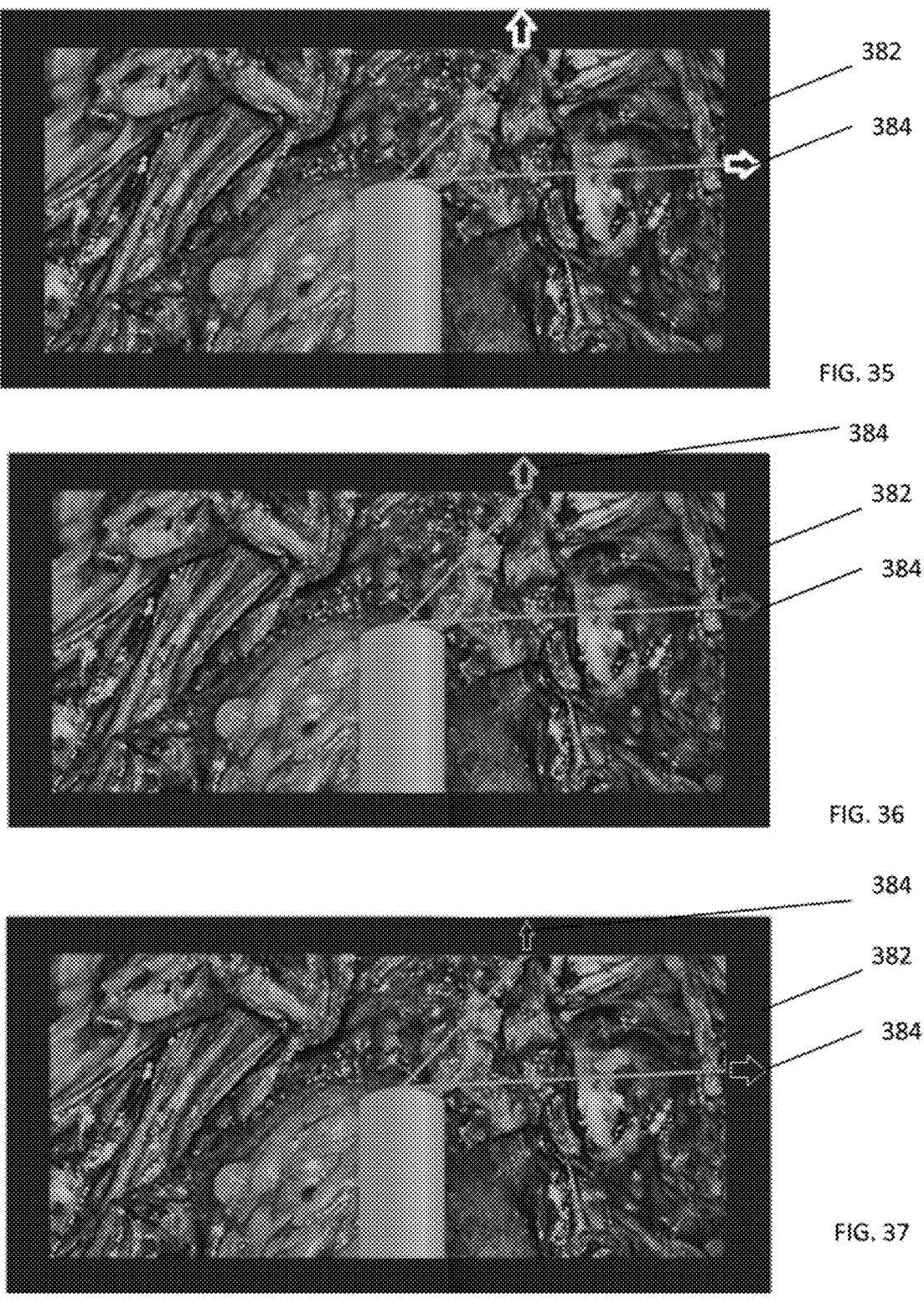
FIG. 35 is an image of an operating region, with indicators in the signal zone surrounding the image.
FIG. 36 is an image of an operating region, with indicators in the signal zone surrounding the image.
FIG. 37 is an image of an operating region, with indicators in the signal zone surrounding the image.

In a first alternative to the tenth embodiment, each indicator 384 can be coded to represent the distance between the edge of the image and its respective discrete region (e.g., FIG. 35). The distance could also be measured from the center of the discrete region being displayed, or preferably from the edge of the discrete region being displayed. Of course, the indicators could also represent the distance between the center of the current display, or the edge of the current display adjacent the indicator. Each indicator can represent distance with the color or color properties (hue, saturation, brightness) (e.g., FIG. 36), shape, size, or width of the indicator, with indicia, with numbers, or with text (ex. letters, abbreviations, words). For example, in FIG. 35 the red arrow could indicate a closer discrete region than the orange arrow indicates (or vice versa). The color coding can represent absolute distance or simply a ranking of distances. A color key can be provided to guide the healthcare worker. As an additional example, the larger arrow indicator 384 in FIG. 37 can indicate a discrete region that is further than the discrete region indicated by the smaller arrow indicator 384. Alternatively, the larger arrow could indicate a closer discrete region than the smaller arrow indicates. The distances indicated can be absolute distances or ranked distances. Indicia 387 (e.g., numerical values on the indicator) can represent absolute distance, e.g., in mm or in pixels, or scaled (relative) distance, e.g., from 1 to 10 (e.g., FIG. 38). The indicator can also utilize a combination of the aforementioned features. For instance, the indicator can be an arrow with numbers overlaid, where the arrow is located in the portion of the signaling zone closest to the adjacent discrete region of fluorescing tissue and the number reflects the distance in a unit of measurement between the edge of the image and the fluorescing region.

In a second alternative to the tenth embodiment, each indicator 384 can be coded to represent the intensity of the fluorescence of the tissue in its respective region (e.g., FIG. 39). Each indicator can represent intensity with the color or color properties (hue, saturation, brightness), shape, size, or width of the indicator, with indicia, with numbers, or with text (ex. letters, abbreviations, words). For example, for size, the relative size of the indicators 384 can indicate the relative intensity of the region indicated by each indicator. In this alternative the indicator can have one or more colors to represent intensity or intensity profile in the region being identified by the indicia. The indicator can be coded to represent the intensity relatively or via descriptive statistics including but not limited to the average (e.g., FIG. 42), minimum, maximum, median, or mode of the fluorescence pixel intensities in that fluorescing region. Additionally, fluorescence intensity pixel values can be pre-processed (for instance, scaled or clipped) before calculating the fluorescence value for each indicator. The intensity can be coded to represent the intensity at the center point of each respective region (e.g., FIG. 41) or at the point in each respective region closest to the image (e.g., FIG. 40). The size of the indicator 384 can indicate the intensity, with, for example the larger indicator 384 indicating the greater intensity.

In a third alternative to the tenth embodiment, each indicator 384 can be coded to represent the size of its respective fluorescing region. Each indicator can represent size with the color or color properties (hue, saturation, brightness), shape, size, or width of the indicator, with indicia, with numbers, or with text (ex. letters, abbreviations, words) (e.g., FIG. 36). The size of each fluorescing region can be determined by image segmentation methods such as thresholding or edge detection and can be represented in absolute terms (ex. pixel count) or relative terms by scaling or by comparison to the other regions.

In a fourth alternative to the tenth embodiment, each indicator 384 can be coded to represent the rank order of importance of the tissue in its respective region. The rank order of importance can be based on a combination of the distance, size, or intensity of the adjacent discrete region of fluorescing tissue that is outside of the displayed image. An algorithm can combine the distance, size, and/or intensity data from each adjacent region of fluorescing tissue, assign each region an importance score, and then rank the importance of each region. Each indicator can represent the rank order of importance with the color or color properties (hue, saturation, brightness), shape, size, or width of the indicator, with indicia, with numbers, or with text (ex. letters, abbreviations, words).

Edge Display

According to an eleventh embodiment a system and method of superimposing a signaling zone on or around an image is provided for viewing a surgical field containing a plurality of discrete regions of fluorescing tissue responsive to near-infrared illumination.

An exemplary embodiment of the eleventh embodiment is indicated generally as 450 in FIG. 44. The system 450 can comprise a source of near-infrared illumination 24, and at least one imaging camera 22 for imaging a portion of the surgical field SF. The system 450 may also include a source of white light illumination 26. The system 450 further comprises a display 30. The system 450 can additionally include at least one processor running a program for displaying the images from at least one camera 22 and for generating a signaling zone 462 on the display 30 at least partially surrounding the image of the portion of the surgical field, as shown in FIG. 45. The one or more processors can also include at least one processor for generating an indicator of the distance to the edge of the current discrete region of fluorescing tissue that is outside of the displayed image of that discrete region. In this preferred embodiment, this indicator is indicia 463, which numerically indicates the distance to the edge. This distance can be expressed in absolute terms, e.g., in mm, or it can be expressed in relative terms by scaling, for example on a scale of 1 to 10, or 1 to 7 as shown in FIG. 45A.

Figure 46:
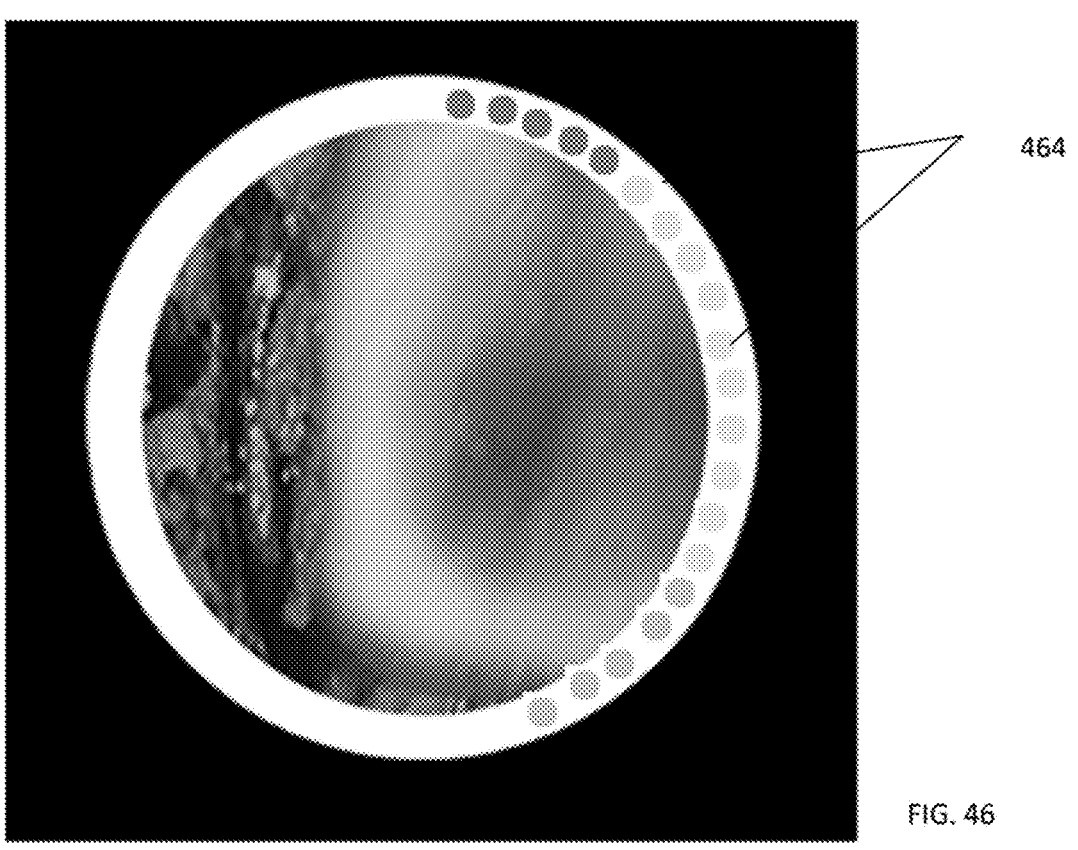
FIG. 46 is an image showing the field of view in the eleventh embodiment.
Figure 47:
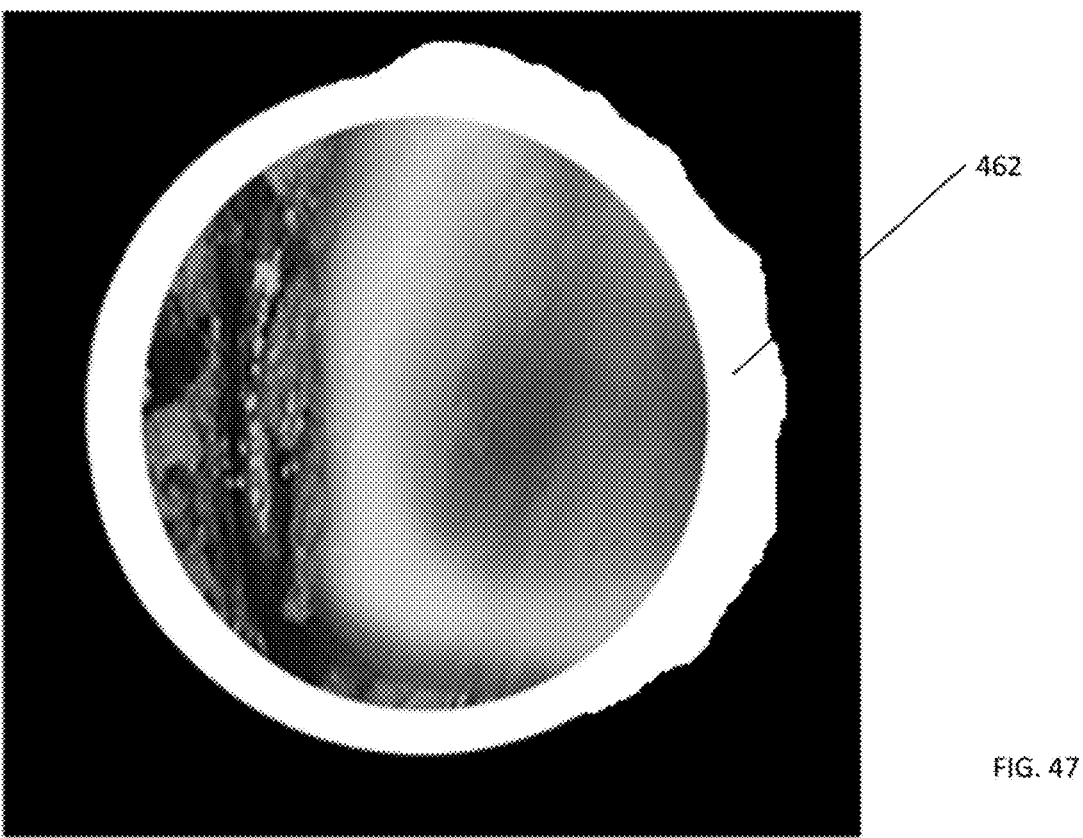
FIG. 47 is an image showing the field of view in the eleventh embodiment.
Figure 48:
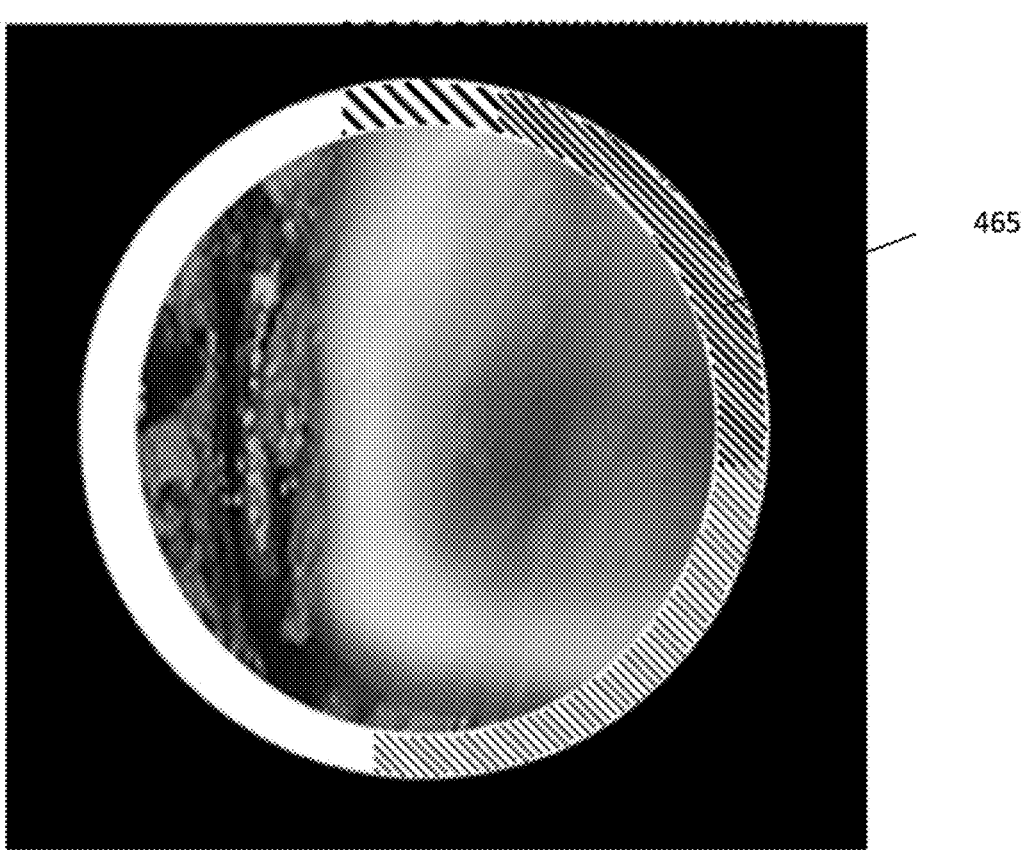
FIG. 48 is an image showing the field of view in the eleventh embodiment.
Figure 49:
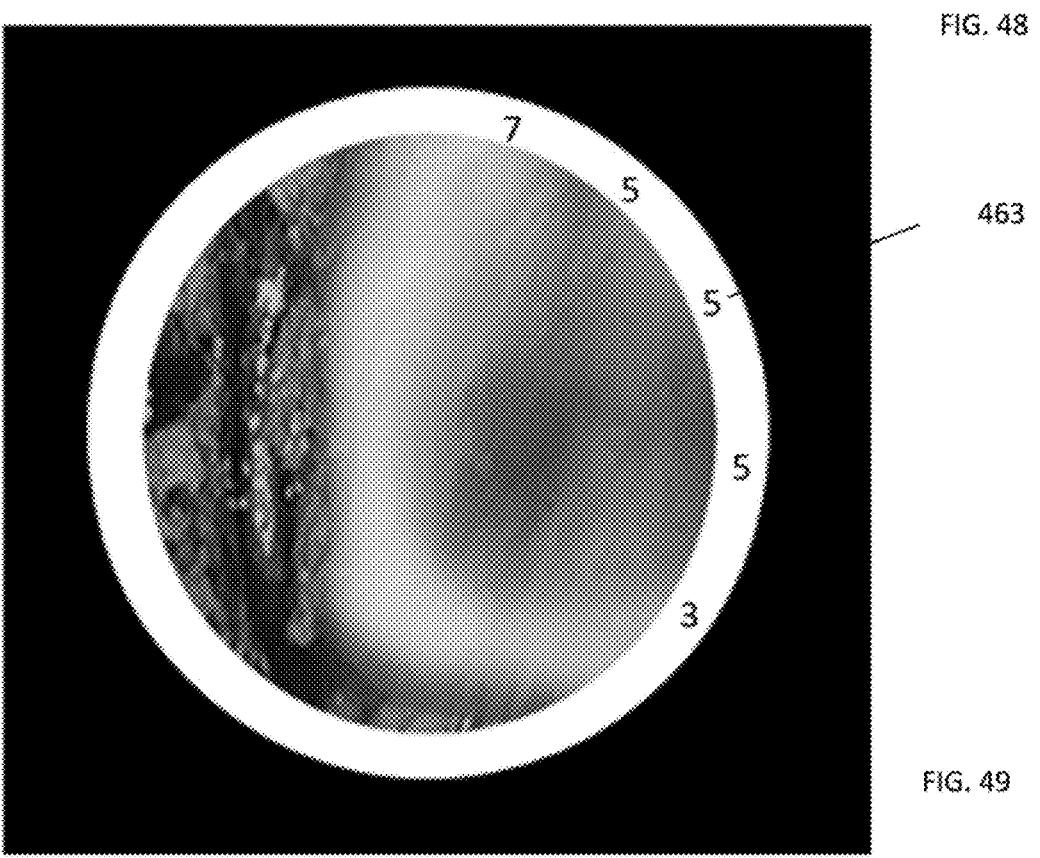
FIG. 49 is an image showing the field of view in the eleventh embodiment.

In a first alternative to the eleventh embodiment, the indicator can be color-coded markers 464 representing the distance between the edge of the image and the edge of the discrete region (e.g., FIG. 46). A key for the color coding is preferably provided for the users of the system. In a second alternative to the eleventh embodiment, the indicator is the width of the signaling zone representing the distance between the edge of the image and the edge of the discrete region (e.g., FIG. 47). The thicker the signaling zone at a particular location, the further the edge of the discrete region is from the edge of the image. In a third alternative to the twelfth embodiment, the indicator can be a pattern in the signaling zone representing the distance between the edge of the image and the edge of the discrete region (e.g., FIG. 48). A key for the pattern coding is preferably provided for the users of the system. In a fourth alternative to the eleventh embodiment, the indicator can be a numeral in the signaling zone representing the distance between the edge of the image and the edge of the discrete region (e.g., FIG. 49).

Figure 50:
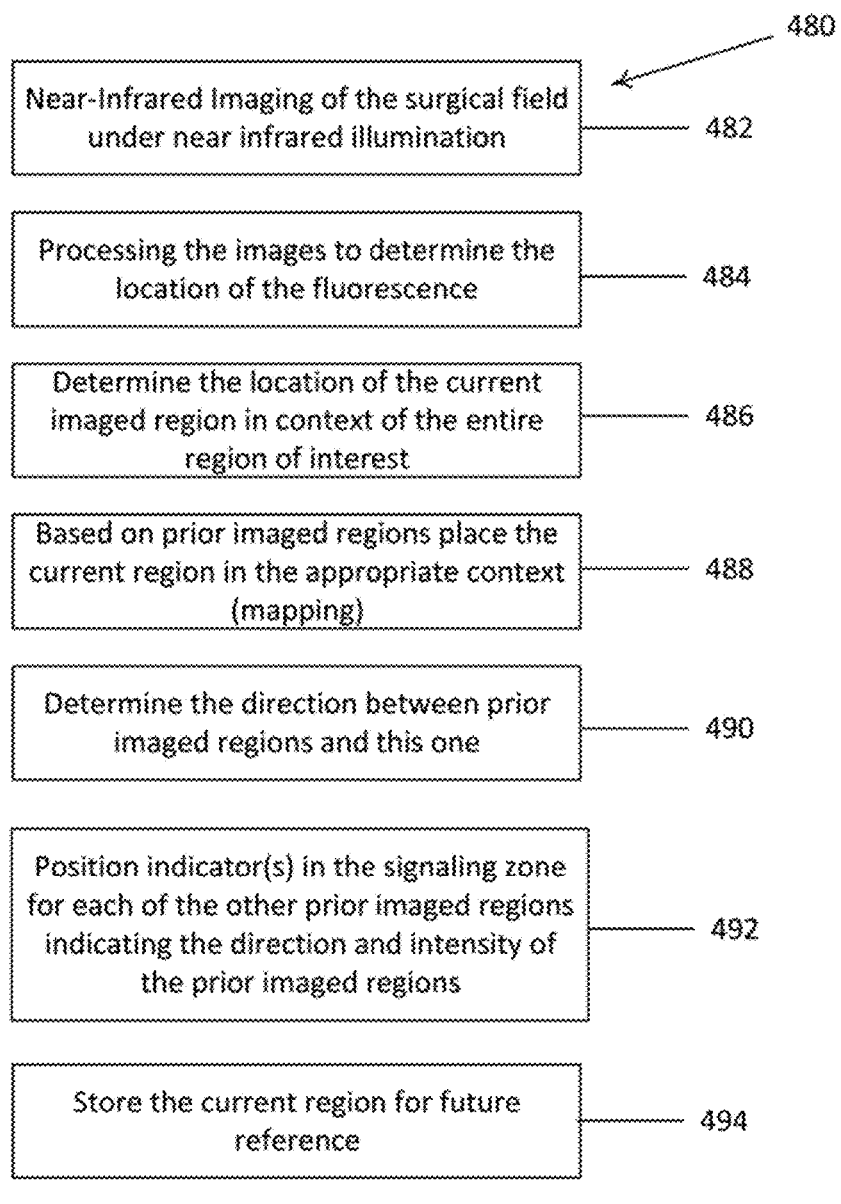
FIG. 50 is a flow chart of the method of the eleventh embodiment.

An exemplary method according to the eleventh embodiment is indicated generally as 480 in FIG. 50. The method 480 can comprise at 482 illuminating the surgical field with near-infrared illumination, and at 484 imaging a portion of the surgical field with the at least one camera 22 under near-infrared illumination. At 486, the images are processed to determine the location of the region in the overall surgical, and at 488 placing the current image in a real time map of the surgical site. The method 480 can further comprise at 490 determining the distance between the center of the discrete region of fluorescence and the edge of the discrete region of fluorescence in each direction. At 492, indicators 464 are positioned in the signaling zone 462 to indicate the distance to the edge of the discrete region of fluorescence from the signaling zone 462.

In a first alternative to the eleventh embodiment, the indicator can be color representing the distance between the edge of the image and the edge of the discrete region (e.g., FIG. 46). In a second alternative to the eleventh embodiment, the indicator is the width of the signaling zone representing the distance between the edge of the image and the edge of the discrete region (e.g., FIG. 47). In a third alternative to the eleventh embodiment, the indicator can be a pattern 465 in the signaling zone representing the distance between the edge of the image and the edge of the discrete region (e.g., FIG. 48). In a fourth alternative to the eleventh embodiment, the indicator can be a numeral indicium 463 in the signaling zone representing the distance between the edge of the image and the edge of the discrete region (e.g., FIG. 49).

Progress Indicator

According to a twelfth embodiment, a system and method of indicating the progress of a surgical procedure taking place in a surgical field containing a plurality of discrete regions of fluorescing tissue responsive to near-infrared illumination is provided.

Figure 51:
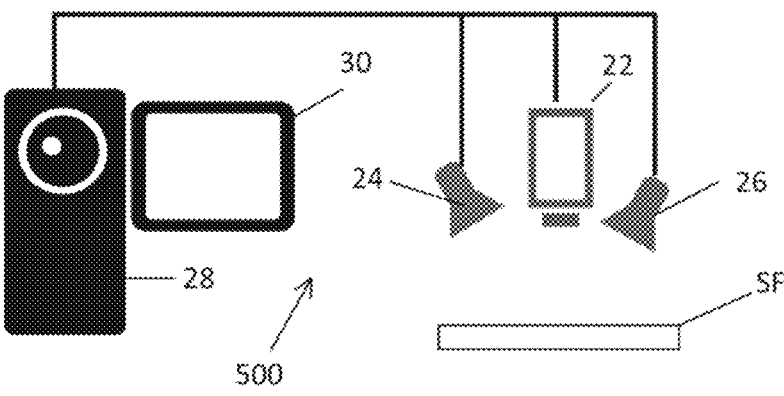
FIG. 51 is a schematic diagram of a twelfth preferred embodiment of a system for real time visualizing a surgical field containing a plurality of discrete regions of fluorescing tissue responsive to near-infrared illumination.

An exemplary system of the 12$^{th}$ embodiment is indicated generally as 500 in FIG. 51. The system 500 includes a source 24 of near-infrared light for illuminating the surgical field DF, and at least one camera 22 for imaging the surgical field. The system 500 can also include a source 26 pf white light for illuminating the surgical field.

The system 500 can comprise at least one processor for determining the total area of fluorescing tissue in the surgical field from an image of the surgical field. The at least one processor can be part of at least one computer 28. At least one processor can further display a progress indicator 512 (FIG. 52 on or in connection with a display of an image of a portion of the surgical field. The progress indicator 512 preferably comprises color bands representing fluorescence of different intensities in the surgical field. The progress indicator visually shows the amount fluorescing material removed and the amount of fluorescing tissue remaining. In an alternate embodiment of indicator 512, the indicator can comprise rather than the continuous bands shown in FIG. 52, the indicator can be a display of a series of similar geometric shapes each of whose area is proportional to the total area of the regions of fluorescing tissue remaining to be removed at a predetermined time intervals. The geometric shapes are preferably displayed in an oblique edge view. The geometric shape in the display is preferably a circle, but it could be some other shape, such as a square, rectangle, or other regular polygon.

An exemplary method of this twelfth embodiment is indicated generally as 520 in FIG. 53. The method 520 can comprise at 522 illuminating the surgical field with near-infrared illumination, and at 524 imaging a portion of the surgical field with a camera and determine its fluorescence index (total amount of fluorescence intensity present). The method 520 further comprises processing at 526 to determine the location of the current imaged region in the context of the entire surgical field, an at 528 to update the stored fluorescence index if the current region was processed before. At 530 the calculated fluorescence index and processed image location are stored for further reference. At 532 the overall fluorescence index (total of all fluorescence indexes calculated so far) are updated at regular intervals. At 534, a progress indicator is displayed on display 30, displaying a continuously updated representation of the fluorescent tissue remaining in the surgical field as bands of color each representing a range of intensities of fluorescence.

Alternatively, the progress indicator can be a series of geometric shapes, e.g., a circle, on edge with a diameter proportional to the remaining discrete region of fluorescence, showing the geometric shape at predetermined time intervals, the size of the most recent shape being indicative of the amount of fluorescent tissue remaining. The shape can be colored to represent the relative portions of the various ranges of intensities. The geometric shapes are preferably displayed in an oblique edge view. The geometric shape in the display is preferably a circle, but it could be some other shape, such as a square, rectangle, or other regular polygon.

According to a thirteenth embodiment, a system and method of indicating the progress is provided for a surgical procedure taking place in a surgical field containing a plurality of discrete regions of fluorescing tissue responsive to near-infrared illumination is provided.

Figure 54:
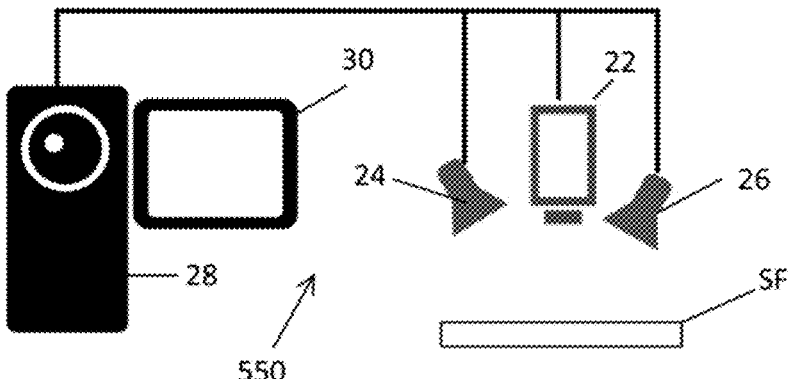
FIG. 54 is a schematic diagram of a thirteenth preferred embodiment of a system for real time visualizing a surgical field containing a plurality of discrete regions of fluorescing tissue responsive to near-infrared illumination.
Figure 55:
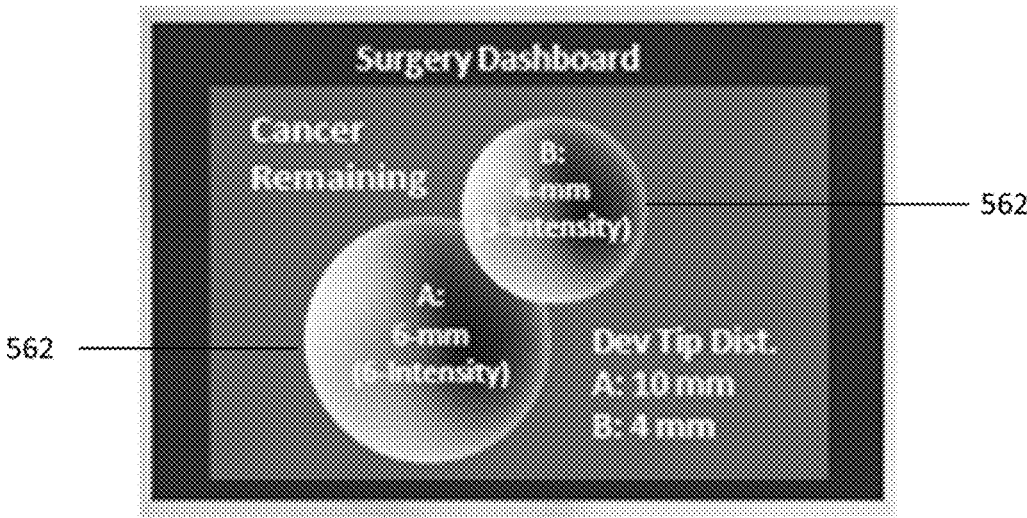
FIG. 55 is an image of the display of a system according to the system and method of the thirteenth embodiment.
Figure 56:
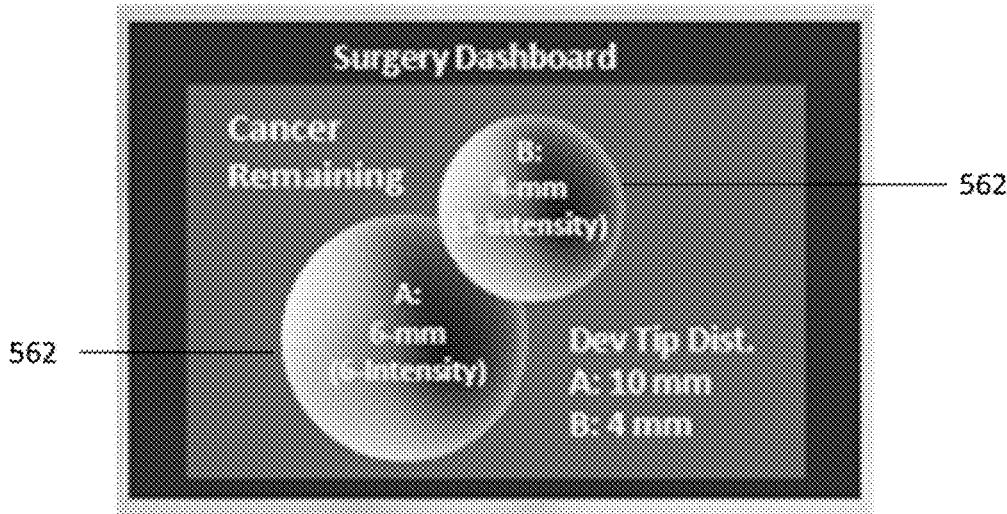
FIG. 56 is an image of the display of a system according to the system and method of the thirteenth embodiment.

An exemplary system of the fourteenth embodiment is indicated generally as 550 in FIG. 54. The system 550 can comprise a source of near-infrared illumination 24, and at least one imaging camera 22 for imaging a portion of the surgical field SF. The system 550 may also include a source of white light illumination 26. The system 550 further comprises a display 30. The system 550 can additionally include at least one processor running a program for identifying each discrete region of fluorescence and determining the area of each discrete region of fluorescing tissue in the surgical field. The at least one processor can be part of at least one computer 28. The at least one processor also can run a program that displays an indicator 562 on display 30 for each discrete region of fluorescence, the size of each shape being proportional to the area of the discrete region the indicator represents, thereby indicating the number and size of discrete regions of fluorescing tissue to be treated. The indicators are preferably all the same simple geometric shape, such as circles, but could be some other shape, such as a rectangle or other polygon. In some alternatives, the indicators 562 are the shapes of the fluorescent regions they represent. The shapes are preferably also color coded to indicate the intensity fluorescence of its corresponding discrete regions of fluorescing tissue (e.g., FIG. 55). The proportion of the various colors correspond to the proportion of the ranges of intensities in the corresponding region of fluorescing tissue.

The at least one processor can also determine the distance and/or direction of the tip of a medical device 554 in the surgical field from each of the discrete regions of fluorescing tissue and displaying the distance and/or direction on the display. The processor can also display a numerical value corresponding to the area of each region, and or distance of the tip from each region, and/or intensity of fluorescence (e.g., FIG. 55).

An exemplary method of the thirteenth embodiment is indicated generally as 570 in FIG. 57. The method 570 can comprise at 572 illuminating the surgical field with near-infrared illumination, and at 574 imaging a portion of the surgical field with a camera. The method 570 further comprises processing at 576 to identify each discrete region of fluorescence and determine the area of each discrete region of fluorescing tissue in the surgical field. At 578 the method comprises displaying an indicator 562 in display 560 for each discrete region of fluorescence, the size of each shape of the indicator being proportional to the area of the discrete region the indicator represents, thereby indicating the number and size of discrete regions of fluorescing tissue to be treated. The indicators 562 are preferably all the same simple geometric shape, such as circles, but could be some other shape, such as a rectangle or other polygon. In some alternatives, the indicators 562 are the shapes of the fluorescent regions they represent. The shapes are preferably also color coded to indicate the intensity fluorescence of its corresponding discrete regions of fluorescing tissue (e.g., FIG. 53).

The method can also include at 580 determining the distance and/or direction of the tip of a medical device in the surgical field from each of the discrete regions of fluorescing tissue and displaying the distance and/or direction on the display. The method can also include at 582 displaying a numerical value corresponding to the area of each region, and or distance of the tip from each region, and/or intensity of fluorescence.

Real-Time Updating

According to a fourteenth embodiment, a system and method of updating an image of a surgical field containing a plurality of discrete regions of fluorescing tissue responsive to near infrared illumination is provided.

An exemplary system of the fourteenth embodiment is indicated generally as 600 in FIG. 58. The system 600 can comprise a source of near-infrared illumination 24, and at least one imaging camera 22 for imaging a portion of the surgical field SF. The system 600 may also include a source of white light illumination 26. The system 600 further comprises a display 30. The system 600 can additionally include at least one processor running a program for real-time updating portions of the image of the surgical field as tissue removed from the discrete regions of fluorescing tissues changes the fluorescence of those portions. At least one processor can also superimpose an image of a medical device on the image in a location determined by registering an image currently generated from the medical device with the prior image of the surgical field.

An exemplary method of the fourteenth embodiment is indicated generally as 630 in FIG. 59. The method 630 can comprise at 632 illuminating the surgical field with near-infrared illumination, and at 634 imaging a portion of the surgical field with a camera. The method 630 further comprises processing at 636 to real-time update portions of the image of the surgical field as tissue removed from the discrete regions of fluorescing tissues changes the fluorescence of those portions. At 638, a medical device can be superimposed on the image of the surgical field in a location determined by registering an image currently generated from the medical device with the prior image of the surgical field, as shown in FIGS. 60A-60D.

Surface Scanner

According to a fourteenth embodiment, a system and method of creating an image of a surgical field containing a plurality of discrete regions of fluorescing tissue responsive to near-infrared illumination, is provided.

Figure 61:
FIG. 61 is a diagram showing the scanner of the fifteenth embodiment.

An embodiment of a system according to the fifteenth embodiment is indicated generally as 600 in FIG. 58. The system 600 can comprise a scanner, shown in FIG. 61, adapted to be moved over the body of the subject to create a scanned image of the surface including fluorescence from fluorescently tagged cancer cells at and below the surface. The scanner includes both a source 704 of near-infrared illumination to stimulate fluorescence, and a near-infrared camera 706 for detecting fluorescence. The system further comprises a processor for stitching together multiple scans using anatomical features in the images and fluorescent features in the images to make a composite map of surface and subsurface fluorescence.

The method comprises stitching together multiple surface scans using anatomical features in the images and fluorescent features in the images to make a composite map.

In an alternative to the fifteenth embodiment, the system 600 can comprise a scanner that, in addition to the source of near-infrared illumination and a near-infrared camera, has position and attitude sensors and that is adapted to be moved over the body to detect fluorescence. The processor uses position and attitude information to make a three-dimensional map of detected fluorescence.

The method comprises making a three-dimensional map using scanner position data and detected fluorescence.

While various embodiments of systems and methods have been described with particular reference to LS-301 and the detection and display of cancer using near-infrared fluorescence stimulated by near-infrared illumination, it should be understood that he invention is not so limited, and the visualization technique could be used with different fluorescent agents, with different stimulating illumination, with different fluorescence, and for detecting different kinds of diseased or healthy tissue other than cancerous tissue.

What is claimed is:

1. A system for visualizing a surgical field containing a plurality of discrete regions of fluorescing tissue, the system comprising:

an imaging camera for imaging a portion of the surgical field;

a display for displaying an image of the portion of the surgical field imaged by the camera;

a processor for generating a signaling zone on the display at least partially surrounding the image of the portion of the surgical field, and further displaying in this signaling zone an indicator of at least one adjacent discrete region of fluorescing tissue that is outside of the displayed image, each indicator located in that portion of the signaling zone closest to the adjacent discrete region of fluorescing tissue represented by the indicator.

2. The system according to claim 1 wherein the appearance of each indicator represents the distance between the edge of the image and the respective discrete region represented by the indicator.

3. The system according to claim 2 wherein at least one of the color of the indicator, size of the indicator, shape of the indicator, and/or indicia on the indicator, is representative of the distance between the edge of the image and the respective discrete region represented by the indicator.

4. The system according to claim 1 wherein the appearance of each indicator represents the intensity of the fluorescence of the tissue in the region represented by the indicator.

5. The system according to claim 4 wherein at least one of the color of the indicator, size of the indicator, shape of the indicator, and/or indicia on the indicator, is representative of the intensity of the fluorescence of the tissue in the region represented by the indicator.

6. The system according to claim 4 wherein the intensity of the fluorescence of the tissue in the region represented by the indicator is determined by at least one of: the intensity at the point in the region closest to the image, the intensity at the center point in the region, and/or the average intensity in the region.

7. The system according to claim 1 wherein the appearance of each indicator represents the size of the fluorescing region represented by the indicator.

8. The system according to claim 7 wherein at least one of the color of the indicator, size of the indicator, shape of the indicator, and/or or indicia on the indicator, is representative of the size of the fluorescing region represented by the indicator.

9. The system according to claim 1 wherein the appearance of each indicator represents the importance of the region represented by the indicator, as determined with a predetermined algorithm based upon at least one of distance, size, fluorescence, and/or the importance of other regions represented by indicators on the signaling zone.

10. The system according to claim 9 wherein at least one of the color of the indicator, size of the indicator, shape of the indicator, or indicia on the indicator is representative of the importance of the region represented by the indicator, as determined with a predetermined algorithm based upon at least one of distance, size, fluorescence, and/or the importance of other regions represented by indicators on the signaling zone.

11. A method for visualizing a surgical field containing a plurality of discrete regions of fluorescing tissue, the method comprising:

imaging a portion of the surgical field with a camera;

displaying an image of the portion of the surgical field captured by the camera;

generating a signaling zone on the display at least partially surrounding the image of the portion of the surgical field, and displaying in this signaling zone an indicator of at least one adjacent discrete region of fluorescing tissue that is outside of the displayed image, each indicator located in that portion of the signaling zone closest to the adjacent discrete region of fluorescing tissue that the indicator represents.

12. The method according to claim 11 wherein the appearance of each indicator represents the distance between the edge of the image and the respective discrete region represented by the indicator.

13. The method according to claim 12 wherein at least one of the color of the indicator, size of the indicator, shape of the indicator, and/or or indicia on the indicator is representative of the distance between the edge of the image and the respective discrete region represented by the indicator.

14. The method according to claim 11 wherein the appearance of each indicator represents the intensity of the fluorescence of the tissue in the region represented by the indicator.

15. The method according to claim 14 wherein at least one of the color of the indicator, size of the indicator, shape of the indicator, and/or indicia on the indicator is representative of the intensity of the fluorescence of the tissue in the region represented by the indicator.

16. The method according to claim 14 wherein the intensity of the fluorescence of the tissue in the region represented by the indicator is determined by at least one of: the intensity at the point in the region closest to the image, the intensity at the center point in the region, or the average intensity in the region.

17. The method according to claim 11 wherein the appearance of each indicator represents the size of the fluorescing region represented by the indicator.

18. The method according to claim 17 wherein at least one of the color of the indicator, size of the indicator, shape of the indicator, and/or or indicia on the indicator is representative of the size of the fluorescing region represented by the indicator.

19. The method according to claim 11 wherein the appearance of each indicator represents the importance of the region represented by the indicator, as determined with a predetermined algorithm based upon at least one of distance, size, fluorescence, and/or the importance of other regions represented by indicators on the signaling zone.

20. The method according to claim 19 wherein at least one of the color of the indicator, size of the indicator, shape of the indicator, and/or indicia on the indicator is representative of the importance of the region represented by the indicator, as determined with the predetermined algorithm based upon the at least one of distance, size, fluorescence, and/or the importance of other regions represented by indicators on the signaling zone.

* * * * *